US008518904B2

(12) United States Patent
Shanahan, Jr. et al.

(10) Patent No.: US 8,518,904 B2
(45) Date of Patent: Aug. 27, 2013

(54) MODULATION OF STAT 6 EXPRESSION

(75) Inventors: William R. Shanahan, Jr., Del Mar, CA (US); Susan M. Freier, San Diego, CA (US); Kenneth W. Dobie, Del Mar, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 13/350,691

(22) Filed: Jan. 13, 2012

(65) Prior Publication Data

US 2012/0115932 A1    May 10, 2012

Related U.S. Application Data

(60) Continuation of application No. 12/510,132, filed on Jul. 27, 2009, now abandoned, which is a continuation of application No. 11/152,530, filed on Jun. 14, 2005, now abandoned, which is a division of application No. 10/317,391, filed on Dec. 11, 2002, now abandoned.

(51) Int. Cl.
| | |
|---|---|
| *C12N 15/11* | (2006.01) |
| *A61K 48/00* | (2006.01) |
| *C07H 21/02* | (2006.01) |
| *C07H 21/04* | (2006.01) |

(52) U.S. Cl.
USPC .................. 514/44 A; 536/23.1; 536/24.5

(58) Field of Classification Search
USPC ................. 536/23.1, 24.5; 514/44
See application file for complete search history.

(56) References Cited

U.S. PATENT DOCUMENTS

| | | | |
|---|---|---|---|
| 5,710,266 A | 1/1998 | McKnight et al. | |
| 5,801,154 A | 9/1998 | Baracchini et al. | |
| 6,114,517 A | 9/2000 | Monia et al. | |
| 6,207,391 B1 | 3/2001 | Wu et al. | |
| 6,368,828 B1 | 4/2002 | LaRochelle et al. | |
| 6,582,908 B2 | 6/2003 | Fodor et al. | |
| 6,699,677 B1 | 3/2004 | Schall et al. | |
| 7,566,700 B2 | 7/2009 | Walker et al. | |
| 7,662,948 B2 * | 2/2010 | Kurreck et al. | 536/24.5 |
| 2001/0053519 A1 | 12/2001 | Fodor et al. | |
| 2003/0228597 A1 | 12/2003 | Cowsert et al. | |
| 2004/0115634 A1 | 6/2004 | Shanahan et al. | |
| 2004/0171566 A1 | 9/2004 | Monia et al. | |
| 2004/0235164 A1 | 11/2004 | Bennett et al. | |
| 2005/0239124 A1 | 10/2005 | Shanahan et al. | |

FOREIGN PATENT DOCUMENTS

| | | | |
|---|---|---|---|
| JP | 2000229959 | | 8/2000 |
| WO | WO 9710322 | * | 3/1997 |
| WO | WO 98/35978 | | 8/1998 |
| WO | WO 98/40478 | | 9/1998 |
| WO | WO 99/10493 | | 3/1999 |
| WO | WO 99/14226 | | 3/1999 |
| WO | WO 99/60166 | | 11/1999 |
| WO | WO 00/27802 | | 5/2000 |
| WO | WO0194376 A1 | * | 12/2001 |
| WO | WO 02/40647 | | 5/2002 |
| WO | WO 02/088328 | | 11/2002 |
| WO | WO 02/096943 | | 12/2002 |
| WO | WO 2004052309 | | 6/2004 |
| WO | WO 2004108945 | | 12/2004 |

OTHER PUBLICATIONS

Agrawal et al., "Antisense therapeutics: is it as simple as complementary base recognition" Molecular Medicine Today (2000) 6:72-81.
Branch et al., "A good antisense molecule is hard to find" TIBS (1998) 23:45-50.
Bromberg, "Activation of STAT proteins and growth control" BioEssays (2001) 23:161-169.
Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.
Crooke et al., "Basic Principles of Antisense Therapeutics" Antisense Research and Application (1998) Chapter 1:1-50.
Danahay et al., "The in vitro and in vivo pharmacology of antisense oligonucleotides targeted to murine Stat6" Inflamm. Res. (2000) 49:692-699.
Ghilardi et al., "Defective STAT signaling by the leptin receptor in diabetic mice" PNAS (1996) 93:6231-6235.
Hill et al., "Homologous Human and Murine antisense oligonucleotide targeting stat6. Functional effects on germline c epsilon transcript" Am. J. Respir. Cell Mol. Biol. (1999) 22:728-737.
Ihle, "The Stat family in cytokine signaling" Curr. Opin. Cell Biol. (2001) 13:211-217.
Jen et al., "Suppression of Gene Expression by Targeted Disruption of Messenger RNA: Available Options and Curren Strategies" Stem Cells (2000) 18:307-319.
Kumar et al., "Murine Model of Chronic Human Asthma" Immunology and Cell Biology (2001) 79:141-144.
Kuperman et al., "Signal transducer and activator of transcription factor 6 (Stat6)-deficient mice are protected from antigen-induced airway hyperresponsiveness and mucus production" J. Exp. Med. (1998) 187:939-948.
Leek et al., "Assignment of the STAT6 gene (STAT6) to human chromosome band 12q13 by in situ hybridization" Cytogenet. Cell Genet. (1997) 79:208-209.
Muller-Ladner et al., "Activation of the IL-4 STAT pathway in rheumatoid synovium" J. Immunol. (2000) 164:3894-3901.
New England Biolabs 1998/1999 Catalog, cover page, pp. 121 and 284.
Nyce, "Respirable antisense oligonucleotides as novel therapeutic agents for asthma and other pulmonary diseases" Expert. Opin. Investig. Drugs (1997) 6(9):1149-1156.
Nyce et al., "DNA antisense therapy for asthma in an animal model" Nature (1997) 385(6618):721-725.
Opalinska et al., "Nucleic-Acid Therapeutics: Basic Principles and Recent Applications" Nature Reviews Drug Discovery (2002) 1:503-514.

(Continued)

*Primary Examiner* — Terra Cotta Gibbs

(74) *Attorney, Agent, or Firm* — Knobbe, Martens, Olson & Bear, LLP

(57) ABSTRACT

Compounds, compositions and methods are provided for modulating the expression of STAT 6. The compositions comprise oligonucleotides, targeted to nucleic acid encoding STAT 6. Methods of using these compounds for modulation of STAT 6 expression and for diagnosis and treatment of disease associated with expression of STAT 6 are provided.

20 Claims, No Drawings

(56) References Cited

OTHER PUBLICATIONS

Patil et al., "DNA-based therapeutics and DNA delivery systems: A comprehensive review" The AAPS Journal (2005) 7:E61-E77.

Quelle et al., "Cloning of murine Stat6 and human Stat6, Stat proteins that are tyrosine phosphorylated in responses to IL-4 and IL-3 but are not required for mitogenesis" Mol. Cell Biol. (1995) 15:3336-3343.

Reynolds et al., "Rational siRNA design for RNA interference" Nature Biotechnology (2004) 22(3):326-330.

Richards, "Mouse models of allergic disease; how do they relate to asthma in man?" Clinical and Experimental Allergy (1996) 26:618-620.

Sanghvi et al., "Heterocyclic Base Modifications in Nucleic Acids and Their Applications in Antisense Oligonucleotides" Antisense Research and Applications (1993) pp. 273-288.

Sherman, "The role of STAT6 in mast cell IL-4 production" Immunol. Rev. (2001) 179:48-56.

Taylor et al., "Antisense oligonucleotides: a systematic high-throughput approach to target validation and gene function determination" Drug Discovery Today (1999) 4(12):562-567.

Temelkovski et al., "An improved murine model of asthma selective airway inflammation, epithelial lesions and increased methacholine responsiveness following chronic exposure to aerosolised allergan" Thorax (1998) 53:849-856.

Trifilieff et al., "Abrogation of lung inflammation in sensitized Stat6-deficient mice is dependent on the allergen inhalation procedure" British Journal of Pharmacology (2000) 130:1581-1588.

Wang et al., "Targeted disruption of stat6 in DNA binding activity by an oligonucleotide decoy blocks IL-4-drien T(H)2 cell response" Blood (2000) 95:1249-1257.

Wong, "Inhibitors of the tyrosine kinase signaling cascade for asthma" Current Opinion in Pharmacology (2005) 5:264-271.

Extended European Search Report for Application No. 06759763.3 dated Oct. 7, 2008.

International Search Report for Application No. PCT/US06/18573 dated Nov. 13, 2006.

International Search Report for Application No. PCT/US03/39492 dated Feb. 28, 2005.

* cited by examiner

SEQUENCE LISTING

<160> NUMBER OF SEQ ID NOS: 141

<210> SEQ ID NO 1
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 1
tccgtcatcg ctcctcaggg                                            20

<210> SEQ ID NO 2
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 2
gtgcgcgcga gcccgaaatc                                            20

```
<210> SEQ ID NO 3
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 3
atgcattctg cccccaagga                                            20

<210> SEQ ID NO 4
<211> LENGTH: 3046
<212> TYPE: DNA
<213> ORGANISM: H. sapiens
<220> FEATURE:
<221> NAME/KEY: CDS
<222> LOCATION: (166)...(2709)

<400> SEQUENCE: 4
atcttatttt tcttttggt ggtggtggtg aagggggga ggtgctagca gggccagcct    60
tgaactcgct ggacagagct acagacctat ggggcctgga agtgcccgct gagaaaggga   120
gaagacagca gaggggttgc cgaggcaacc tccaagtccc agatc atg tct ctg tgg  177
                                                 Met Ser Leu Trp
                                                  1 ggt ctg gtc tcc aag atg ccc cca gaa aaa gtg cag cgg ctc tat gtc    225
Gly Leu Val Ser Lys Met Pro Pro Glu Lys Val Gln Arg Leu Tyr Val
  5                  10                  15                  20 gac ttt ccc caa cac ctg cgg cat ctt ctg ggt gac tgg ctg gag agc    273
Asp Phe Pro Gln His Leu Arg His Leu Leu Gly Asp Trp Leu Glu Ser
             25                  30                  35 cag ccc tgg gag ttc ctg gtc ggc tcc gac gcc ttc tgc tgc aac ttg    321
Gln Pro Trp Glu Phe Leu Val Gly Ser Asp Ala Phe Cys Cys Asn Leu
         40                  45                  50 gct agt gcc cta ctt tca gac act gtc cag cac ctt cag gcc tcg gtg    369
Ala Ser Ala Leu Leu Ser Asp Thr Val Gln His Leu Gln Ala Ser Val
     55                  60                  65 gga gag cag ggg gag ggg agc acc atc ttg caa cac atc agc acc ctt    417
Gly Glu Gln Gly Glu Gly Ser Thr Ile Leu Gln His Ile Ser Thr Leu
 70                  75                  80 gag agc ata tat cag agg gac ccc ctg aag ctg gtg gcc act ttc aga    465
Glu Ser Ile Tyr Gln Arg Asp Pro Leu Lys Leu Val Ala Thr Phe Arg
 85                  90                  95                 100 caa ata ctt caa gga gag aaa aaa gct gtt atg gaa cag ttc cgc cac    513
Gln Ile Leu Gln Gly Glu Lys Lys Ala Val Met Glu Gln Phe Arg His
                105                 110                 115 ttg cca atg cct ttc cac tgg aag cag gaa gaa ctc aag ttt aag aca    561
Leu Pro Met Pro Phe His Trp Lys Gln Glu Glu Leu Lys Phe Lys Thr
            120                 125                 130 ggc ttg cgg agg ctg cag cac cga gta ggg gag atc cac ctt ctc cga    609
Gly Leu Arg Arg Leu Gln His Arg Val Gly Glu Ile His Leu Leu Arg
        135                 140                 145 gaa gcc ctg cag aag ggg gct gag gct ggc caa gtg tct ctg cac agc    657
Glu Ala Leu Gln Lys Gly Ala Glu Ala Gly Gln Val Ser Leu His Ser
    150                 155                 160 ttg ata gaa act cct gct aat ggg act ggg cca agt gag gcc ctg gcc    705
Leu Ile Glu Thr Pro Ala Asn Gly Thr Gly Pro Ser Glu Ala Leu Ala
165                 170                 175                 180 atg cta ctg cag gag acc act gga gag cta gag gca gcc aaa gcc cta    753
Met Leu Leu Gln Glu Thr Thr Gly Glu Leu Glu Ala Ala Lys Ala Leu
                185                 190                 195 gtg ctg aag agg atc cag att tgg aaa cgg cag cag cag ctg gca ggg    801
```

```
                Val Leu Lys Arg Ile Gln Ile Trp Lys Arg Gln Gln Gln Leu Ala Gly
                                200                 205                 210 aat ggc gca ccg ttt gag gag agc ctg gcc cca ctc cag gag agg tgt          849
Asn Gly Ala Pro Phe Glu Glu Ser Leu Ala Pro Leu Gln Glu Arg Cys
            215                 220                 225 gaa agc ctg gtg gac att tat tcc cag cta cag cag gag gta ggg gcg          897
Glu Ser Leu Val Asp Ile Tyr Ser Gln Leu Gln Gln Glu Val Gly Ala
        230                 235                 240 gct ggt ggg gag ctt gag ccc aag acc cgg gca tcg ctg act ggc cgg          945
Ala Gly Gly Glu Leu Glu Pro Lys Thr Arg Ala Ser Leu Thr Gly Arg
245                 250                 255                 260 ctg gat gaa gtc ctg aga acc ctc gtc acc agt tgc ttc ctg gtg gag          993
Leu Asp Glu Val Leu Arg Thr Leu Val Thr Ser Cys Phe Leu Val Glu
                265                 270                 275 aag cag ccc ccc cag gta ctg aag act cag acc aag ttc cag gct gga         1041
Lys Gln Pro Pro Gln Val Leu Lys Thr Gln Thr Lys Phe Gln Ala Gly
            280                 285                 290 gtt cga ttc ctg ttg ggc ttg agg ttc ctg ggg gcc cca gcc aag cct         1089
Val Arg Phe Leu Leu Gly Leu Arg Phe Leu Gly Ala Pro Ala Lys Pro
        295                 300                 305 ccg ctg gtc agg gcc gac atg gtg aca gag aag cag gcg cgg gag ctg         1137
Pro Leu Val Arg Ala Asp Met Val Thr Glu Lys Gln Ala Arg Glu Leu
310                 315                 320 agt gtg cct cag ggt cct ggg gct gga gca gaa agc act gga gaa atc         1185
Ser Val Pro Gln Gly Pro Gly Ala Gly Ala Glu Ser Thr Gly Glu Ile
325                 330                 335                 340 atc aac aac act gtg ccc ttg gag aac agc att cct ggg aac tgc tgc         1233
Ile Asn Asn Thr Val Pro Leu Glu Asn Ser Ile Pro Gly Asn Cys Cys
                345                 350                 355 tct gcc ctg ttc aag aac ctg ctt ctc aag aag atc aag cgg tgt gag         1281
Ser Ala Leu Phe Lys Asn Leu Leu Leu Lys Lys Ile Lys Arg Cys Glu
            360                 365                 370 cgg aag ggc act gag tct gtc aca gag gag aag tgc gct gtg ctc ttc         1329
Arg Lys Gly Thr Glu Ser Val Thr Glu Glu Lys Cys Ala Val Leu Phe
        375                 380                 385 tct gcc agc ttc aca ctt ggc ccc ggc aaa ctc ccc atc cag ctc cag         1377
Ser Ala Ser Phe Thr Leu Gly Pro Gly Lys Leu Pro Ile Gln Leu Gln
390                 395                 400 gcc ctg tct ctg ccc ctg gtg gtc atc gtc cat ggc aac caa gac aac         1425
Ala Leu Ser Leu Pro Leu Val Val Ile Val His Gly Asn Gln Asp Asn
405                 410                 415                 420 aat gcc aaa gcc act atc ctg tgg gac aat gcc ttc tct gag atg gac         1473
Asn Ala Lys Ala Thr Ile Leu Trp Asp Asn Ala Phe Ser Glu Met Asp
                425                 430                 435 cgc gtg ccc ttt gtg gtg gct gag cgg gtg ccc tgg gag aag atg tgt         1521
Arg Val Pro Phe Val Val Ala Glu Arg Val Pro Trp Glu Lys Met Cys
            440                 445                 450 gaa act ctg aac ctg aag ttc atg gct gag gtg ggg acc aac cgg ggg         1569
Glu Thr Leu Asn Leu Lys Phe Met Ala Glu Val Gly Thr Asn Arg Gly
        455                 460                 465 ctg ctc cca gag cac ttc ctc ttc ctg gcc cag aag atc ttc aat gac         1617
Leu Leu Pro Glu His Phe Leu Phe Leu Ala Gln Lys Ile Phe Asn Asp
470                 475                 480 aac agc ctc agt atg gag gcc ttc cag cac cgt tct gtg tcc tgg tcg         1665
Asn Ser Leu Ser Met Glu Ala Phe Gln His Arg Ser Val Ser Trp Ser
485                 490                 495                 500 cag ttc aac aag gag atc ctg ctg ggc cgt ggc ttc acc ttt tgg cag         1713
Gln Phe Asn Lys Glu Ile Leu Leu Gly Arg Gly Phe Thr Phe Trp Gln
                505                 510                 515 tgg ttt gat ggt gtc ctg gac ctc acc aaa cgc tgt ctc cgg agc tac         1761
```

```
                  Trp Phe Asp Gly Val Leu Asp Leu Thr Lys Arg Cys Leu Arg Ser Tyr
                              520                 525                 530 tgg tct gac cgg ctg atc att ggc ttc atc agc aaa cag tac gtt act         1809
Trp Ser Asp Arg Leu Ile Ile Gly Phe Ile Ser Lys Gln Tyr Val Thr
            535                 540                 545 agc ctt ctt ctc aat gag ccc gac gga acc ttt ctc ctc cgc ttc agc         1857
Ser Leu Leu Leu Asn Glu Pro Asp Gly Thr Phe Leu Leu Arg Phe Ser
        550                 555                 560 gac tca gag att ggg ggc atc acc att gcc cat gtc atc cgg ggc cag         1905
Asp Ser Glu Ile Gly Gly Ile Thr Ile Ala His Val Ile Arg Gly Gln
565                 570                 575                 580 gat ggc tct cca cag ata gag aac atc cag cca ttc tct gcc aaa gac         1953
Asp Gly Ser Pro Gln Ile Glu Asn Ile Gln Pro Phe Ser Ala Lys Asp
            585                 590                 595 ctg tcc att cgc tca ctg ggg gac cga atc cgg gat ctt gct cag ctc         2001
Leu Ser Ile Arg Ser Leu Gly Asp Arg Ile Arg Asp Leu Ala Gln Leu
        600                 605                 610 aaa aat ctc tat ccc aag aag ccc aag gat gag gct ttc cgg agc cac         2049
Lys Asn Leu Tyr Pro Lys Lys Pro Lys Asp Glu Ala Phe Arg Ser His
615                 620                 625 tac aag cct gaa cag atg ggt aag gat ggc agg ggt tat gtc cca gct         2097
Tyr Lys Pro Glu Gln Met Gly Lys Asp Gly Arg Gly Tyr Val Pro Ala
            630                 635                 640 acc atc aag atg acc gtg gaa agg gac caa cca ctt cct acc cca gag         2145
Thr Ile Lys Met Thr Val Glu Arg Asp Gln Pro Leu Pro Thr Pro Glu
645                 650                 655                 660 ctc cag atg cct acc atg gtg cct tct tat gac ctt gga atg gcc cct         2193
Leu Gln Met Pro Thr Met Val Pro Ser Tyr Asp Leu Gly Met Ala Pro
            665                 670                 675 gat tcc tcc atg agc atg cag ctt ggc cca gat atg gtg ccc cag gtg         2241
Asp Ser Ser Met Ser Met Gln Leu Gly Pro Asp Met Val Pro Gln Val
        680                 685                 690 tac cca cca cac tct cac tcc atc ccc ccg tat caa ggc ctc tcc cca         2289
Tyr Pro Pro His Ser His Ser Ile Pro Pro Tyr Gln Gly Leu Ser Pro
    695                 700                 705 gaa gaa tca gtc aac gtg ttg tca gcc ttc cag gag cct cac ctg cag         2337
Glu Glu Ser Val Asn Val Leu Ser Ala Phe Gln Glu Pro His Leu Gln
710                 715                 720 atg ccc ccc agc ctg ggc cag atg agc ctg ccc ttt gac cag cct cac         2385
Met Pro Pro Ser Leu Gly Gln Met Ser Leu Pro Phe Asp Gln Pro His
725                 730                 735                 740 ccc cag ggc ctg ctg ccg tgc cag cct cag gag cat gct gtg tcc agc         2433
Pro Gln Gly Leu Leu Pro Cys Gln Pro Gln Glu His Ala Val Ser Ser
            745                 750                 755 cct gac ccc ctc ctc tgc tca gat gtg acc atg gtg gaa gac agc tgc         2481
Pro Asp Pro Leu Leu Cys Ser Asp Val Thr Met Val Glu Asp Ser Cys
        760                 765                 770 ctg agc cag cca gtg aca gcg ttt cct cag ggc act tgg att ggt gaa         2529
Leu Ser Gln Pro Val Thr Ala Phe Pro Gln Gly Thr Trp Ile Gly Glu
    775                 780                 785 gac ata ttc cct cct ctg ctg cct ccc act gaa cag gac ctc act aag         2577
Asp Ile Phe Pro Pro Leu Leu Pro Pro Thr Glu Gln Asp Leu Thr Lys
790                 795                 800 ctt ctc ctg gag ggg caa ggg gag tcg ggg gga ggg tcc ttg ggg gca         2625
Leu Leu Leu Glu Gly Gln Gly Glu Ser Gly Gly Gly Ser Leu Gly Ala
805                 810                 815                 820 cag ccc ctc ctg cag ccc tcc cac tat ggg caa tct ggg atc tca atg         2673
Gln Pro Leu Leu Gln Pro Ser His Tyr Gly Gln Ser Gly Ile Ser Met
            825                 830                 835 tcc cac atg gac cta agg gcc aac ccc agt tgg tga tcccagctgg              2719
```

Ser His Met Asp Leu Arg Ala Asn Pro Ser Trp
                840                 845 agggagaacc caaagagaca gctcttctac tacccccaca gacctgctct ggacacttgc    2779
tcatgccctg ccaagcagca gatggggagg gtgccctcct atccccacct actcctgggt    2839
caggaggaaa agactaacag gagaatgcac agtgggtgga gccaatccac tccttccttt    2899
ctatcattcc cctgcccacc tccttccagc actgactgga agggaagttc aggctctgag    2959
acacgcccca acatgcctgc acctgcagcg cgcacacgca cgcacacaca catacagagc    3019
tctctgaggg tgatggggct gagcagg                                        3046

<210> SEQ ID NO 5
<211> LENGTH: 18
<212> TYPE: DNA
<213> ORGANISM: Artificial Sequence
<220> FEATURE:
<223> OTHER INFORMATION: PCR Primer

<400> SEQUENCE: 5
ccaaacgctg tctccgga                                                    18

<210> SEQ ID NO 6
<211> LENGTH: 27
<212> TYPE: DNA
<213> ORGANISM: Artificial Sequence
<220> FEATURE:
<223> OTHER INFORMATION: PCR Primer

<400> SEQUENCE: 6
gctagtaacg tactgtttgc tgatgaa                                          27

<210> SEQ ID NO 7
<211> LENGTH: 27
<212> TYPE: DNA
<213> ORGANISM: Artificial Sequence
<220> FEATURE:
<223> OTHER INFORMATION: PCR Probe

<400> SEQUENCE: 7
ctactggtct gaccggctga tcattgg                                          27

<210> SEQ ID NO 8
<211> LENGTH: 19
<212> TYPE: DNA
<213> ORGANISM: Artificial Sequence
<220> FEATURE:
<223> OTHER INFORMATION: PCR Primer

<400> SEQUENCE: 8
gaaggtgaag gtcggagtc                                                   19

<210> SEQ ID NO 9
<211> LENGTH: 20
<212> TYPE: DNA
<213> ORGANISM: Artificial Sequence
<220> FEATURE:
<223> OTHER INFORMATION: PCR Primer

<400> SEQUENCE: 9
gaagatggtg atgggatttc                                                  20

<210> SEQ ID NO 10
<211> LENGTH: 20
<212> TYPE: DNA
<213> ORGANISM: Artificial Sequence -continued

```
<220> FEATURE:
<223> OTHER INFORMATION: PCR Probe

<400> SEQUENCE: 10
caagcttccc gttctcagcc                                              20

<210> SEQ ID NO 11
<211> LENGTH: 3971
<212> TYPE: DNA
<213> ORGANISM: H. sapiens
<220> FEATURE:
<221> NAME/KEY: CDS
<222> LOCATION: (281)...(2320)

<400> SEQUENCE: 11
ggcacgaggc cggaaacagc gggctggggc agccactgct tacactgaag agggaggacg    60
ggagaggagt gtgtgtgtgt gtgtgtgtgt gtgtgtgtat gtatgtgtgt gctttatctt   120
attttctttt ttggtggtgg tggtggaagg ggggaggtgc tagcagggcc agccttgaac   180
tcgctggaca gagctacaga cctatggggc ctggaagtgc ccgctgagaa agggagaaga   240
cagcagaggg gttgccgagg caacctccaa gtcccagatc atg tct ctg tgg ggt    295
                                              Met Ser Leu Trp Gly
                                                1               5 ctg gtc tcc aag atg ccc cca gaa aaa gtg cag cgg ctc tat gtc gac   343
Leu Val Ser Lys Met Pro Pro Glu Lys Val Gln Arg Leu Tyr Val Asp
             10                  15                  20 ttt ccc caa cac ctg cgg cat ctt ctg ggt gac tgg ctg gag agc cag   391
Phe Pro Gln His Leu Arg His Leu Leu Gly Asp Trp Leu Glu Ser Gln
         25                  30                  35 ccc tgg gag ttc ctg gtc ggc tcc gac gcc ttc tgc tgc aac ttg gct   439
Pro Trp Glu Phe Leu Val Gly Ser Asp Ala Phe Cys Cys Asn Leu Ala
     40                  45                  50 agt gcc cta ctt tca gac act gtc cag cac ctt cag gcc tcg gtg gga   487
Ser Ala Leu Leu Ser Asp Thr Val Gln His Leu Gln Ala Ser Val Gly
 55                  60                  65 gag cag ggg gag ggg agc acc atc ttg caa cac atc agc acc ctt gag   535
Glu Gln Gly Glu Gly Ser Thr Ile Leu Gln His Ile Ser Thr Leu Glu
 70                  75                  80                  85 agc ata tat cag agg gac ccc ctg aag ctg gtg gcc act ttc aga caa   583
Ser Ile Tyr Gln Arg Asp Pro Leu Lys Leu Val Ala Thr Phe Arg Gln
                 90                  95                 100 ata ctt caa gga gag aaa aaa gct gtt atg gaa cag ttc cgc cac ttg   631
Ile Leu Gln Gly Glu Lys Lys Ala Val Met Glu Gln Phe Arg His Leu
             105                 110                 115 cca atg cct ttc cac tgg aag cag gaa gaa ctc aag ttt aag aca ggc   679
Pro Met Pro Phe His Trp Lys Gln Glu Glu Leu Lys Phe Lys Thr Gly
         120                 125                 130 ttg cgg agg ctg cag cac cga gta ggg gag atc cac ctt ctc cga gaa   727
Leu Arg Arg Leu Gln His Arg Val Gly Glu Ile His Leu Leu Arg Glu
     135                 140                 145 gcc ctg cag aag ggg gct gag gct ggc caa gtg tct ctg cac agc ttg   775
Ala Leu Gln Lys Gly Ala Glu Ala Gly Gln Val Ser Leu His Ser Leu
150                 155                 160                 165 ata gaa act cct gct aat ggg act ggg cca agt gag gcc ctg gcc atg   823
Ile Glu Thr Pro Ala Asn Gly Thr Gly Pro Ser Glu Ala Leu Ala Met
                 170                 175                 180 cta ctg cag gag acc act gga gag cta gag gca gcc aaa gcc cta gtg   871
Leu Leu Gln Glu Thr Thr Gly Glu Leu Glu Ala Ala Lys Ala Leu Val
             185                 190                 195 ctg aag agg atc cag att tgg aaa cgg cag cag cag ctg gca ggg aat   919
Leu Lys Arg Ile Gln Ile Trp Lys Arg Gln Gln Gln Leu Ala Gly Asn
```

```
                    200                 205                 210
ggc gca ccg ttt gag gag agc ctg gcc cca ctc cag gag agg tgt gaa      967
Gly Ala Pro Phe Glu Glu Ser Leu Ala Pro Leu Gln Glu Arg Cys Glu
    215                 220                 225 agc ctg gtg gac att tat tcc cag cta cag cag gag gta ggg gcg gct     1015
Ser Leu Val Asp Ile Tyr Ser Gln Leu Gln Gln Glu Val Gly Ala Ala
230                 235                 240                 245 ggt ggg gag ctt gag ccc aag acc cgg gca tcg ctg act ggc cgg ctg     1063
Gly Gly Glu Leu Glu Pro Lys Thr Arg Ala Ser Leu Thr Gly Arg Leu
                250                 255                 260 gat gaa gtc ctg aga acc ctc gtc acc agt tgc ttc ctg gtg gag aag     1111
Asp Glu Val Leu Arg Thr Leu Val Thr Ser Cys Phe Leu Val Glu Lys
            265                 270                 275 cag ccc ccc cag gta ctg aag act cag acc aag ttc cag gct gga gtt     1159
Gln Pro Pro Gln Val Leu Lys Thr Gln Thr Lys Phe Gln Ala Gly Val
        280                 285                 290 cga ttc ctg ttg ggc ttg agg ttc ctg ggg gcc cca gcc aag cct ccg     1207
Arg Phe Leu Leu Gly Leu Arg Phe Leu Gly Ala Pro Ala Lys Pro Pro
    295                 300                 305 ctg gtc agg gcc gac atg gtg aca gag aag cag gcg cgg gag ctg agt     1255
Leu Val Arg Ala Asp Met Val Thr Glu Lys Gln Ala Arg Glu Leu Ser
310                 315                 320                 325 gtg cct cag ggt cct ggg gct gga gca gaa agc act gga gaa atc atc     1303
Val Pro Gln Gly Pro Gly Ala Gly Ala Glu Ser Thr Gly Glu Ile Ile
                330                 335                 340 aac aac act gtg ccc ttg gag aac agc att cct ggg aac tgc tgc tct     1351
Asn Asn Thr Val Pro Leu Glu Asn Ser Ile Pro Gly Asn Cys Cys Ser
            345                 350                 355 gcc ctg ttc aag aac ctg ctt ctc aag aag atc aag cgg tgt gag cgg     1399
Ala Leu Phe Lys Asn Leu Leu Leu Lys Lys Ile Lys Arg Cys Glu Arg
        360                 365                 370 aag ggc act gag tct gtc aca gag gag aag tgc gct gtg ctc ttc tct     1447
Lys Gly Thr Glu Ser Val Thr Glu Glu Lys Cys Ala Val Leu Phe Ser
    375                 380                 385 gcc agc ttc aca ctt ggc ccc ggc aaa ctc ccc atc cag ctc cag gcc     1495
Ala Ser Phe Thr Leu Gly Pro Gly Lys Leu Pro Ile Gln Leu Gln Ala
390                 395                 400                 405 ctg tct ctg ccc ctg gtg gtc atc gtc cat ggc aac caa gac aac aat     1543
Leu Ser Leu Pro Leu Val Val Ile Val His Gly Asn Gln Asp Asn Asn
                410                 415                 420 gcc aaa gcc act atc ctg tgg tac aat gcc ttc tct gag atg gac cgc     1591
Ala Lys Ala Thr Ile Leu Trp Tyr Asn Ala Phe Ser Glu Met Asp Arg
            425                 430                 435 gtg ccc ttt gtg gtg gct gag cgg gtg ccc tgg gag aag atg tgt gaa     1639
Val Pro Phe Val Val Ala Glu Arg Val Pro Trp Glu Lys Met Cys Glu
        440                 445                 450 act ctg aac ctg aag ttc atg gct gag gtg ggg acc aac cgg ggg ctg     1687
Thr Leu Asn Leu Lys Phe Met Ala Glu Val Gly Thr Asn Arg Gly Leu
    455                 460                 465 ctc cca gag cac ttc ctc ttc ctg gcc cag aag atc ttc aat gac aac     1735
Leu Pro Glu His Phe Leu Phe Leu Ala Gln Lys Ile Phe Asn Asp Asn
470                 475                 480                 485 agc ctc agt atg gag gcc ttc cag cac cgt tct gtg tcc tgg tcg cag     1783
Ser Leu Ser Met Glu Ala Phe Gln His Arg Ser Val Ser Trp Ser Gln
                490                 495                 500 ttc aac aag gag atc ctg ctg ggc cgt ggc ttc acc ttt tgg cag tgg     1831
Phe Asn Lys Glu Ile Leu Leu Gly Arg Gly Phe Thr Phe Trp Gln Trp
            505                 510                 515 ttt gat ggt gtc ctg gac ctc acc aaa cgc tgt ctc cgg agc tac tgg     1879
Phe Asp Gly Val Leu Asp Leu Thr Lys Arg Cys Leu Arg Ser Tyr Trp
```

-continued

```
              520                 525                 530
tct gac cgg ctg atc att ggc ttc atc agc aaa cag tac gtt act agc     1927
Ser Asp Arg Leu Ile Ile Gly Phe Ile Ser Lys Gln Tyr Val Thr Ser
535                 540                 545 ctt ctt ctc aat gag ccc gac gga acc ttt ctc ctc cgc ttc agc gac     1975
Leu Leu Leu Asn Glu Pro Asp Gly Thr Phe Leu Leu Arg Phe Ser Asp
550                 555                 560                 565 tca gag att ggg ggc atc acc att gcc cat gtc atc cgg ggc cag gat     2023
Ser Glu Ile Gly Gly Ile Thr Ile Ala His Val Ile Arg Gly Gln Asp
                570                 575                 580 ggc tct cca cag ata gag aac atc cag cca ttc tct gcc aaa gac ctg     2071
Gly Ser Pro Gln Ile Glu Asn Ile Gln Pro Phe Ser Ala Lys Asp Leu
            585                 590                 595 tcc att cgc tca ctg ggg gac cga atc cgg gat ctt gct cag ctc aaa     2119
Ser Ile Arg Ser Leu Gly Asp Arg Ile Arg Asp Leu Ala Gln Leu Lys
        600                 605                 610 aat ctc tat ccc aag aag ccc aag gat gag gct ttc cgg agc cac tac     2167
Asn Leu Tyr Pro Lys Lys Pro Lys Asp Glu Ala Phe Arg Ser His Tyr
    615                 620                 625 aag cct gaa cag atg ggt aag gat ggc agg ggt tat gtc cca gct acc     2215
Lys Pro Glu Gln Met Gly Lys Asp Gly Arg Gly Tyr Val Pro Ala Thr
630                 635                 640                 645 atc aag atg acc gtg gaa agg gac caa cca ctt cct acc cca gag ctc     2263
Ile Lys Met Thr Val Glu Arg Asp Gln Pro Leu Pro Thr Pro Glu Leu
                650                 655                 660 cag atg cct acc atg gtg cct tct tat gac ctt gga atg gcc ctg att     2311
Gln Met Pro Thr Met Val Pro Ser Tyr Asp Leu Gly Met Ala Leu Ile
            665                 670                 675 cct cca tga gcatgcagct tgggccagat atggtgcccc aggtgtaccc accacactct   2370
Pro Pro cactccatcc ccccgtatca aggcctctcc ccagaagaat cagtcaacgt gttgtcagcc     2430
ttccaggagc ctcacctgca gatgcccccc agcctgggcc agatgagcct gccctttgac     2490
cagcctcacc cccagggcct gctgccgtgc agcctcagg agcatgctgt gtccagccct     2550
gaccccctgc tctgctcaga tgtgaccatg gtggaagaca gctgcctgag ccagccagtg     2610
acagcgtttc ctcagggcac ttggattggt gaagacatat ccctcctct gctgcctccc     2670 actgaacagg acctcactaa gcttctcctg gaggggcaag gggagtcggg gggagggtcc     2730
ttgggggcac agcccctcct gcagccctcc cactatgggc aatctgggat ctcaatgtcc     2790
cacatggacc taagggccaa ccccagttgg tgatcccagc tggagggaga acccaaagag     2850
acagctcttc tactaccccc acagacctgc tctggacact tgctcatgcc ctgccaagca     2910
gcagatgggg agggtgccct cctatcccca cctactcctg ggtcaggagg aaaagactaa     2970
caggagaatg cacagtgggt ggagccaatc cactccttcc tttctatcat tccctgccc      3030 acctccttcc agcactgact ggaagggaag ttcaggctct gagacacgcc ccaacatgcc     3090
tgcacctgca gcgcgcacac gcacgcacac acacatacag agctctctga gggtgatggg     3150
gctgagcagg agggggctg ggtaagagca caggttaggg catggaaggc ttctccgccc      3210
attctgaccc agggcctagg acggataggc aggaacatac agacacattt acactagagg     3270
ccagggatag aggatattgg gtctcagccc taggggaatg ggaagcagct caagggaccc     3330
tgggtgggag cataggaggg gtctggacat gtggttacta gtacaggttt tgccctgatt     3390
aaaaaatctc ccaaagcccc aaattcctgt tagccaggtg gaggcttctg atacgtgtat     3450
gagactatgc aaaagtacaa gggctgagat tcttcgtgta tagctgtgtg aacgtgtatg     3510
tacctaggat atgttaaatg tatagctggc accttagttg catgaccaca tagaacatgt     3570
```

| | |
|---|---|
| gtctatctgc ttttgcctac gtgacaacac aaatttggga gggtgagaca ctgcacagaa | 3630 |
| gacagcagca agtgtgctgg cctctctgac atatgctaac ccccaaatac tctgaatttg | 3690 |
| gagtctgact gtgcccaagt gggtccaagt ggctgtgaca tctacgtatg gctccacacc | 3750 |
| tccaatgctg cctgggagcc agggtgagag tctgggtcca ggcctggcca tgtggccctc | 3810 |
| cagtgtatga gagggccctg cctgctgcat ctttctgtt gccccatcca ccgccagctt | 3870 |
| cccttcactc ccctatccca ttctccctct caaggcaggg gtcatagatc ctaagccata | 3930 |
| aaataaattt tattccaaaa taaaaaaaaa aaaaaaaaaa a | 3971 |

<210> SEQ ID NO 12
<211> LENGTH: 16500
<212> TYPE: DNA
<213> ORGANISM: H. sapiens

<400> SEQUENCE: 12

| | |
|---|---|
| tcccccaag cctggctcca aggcctggac cccagtcctg atccccacg tgttccccca | 60 |
| ctcggcacag gaggcacaca tattcacccc actttcttcc tcttcctcct ccagcccact | 120 |
| ttctcttctc tgtgtcgtca gagctccagg gagggacctg ggtagaagga gaagccggaa | 180 |
| acagcgggct ggggcagcca ctgcttacac tgaagaggga ggacgggaga ggagtgtgtg | 240 |
| tgtgtgtgtg tgtgtgtgta tgtatgtgtg tgctttatct tattttctt tttggtggtg | 300 |
| gtggtggaag gggggaggtg ctagcagggc cagccttgaa ctcgctggac agagctacag | 360 |
| acctatgggg cctggaagtg cccgctgaga aaggagaag acagcagagg ggttgccgag | 420 |
| gtgaggggtt gcctccgagg tgggtgcggg ggcctctatg agtgcatggg ggtggattcg | 480 |
| tgggggagc tctcgggatc ctcccctggc tgggtggatg gtcccccaaga gatggtttca | 540 |
| gctagtgttg gtggctggtg gcactgggtt ttagcagttt cgaactcctg gaggaatctg | 600 |
| ggagggtcca ggcctcagta ctcccctccc ccatgggtca cgttttcaca gcctcacccc | 660 |
| tgcaccccca gggccatgga aagtcaggga aaggaggtga aggagtgccc ctctgccctg | 720 |
| agtcggggga agtggccgcc cctccctgga aggttgatgc cagagggcag tggatccttg | 780 |
| ttaaacccct atcctgccct ccactaaagg ttcctgttca agggtgtggc tggggcgtga | 840 |
| gcaagcccca gatgtagacc tcatggtggc ccagacgagg gggaatttcc ccctcaaaac | 900 |
| tgctccacgc ttggctgctg tagacgctga gatttcccag cggcggcgcc gagttaaccc | 960 |
| tcctcgtgct gaactggctc cacctccccg cctgccccca ccgccacatt cacgcattgg | 1020 |
| gcaactcaga gaagctgttt taactttcga tcctgtggtc ccacaatcag aggactcggg | 1080 |
| cagataggg ttgagataag cgagtttagg ccaccaagcg ggcggacgag gatcccagac | 1140 |
| cttgcgcttc ccttctgagt ttgggaggta acactggccc cgcccctcac gccgtggctc | 1200 |
| ctccctccct tccccttcaa ggggctgaag acaaaaggtg ccctgtcct ggtcaagcca | 1260 |
| atcgacccag cctgttatg ggttggggtg gggagaaatg tgtcctcctg atggctgggg | 1320 |
| aagaagaggg gttggatatt tctagccagg gccatgccag gaggctggtc actctgcaag | 1380 |
| gggatgcaga ggaaagcggt gcccactcac tccagggac ctttctctct tgggctagag | 1440 |
| aaaggcctat tggaggaacc tgagcaggag gggtaaggat tctgccttga ggagaaaaga | 1500 |
| gctggggtaa gtgggcactg gaggaaaagag gggcatgaag gtcttggagc agaaacatcc | 1560 |
| agagaaggga cctctccatt ttccatccct ctgagaggcc tgggagaggt gagaggctga | 1620 |
| acgtgcaaca ggaggacttg gggttactgg gtttggggag acctgggag ttgtcatccc | 1680 |
| atcctctccc tcatctctgg gagagggata ttatgagaaa cgtgaactga gaggcccctg | 1740 |

```
ggaaaccact ggttacccag tcctccctga acctggaaat ggggatgcaa cccctcttc    1800 tacttccctg tccctcctc tcctttctac ctgttttcgt ctctcatctt tgccttctag    1860
ccctccagct tcctctctct tctaggctct ttcctcctag cttactaaac ccgccttttt   1920
tccagtctct tccatcctct tccttagttc tctctacttt ccttttccac ctctcctcct   1980
tcaagtctcc tcccaccttc ccccacttct taggatgatc agatttgccc ctggaaggga   2040
tcctaacaac acagtgcgat ggttaatccc cactcagatt caaagcctgc tttccaaact   2100
cacttactga gtggccttgg gcagagtaga gaaactcctt aagcctcagt tcttcatct    2160 ataaaatggg atattatata ttttaaaaag tgtcgtgagg cctgaaggag ataatacact   2220
gagtgtaatg cctcatacac agtaagtgct taacaaatag tagctgttat tactctccca   2280
tcctcttcat catctagcct tgtggttttc attttatttt tatttcattt atttatttat   2340
ttattttgag acagagtctc tctctgtcgc ccaggctgga gtgcagtggc tcgatctctg   2400
ctcactgcaa gctccgcccc ccaggttcac gccattctgt cacctcagcc tccccagtag   2460
ctgggactac aggcgctcgc caccacgccc tgctaatttt gttttgtat ttttagtaga    2520 gatggggttt cactgtgtta gccaggatgg tcttgatctc ctgacctcgt gatctgcccg   2580
cctcggcctc ccaaagcgct gggattacag gcatgagcca ctgcgcctgg ccgagccttg   2640
tggttttcaa attatctcat ggagtcctag aattttgaga ggtttgtcta gggatgcctt   2700
tggcgtcagg aggtggggag agggaagtag aagcagtcga gtttcaggct ttccatgctt   2760
gctttcaaca gggcatcttc ggtttcgtac cttttatgta attgagattc cacagattaa   2820
aagctgacat tgcctaccgc tttaaaaagt ttggaaagtt ttccactcat ctaacactca   2880
tattttatag atgagaagat cgaagcccac aaagggaagg ctctttgccc acagaaccag   2940
agccaggtct agagctgcaa ctaaatcctc tgccactcta agagagctct cgctctactg   3000
ccctgtctcc ctttgcctcc ccatccctct ggctacagct cagctcttcc caccctgtg    3060 tctatcactg aaggagttac ccccatctca ggcattgact caggatgccc ctggtttaag   3120
gtggtctggc catgagtggt ggtggggaca gtccctagga gggctatcta tgggaggtcc   3180
ctggctgccc caggagatag gccaagtttc ttgggcaccc ctcagagtgg ccttattttt   3240
ctcctccagg caacctccaa gtcccagatc atgtctctgt ggggtctggt ctccaagatg   3300
cccccagaaa aagtgcagcg gctctatgtc gactttcccc aacacctgcg gcatcttctg   3360
ggtgactggc tggagagcca gccctggtga gtcctggctg ctccctgctg gtcccccaag   3420
tcttccctaa ctcatcttcc ttctccttag atttttctcc cctcacccat ggattcagaa   3480
cttgagacct gttattccat gtgtagtgac ctagatttag cagggagtct gtgcccatc    3540 aagaccaggc tatgaatgtt gacagatgga gaccccatct cttaggaggc tgagccgaag   3600 aggaggggg tttgggctgg gacaaaggca cttctcataa cagctagaag actgggaaac    3660
aaggcgcatg ggtgaaagct acagagggcc tagatggaga ataaggagcg agaaaggaac   3720
tgctgagctt ttggctgtgg ggtaaagggt caggagagct gaggaagccc tggcctgagg   3780
tagcctcatc ctgatcttcc tgcagggagt tcctggtcgg ctccgacgcc ttctgctgca   3840
acttggctag tgccctactt tcagacactg tccagcacct tcaggcctcg gtgggagagc   3900
aggggagggg gagcaccatc ttgcaacaca tcagcaccct tgaggtgggg caggagggga   3960
ggggacaagg ctgggtgggg ctgaggttga actgggttga gcattgggcc ctggaagaaa   4020
attggttgga tgctggaagc aaattggtgt tcctgtggtt aactgctagc tagcaggcaa   4080
attagatttt aaaagcatgc aaatgcacaa aaacttctgg agtctacagt tgtgcttcct   4140
```

```
tatagtatat gtgtgaatgc aggcctgggg attggaggga ttgaaggaca tgggtaagag    4200
caaagctcac tgtttaccac cctcatttct gtagagcata tatcagaggg acccctgaa    4260 gctggtggcc actttcagac aaatacttca aggagagaaa aaagctgtta tggaacaggt    4320
attgtgatat tccacctccc accccaactc aatcccctga actttggcc tgagccatga    4380 caaactagaa agaatttgaa cctcagtaaa ggctcagtgt tctaggccca ggaatgacca    4440
aaggaggttc ctagggtcag agtgaacccc aagtcaagct cagggaatct ttctatgagg    4500
gactgaaggt aagaggccgg ggagaacaga gcaagggata aggagctgat tctgctagga    4560
gcaaggtctt atctccacga tattccaaaa ggtcaggaag aactgccaaa ggggagaggg    4620
gaacaagaaa acgctatctg cagagcagag agtggaggcc aggtatagag ggatgagcag    4680 agtgttcac ttcttggcat ctgtccttcc tgtgtagttc cgccacttgc caatgccttt    4740
ccactggaag caggaagaac tcaagtttaa acaggcttg cggaggctgc agcaccgagt    4800
aggggagatc caccttctcc gagaagccct gcagaagggg gctgaggctg ccaaggtgg    4860 gggccagggt ggttctgggg agtgtgtagg agtggttgcc tcttggatct caaccttatc    4920
tgaacctcta atctgtctgc acccttgatt tctgccccca accctcagtg tctctgcaca    4980
gcttgataga aactcctgct aatgggactg ggccaagtga ggtgagtaat gggctgacag    5040
gtggagacct tggtcaaagt gcagctggag ggatggaagc tagacctcag aaagacacag    5100
gctgaagtag ggcaagggaa tgccagagga gtgagaaaaa gagccgtatc ccaggagctg    5160
ggtgtggagg cagcgtgagg ccctggctca ggccctctc tgcccatagg ccctggccat    5220
gctactgcag gagaccactg gagagctaga ggcagccaaa gccctagtgc tgaagaggat    5280
ccagatttgg aaacggcagc agcagctggc agggaatggc gcaccgtttg aggagagcct    5340
ggccccactc caggagaggt tgggctaggg ctgatgggga agagggggca agctggggt    5400 gggcagctga ccctgctgaa ggccctacag gtgagagaaa gaagccaggc gggagggcct    5460
tggagtggac caagatgcat aaaagccagt tccagcgggg ctgtgcacac tgtcgttcag    5520
gtcgcatcct gtacaagtgg gcctagtgga ggggcacaag cggggactca tccaacccag    5580
gcttctctcc tcaagcccca tgcctagagg aataggaggg cttttccatt tggtttattg    5640
ggtgggaaca ctttccaatt tgccacaaag cactgtaagt ggtggcagtt gtcctgggtg    5700
caagagccgt cggggagag gcagctgggt ttccacaggg ggtgtaggca ctgagaatga    5760
acctcccacc cagaccctag gccaacagat cacagaaccc ccttcagccc aggtgccttg    5820
cagccacacc cactacccac cccacttctc cacacatgat agccttctc cctgggtata    5880 ggggaagggg gtctgggccg gagcaagcag ccttaatcct gtgccccctg accactgtcc    5940
tggccccagg tgtgaaagcc tggtggacat ttattcccag ctacagcagg aggtaggggc    6000
ggctggtggg gagcttgagc ccaagacccg ggcatcgctg actggccggc tggatgaagt    6060
cctgagaacc ctcgtcacca ggtattcccc gggagctccc agtctggcct agaacagacc    6120
tcgggaagaa aagaagggg ctagagctgt ggggagggca ccagcaggga cctagccccc    6180
aactcccctt gtgtcctcct cactcccagt tgcttcctgg tggagaagca gccccccag    6240 gtactgaaga ctcagaccaa gttccaggct ggagttcgat tcctgttggg cttgaggttc    6300 ctggggggccc cagccaagcc tccgctggtc agggccgaca tggtgacaga gaagcaggcg    6360
cgggagctga gtgtgcctca gggtcctggg gctggagcgt aagctgggat tggacctggg    6420
gttggagaag ggctgttagg gtgatggagg cagcctggag ggctggcact gaaaagagca    6480
agggatgggg agggaggggcc atgggatgtg gagaccctga atggtcaagg cagaggaaag    6540
```

```
ggagggaccc atttagggct ggaatggggt gggggcatca tgatttggcc aagatgggga      6600 ctcctcccett aagaacccaa acagagacat ggagatttag ggctggtgac agtgggtagt      6660
ctacactcac ccatgcactc gccacacctg acgacagtga gatgagctcg ttcacactct      6720
gacctcccct ggcagagaaa gcactggaga aatcatcaac aacactgtgc ccttggagaa      6780
cagcattcct gggaactgct gctctgccct gttcaagaac ctggtgaggg gctttggggt      6840
gcagtgaggg gggcaccact aggagactgt gggactctcc ttggagagga tgtcaggaag      6900
cccaggagga gcggtctctg tcctcatgac ctcgcccttg ctctccctca ccccacccac      6960
agcttctcaa gaagatcaag cggtgtgagc ggaagggcac tgagtctgtc acagaggaga      7020
agtgcgctgt gctcttctct gccagcttca cacttggccc cggcaaactc cccatccagc      7080
tccaggtgaa ccgtggccca gccctgcccc aatctggacc cccgagtcct cctccaatgc      7140
cacacacaag ggccctggac cctcacctct tgtgactgcc ccatacccca tgtgtctggg      7200
attcatgcac actggggccc gggtgagtgg gggtgagcaa gagcatggag tgcacagggc      7260
agggaatggt agtggatagc agcaaacact tcggaagcac ttcctataga ccagggcact      7320
ctattaaatg atacatacgc acatgcgtgc cagcacacac acgtctggtt ttcacaataa      7380
cattatgagg taggcagtat tatcagcctc attttataga taaggacatt gagacagaga      7440
gtttaagtag tttgtcccag tcacacagct aagtgttgga gctggtattt gaaacctgga      7500
ggtctggttc catagcgatg actaataacc acttctctac ggtgaggccc tgattgagct      7560
tcagaacgca tttaataaca tggcatgagc tttttgatta tgatgtgtga gtccaataac      7620
ttctctgagt gctcagagcc agtccctga ggaaacttct tgcttcacta agaaacccct      7680
gtccggctgg gcatggtggc tcaagcctgt aatcccagca ctttgggagg ccgaggtggg      7740
tagatcacaa ggtcaggagt tcaagaccag cctggccaat atggtgaaac cccgtctcca      7800
ctaaaaatac aaaaattagc tgggcgtggt ggtgcaggcc tgtagtccca gctgctcggg      7860
aggctaagca ggagaatcgc ttgaacccag gaggcggagg ttgcagtgag ccaagattgc      7920
gccactgccc ttcagcctgg gcgacagagc aagactatgt ctcaaaaaca aaacaaaaca      7980
actcagcact ttgggaggcc aaggtaggag gatcgcttga gcctgcaagt ttaagaccag      8040
cctgggctac atagggagat ccaatctcta caaaaaataa aaaattggcc gggcatggtg      8100
gctcacgcct gtaatcccag cactttggga ggccaaggcg ggcggatcat gaggtcagga      8160
aatcgagacc atcctggcta acacggtgaa acctcgtatc tactaaaaat acaaaaaatt      8220
agccaggcat ggtggcgggc gcctgagtcc cagctactcg ggaggctgaa gcaggagaat      8280
ggcgtgaacc tgggagggag agcttgcagt gagccaagat cgcgccgctg cactccagcc      8340
tgagtgacag agcgagactc tgtctcaaaa ataaataaat aataattag ctggattagg      8400 tggtacattt ctgtagttcc agctattcag gaggctgagg tggaaggatc acttgagccc      8460
tgaaggctga ggctgcagtg agctgagatt gcactactgc actccagcct gggcaacaga      8520
gtgagatact atctaaaaaa aaaaaaaaa aaaaaaagg aaagaaagaa agaaagaaa      8580 cccctgtcct caccctcttc aggccctgtc tctgccctg gtggtcatcg tccatggcaa      8640
ccaagacaac aatgccaaag ccactatcct gtgggacaat gccttctctg agatggtgag      8700
gaaagtcctg gagttggagg gaacaggggc agggtgggtt ctaacatggg cagtggtgca      8760
ggcctgctga tggggtggtg ggcatgttta aatgggtgtg accttaacac tttctcatgg      8820
gcctgctttc gtgcttctga cctcttttca ccccagtctt aacaactatc aggccacagc      8880
actgtaacct agaaaaaaca gcatgtttgt gagcgatatc aggggctgtg gagggtagg      8940
```

```
ccacaggcag gtgggaggga tgaaggccgg cccgaggaat aacaagacgg tagcctgcag    9000
tgctctcttc ttcccccttc tccccaggac cgcgtgccct ttgtggtggc tgagcgggtg    9060
ccctgggaga agatgtgtga aactctgaac ctgaagttca tggctgaggt ggggaccaac    9120
cgggggctgc tcccagagca cttcctcttc ctggcccaga agatcttcaa tgacaacagc    9180
ctcagtatgg aggccttcca gcaccgttct gtgtcctggt cgcagttcaa caaggtcatt    9240
ctcctgccct ttggacctcc cacccccaag ctcttcatcc ctggggcact cagggcctgc    9300
tcagcctcca tgcagggacc ttccactgga ttctccacag tgcccctca ggtcctttag     9360 gaaggcctgt catggaccag ggaggaaaaa ccccaggcct gggggttggc tctggagatg    9420
cgttctctga catccctgag gttttggtct gggggccatc tgtccttcct ctttaccagt    9480
gacttgcatg actcacccag gttgtgtgta acagagctc tgattcaaag tgactttgac     9540
ctgttggaaa aatagttcct ggccgggcac agcggctcat gcctgtaatc ccagtctttg    9600
acatgccggg gtgggtggat cacctgaggt caggagtttg agaccagcct ggccaacatg    9660
gtgaaactcc atctctacta aaaatacaaa aattagccag ttgcggtggc acatgcctgt    9720
aatcccagct acatgggagg ctgacgcagg agaattgctt gaacccagga ggtggaggtt    9780
gcagtgagct gagatcatac cactgcactc aagcctgggt gacagagcaa gactctgtct    9840
caaaaaaaaa aaaaaaaaaa ggccaggcat ggtggttcat gcctgtaatc ccagcacttt    9900
gggaggccga cacggataga tcacctgagg tcaggagttc gagaccagcc tggccaacat    9960
ggcaaaaccc cgtctctact aaaaacaaaa aatagccag gagtggtcgt ttgcgtctgt    10020
aatcccagct actcggctga ggcaggaggt gaacccagga ggtagaggct gcaggaaga    10080 tgaaaccatt gcactccagc ctgggcaaga ctctgtatca aaaaaaaaa aaaaaaggc    10140 taggtgtggt ggctcacacc tgtaatccca gcactttggg aggctgaggc gggcggatca    10200
caaggtcaag agatcgagac catcctgacc aacatggtga aacccgtct ctactaaaaa    10260 tacaaaaatt acctgggcat ggtggcgcat gcctgtagtc ccaactactc gggaggctga    10320
ggcaggagaa tcacttgaac ctgggaggca gaggttgcag cgagccaaga ttgtgccact    10380
gcactccagc ctgccaacag aatgagattc tgtctaaaaa aaaaagaaa gaaagaaaga    10440 agaaaaaga attcctgttg caaaaactga acaaaatccc acagggacat gtgcagtaat    10500
accagctacc acgtgttgac agcttatatg ccaggcgctg tgcttaacac cttatgtatg    10560
ttatctcact taatcctccc aacatctctt tgaggtagat actattatta tccccatttt    10620
acagatgagg aatctgatgc tcagagggtt atgtagtttg ttcaagttcc caaagcaggt    10680
gagtgccatg gctaggagag aaccacatat ttctgactct tgctctttta ttttatgtta    10740
tattatgtta ttttatgttt tggtttttt ttcttttctt tctttcttc tttctttctt      10800 tctttctctt tctttctttc tttctttctt tctttcttc tttctttctt tctctttctc      10860
tttctctctt tttctttctt ttgtgtgaga cagaatcttt aaagagaaga agaaatgct     10920 catgtgacca gagggtgtgt tagctaaagg gagcaagaca gtcacaccca gcaggttacc    10980
ttcctttggg cgtcacctct gccacacctc cttaggaga gggtgtagca tagtagttaa     11040
gaggggctcc agggccagaa tgcctgggtt taaatcctag ctctgcctct taccagctat    11100
gtagacctgg gcaagtcatt cgacgttttt ggacttccat ttcttcatct gtaagatgga    11160
attattataa tccctacttc catagcctgg taaagagcaa ataaatatat ggaaaggctt    11220
gaaatagtgt ctggcacgtg taagcattag gattggtcgt tgtcattgat ggagtctcag    11280
gttcggtctg atcctcagcc ctgtgattct gtcgtgaggg cactcacagc tcactgcctg    11340
```

```
ccctaaacag gctccagctc tggccctccc tcggctcaca cctttccccc tctccccta    11400 ggagatcctg ctgggccgtg gcttcacctt ttggcagtgg tttgatggtg tcctggacct    11460
caccaaacgc tgtctccgga gctactggtc tgaccggtga gtcccacccc tgggtagtct    11520
gagcagccat acaccagtca cctccatact cactgcccat gccccatcct ctccttcatc    11580
ccggccaggc tgatcattgg cttcatcagc aaacagtacg ttactagcct tcttctcaat    11640
gagcccgacg gaacctttct cctccgcttc agcgactcag agattggggg catcaccatt    11700
gcccatgtca tccggggcca ggatggtgag gccaccccag ccagtcctct gtctctgtgc    11760
ctgtgccctc tggggtttct tctgggaatg aaatgtcctg accttcctga tgccgatcct    11820
gatcttcagg aagttcttcc agcttctctt cttccttctg tggtctaaat gttccccttc    11880
tcactgtgag ctctgtggga acggagacta gtgggtctct ctccctcagg agccccaccc    11940
taggtcctct ctcccttgcc ttggtggagt gagaacaggt cttatggtag gggttgggga    12000
aggggaagaa agtccggaca gagggatctc agggtctcct tcctaccata ggctctccac    12060
agatagagaa catccagcca ttctctgcca aagacctgtc cattcgctca ctgggggacc    12120
gaatccggga tcttgctcag ctcaaaaatc tctatcccaa gaagcccaag gatgaggctt    12180
tccggagcca ctacaagcgt gagctggaac tggcagctct gattccttcc tgtcacccac    12240
ttcctccctg ctccccgctg ccctcctctc cctgccgtg tgtcatcctg atgtcactcc    12300
ctatttcata gctgtgcttc tcttacttcc ccatgatcca tgcccacctt tccacctcc    12360 cttcctccct aaccccagag cactccatgg ctgtctttc cttctcacaa cagctgaaca    12420
gatgggtaag gatggcaggg gttatgtccc agctaccatc aagatgaccg tggaaaggtg    12480
agtgtggtgg tatggacagt gggtaggtca ggggcttagt gcttatctgc aggaaggagg    12540
ggtggcatca cccttggtc agtcacatgt acctccttcc ctcctccagg gaccaaccac    12600
ttcctacccc agagctccag atgcctacca tggtgccttc ttatgacctt ggaatggccc    12660
ctgattcctc catgagcatg cagcttggcc cagatatggt gtaaggagct ggaaagacag    12720
gaatgggagt ggtctgtgca gatgggctaa tcttagcatg ggcagctggg agagctggca    12780
ctgggggctg aacagggaat cttcctttcc atgagaggga cacctgttca aaagcagggt    12840
gtggtggtgt ccaggagaag ggctggcatc aggggtctg ttttctttcc ccaggccca    12900 ggtgtaccca ccacactctc actccatccc cccgtatcaa ggcctctccc cagaagaatc    12960
agtcaacgtg ttgtcagcct tccaggagta agtgaaaaac ctcatgggga taccatccca    13020
ctctaagggg gtgggcattt gaattgttag aagaggctct tctgtgagaa aggagcagca    13080
aatgctaaca gcctgtcttc ttctcttctg tccactctaa tgagggggta gtagttaaga    13140
tctggactgc ctaggtttga attctagctc caccacttac tggtttgggg caaattactt    13200
agcctttggt gccttatctg cacaatgggg gataataatg ctaataataa taacctacct    13260
cactgcatta ttgtggagat taaatgagtt cataacactt aaaaagctga gcatagtgca    13320
tggctcatag caaaagctgt gtaagtccag tcgtggatca cttaatgaag gagcattttc    13380
tgtctttggc agtttcataa ttatgcgaat accattgagt ataattacac aaacctagat    13440
ggtatagact actatacact gaggctatat tgtgtagcct attgatccta gctttaaacc    13500
cgagcagcat gatactgttc tgaatagtat aaggaaatag taacataatg gtaaatattt    13560
gtgtgatagg aattttcagc ttgattataa tttttttttt ttgagacagg gtctcactca    13620
ctggagtgca gtggtgcgat cttagctccc tgcaacctcc gcctcttggg ctcgagcaat    13680
cctcctgctg tagtgcacca cgacactcgg ctaattcttt tttaagattt ttctgcagac    13740
```

```
aaggtctcac ttactgccca agctggtctc aaactcctgg gcttaagtga tcctcccacc   13800
tcggcctccc aaagcgttag gattacaggc gtgagtcact ctgcctggcc ttgattataa   13860
tcttatggga ccactgtggt ctgtagttga cagaaatgtc gttaatgtgg tgcatgactg   13920
ttattattat tttctgtcct gccctgaga gccactgtca cttctctgct gtattggttt    13980
ttgtttactc atctgttttg gccttgaaat ggcctagaca ttttcttcc cgaagtatga    14040 cactcgggtg cttattaact tagtcaagac acaacatctc ccttcccaga aggtgaggcg   14100
ggagtgagga cttggggact taagaactac caaagttcag agtccaaaga aacattagaa   14160
attggctaat ccacccccat aacacgcaca ttttacagat gagaagactg agctcagagc   14220
atagaaatag cttgcccagg ccatgactaa gtcaggataa ggagctggag cttgtttcct   14280
cactcagtgg tcctgacttt gcaccactct gcatttgcct agcctgcctt cctctaactg   14340
tgctctccct acttccaggc ctcacctgca gatgccccccagcctgggcc agatgagcct    14400 gcccctttgac cagcctcacc cccagtgagt gacaaagccc ctcctgaccc catgtgcctc   14460
ttctttcctg gccttgcccc gctctcctta tttccattgc tggttcctgg caggggcctg   14520
ctgccgtgcc agcctcagga gcatgctgtg tccagccctg accccctgct ctgctcagat   14580
gtgaccatgg tggaagacag ctgcctgagc cagccagtga cagcgtttcc tcagggcact   14640
tggtgagtgg cagcttggga gtggaggctg ggtggcatct aggggagtgg gcgccatgcc   14700
tactccactg cttctcccat ctccttgcag gattggtgaa gacatattcc ctcctctgct   14760
gcctcccact gaacaggacc tcactaagct tctcctggag gggcaagggg agtcgggggg   14820
agggtccttg ggggcacagc ccctcctgca gccctccac tatgggcaat ctgggatctc    14880
aatgtcccac atggacctaa gggccaaccc cagttggtga tcccagctgg agggagaacc   14940
caaagagaca gctcttctac tacccccaca gacctgctct ggacacttgc tcatgccctg   15000
ccaagcagca gatggggagg gtgccctcct atccccacct actcctgggt caggaggaaa   15060
agactaacag gagaatgcac agtgggtgga gccaatccac tccttccttt ctatcattcc   15120
cctgcccacc tccttccagc actgactgga agggaagttc aggctctgag acacgcccca   15180
acatgcctgc acctgcagcg cgcacacgca cgcacacaca catacagagc tctctgaggg   15240
tgatggggct gagcaggagg ggggctgggt aagagcacag gttagggcat ggaaggcttc   15300
tccgcccatt ctgacccagg gcctaggacg gataggcagg aacatacaga cacatttaca   15360
ctagaggcca gggatagagg atattgggtc tcagccctag gggaatggga agcagctcaa   15420
gggaccctgg gtgggagcat aggaggggtc tggacatgtg gttactagta caggttttgc   15480
cctgattaaa aaatctccca aagccccaaa ttcctgttag ccaggtggag gcttctgata   15540
cgtgtatgag actatgcaaa agtacaaggg ctgagattct tcgtgtatag ctgtgtgaac   15600
gtgtatgtac ctaggatatg ttaaatatat agctggcacc ttagttgcat gaccacatag   15660
aacatgtgtc tatctgcttt tgcctacgtg acaacacaaa tttgggaggg tgagacactg   15720
cacagaagac agcagcaagt gtgctggcct ctctgacata tgctaacccc caaatactct   15780
gaatttggag tctgactgtg cccaagtggg tccaagtggc tgtgacatct acgtatggct   15840
ccacacctcc aatgctgcct gggagccagg gtgagagtct gggtccaggc ctggccatgt   15900
ggccctccag tgtatgagag ggcctgcct gctgcatctt ttctgttgcc ccatccaccg    15960
ccagcttccc ttcactcccc tatcccattc tccctctcaa ggcagggtc atagatccta    16020 agccataaaa taaattttat tccaaaataa caaaataaat aatctactgt acacaatctg   16080
aaaagaaaga cgctctaact gctcagatag gtgctgcggt ccagccccca gctggaggag   16140
```

```
acctgagtc caacccaggc ctcccgaggg ggccagtgaa gggatcccac acccaccgcc    16200
cctatgtagg gcagggaaga aattgcaaag gacttggggg atagatggga atgggagggc    16260
aaactgcagc acttgttaaa ttaattaaag aaacaaacca gaagcacaaa acgggggaag    16320
gagagggagg aaggagcagg tccagtgttc ccaggccccc aattctgggg gcaaatgttg    16380
ccacttttag ctggaccttc cagggaagt ccccctttcc cccttgtcca aactgagtcc     16440
aactgctcac accactggtg caaacctaaa gagaatggga gtgtgttgtg tgagggaggg    16500
```

<210> SEQ ID NO 13
<211> LENGTH: 697
<212> TYPE: DNA
<213> ORGANISM: H. sapiens

<400> SEQUENCE: 13

```
ttctcttccc tttcacttcc acactttgtc cctccccca aatttttat ttttttgtcc       60 acgcccaac aatttttttt gttttttttt tttaaaagaa tccaccccct ttcctgagct      120
ccctgactgg gatttcactt cttcacctcc caccgtggcc accagagtta aaaacctatc    180
ttataatata aataaaaaa ggaaagaaag aaagaaaaga aaccctgtcc tcaccctctt     240
caggccctgg tctctgcccc tggtggtcat cgtccatggc aaccaagaca acatgccaaa    300
ccactatcct gtgggacatg ccttctctga gatggaccgc gtgccctttg tggtggctga    360
gcgggtgccc tgggagaaga tgtgtgaaac tctgaacctg aagttcatgg ctgaggtggg    420
gaccaaccgg gggctgctcc cagagcactt cctcttcctg gcccagaaga tcttcaatga    480
caacagcctc agtatggagg ccttccagca ccgttctgtg tcctggtcgc agttcaacaa    540
ggagatcctg ctggccgtgg cttcaccttt tggcagtggt ttgatggtgt cctggacctc    600
accaacgctg tctccggagc tactggtctg accggtgagt ccccaccctg ggtagtctga    660
gcagccatac accagtcacc tccatactca ctgccca                             697
```

<210> SEQ ID NO 14
<211> LENGTH: 423
<212> TYPE: DNA
<213> ORGANISM: H. sapiens
<220> FEATURE:
<221> NAME/KEY: unsure
<222> LOCATION: 58
<223> OTHER INFORMATION: unknown

<400> SEQUENCE: 14

```
tggacagtgg gtaggtcagg ggcttagtgc ttatctgcag gaaggagggg tggcatcnac     60
ccttggtcag tcacatgtac ctccttccct cctccaggga ccaaccactt cctaccccag    120
agctccagat gcctaccatg gtgccttctt atgaccttgg aatggcccct gattcctcca    180
tgagcatgca gcttggccca gatatggtgc cccaggtgta cccaccacac tctcactcca    240 tcccccgta tcaaggcctc tccccagaag aatcagtcaa cgtgttgtca gccttccagg     300
agcctcacct gcagatgccc cccagcctgg gccagatgag cctgcccttt gaccagcctc    360
acccccaggg cctgctgtcg tgccagcctc tggagcatgc tgtgtccagc cctgacccc     420 tgc                                                                   423
```

<210> SEQ ID NO 15
<211> LENGTH: 20
<212> TYPE: DNA
<213> ORGANISM: Artificial Sequence
<220> FEATURE:
<223> OTHER INFORMATION: Antisense Oligonucleotide

```
<400> SEQUENCE: 15
agtgagcgaa tggacaggtc                                              20

<210> SEQ ID NO 16
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 16
cgctgtcact ggctggctca                                              20

<210> SEQ ID NO 17
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 17
ttgatgattt ctccagtgct                                              20

<210> SEQ ID NO 18
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 18
aggacttcat ccagccggcc                                              20

<210> SEQ ID NO 19
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 19
cccaggaacc tcaagcccaa                                              20

<210> SEQ ID NO 20
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 20
gtcacccaga agatgccgca                                              20

<210> SEQ ID NO 21
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 21
tttccacggt catcttgatg                                              20

<210> SEQ ID NO 22
<211> LENGTH: 20
```

```
<212> TYPE: DNA
<213> ORGANISM: Artificial Sequence
<220> FEATURE:
<223> OTHER INFORMATION: Antisense Oligonucleotide

<400> SEQUENCE: 22
aagatggtgc tccccctcccc                                              20

<210> SEQ ID NO 23
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 23
gccgtttcca aatctggatc                                               20

<210> SEQ ID NO 24
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 24
ctttggctgc ctctagctct                                               20

<210> SEQ ID NO 25
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 25
gtttggtgag gtccaggaca                                               20

<210> SEQ ID NO 26
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 26
catctgcagg tgaggctcct                                               20

<210> SEQ ID NO 27
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 27
tggcccttag gtccatgtgg                                               20

<210> SEQ ID NO 28
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 28
ctatctgtgg agagccatcc                                               20
```

```
<210> SEQ ID NO 29
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 29
attgagaaga aggctagtaa                                              20

<210> SEQ ID NO 30
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 30
gctgatgtgt tgcaagatgg                                              20

<210> SEQ ID NO 31
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 31
gccccatcac cctcagagag                                              20

<210> SEQ ID NO 32
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 32
ccctctgata tatgctctca                                              20

<210> SEQ ID NO 33
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 33
gaaggctagt aacgtactgt                                              20

<210> SEQ ID NO 34
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 34
gttccgtcgg gctcattgag                                              20

<210> SEQ ID NO 35
<211> LENGTH: 20
<212> TYPE: DNA
<213> ORGANISM: Artificial Sequence
<220> FEATURE:
<223> OTHER INFORMATION: Antisense Oligonucleotide
```

<400> SEQUENCE: 35
gtcactggct ggctcaggca                                                    20

<210> SEQ ID NO 36
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 36
ttcagagttt cacacatctt                                                    20

<210> SEQ ID NO 37
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 37
caggccccat aggtctgtag                                                    20

<210> SEQ ID NO 38
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 38
tatcaagctg tgcagagaca                                                    20

<210> SEQ ID NO 39
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 39
caggaactcc cagggctggc                                                    20

<210> SEQ ID NO 40
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 40
gctctgtatg tgtgtgtgcg                                                    20

<210> SEQ ID NO 41
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 41
agatcccgga ttcggtcccc                                                    20

<210> SEQ ID NO 42
<211> LENGTH: 20

```
<212> TYPE: DNA
<213> ORGANISM: Artificial Sequence
<220> FEATURE:
<223> OTHER INFORMATION: Antisense Oligonucleotide

<400> SEQUENCE: 42
cggtgcgcca ttccctgcca                                                    20

<210> SEQ ID NO 43
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 43
gggatagaga ttttttgagct                                                   20

<210> SEQ ID NO 44
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 44
gatctgggac ttggaggttg                                                    20

<210> SEQ ID NO 45
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 45
tccaaggtca taagaaggca                                                    20

<210> SEQ ID NO 46
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 46
atgatcagcc ggtcagacca                                                    20

<210> SEQ ID NO 47
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 47
cccaggaatg ctgttctcca                                                    20

<210> SEQ ID NO 48
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 48
tctcaggact tcatccagcc                                                    20
```

<210> SEQ ID NO 49
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 49
ccagcaggat ctccttgttg                                        20

<210> SEQ ID NO 50
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 50
tccagtgctt tctgctccag                                        20

<210> SEQ ID NO 51
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 51
acagtgtctg aaagtagggc                                        20

<210> SEQ ID NO 52
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 52
gctggccctg ctagcacctc                                        20

<210> SEQ ID NO 53
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 53
ccacagagac atgatctggg                                        20

<210> SEQ ID NO 54
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 54
gtcttaaact tgagttcttc                                        20

<210> SEQ ID NO 55
<211> LENGTH: 20
<212> TYPE: DNA
<213> ORGANISM: Artificial Sequence
<220> FEATURE:
<223> OTHER INFORMATION: Antisense Oligonucleotide

```
<400> SEQUENCE: 55
tctagctctc cagtggtctc                                              20

<210> SEQ ID NO 56
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 56
ggccctgacc agcggaggct                                              20

<210> SEQ ID NO 57
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 57
cctctgtgac agactcagtg                                              20

<210> SEQ ID NO 58
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 58
tccatactga ggctgttgtc                                              20

<210> SEQ ID NO 59
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 59
cctggccccg gatgacatgg                                              20

<210> SEQ ID NO 60
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 60
gaaggcacca tggtaggcat                                              20

<210> SEQ ID NO 61
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 61
ccaatccaag tgccctgagg                                              20

<210> SEQ ID NO 62
<211> LENGTH: 20
```

```
<212> TYPE: DNA
<213> ORGANISM: Artificial Sequence
<220> FEATURE:
<223> OTHER INFORMATION: Antisense Oligonucleotide

<400> SEQUENCE: 62
cagctgggat caccaactgg                                           20

<210> SEQ ID NO 63
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 63
gtgtctcaga gcctgaactt                                           20

<210> SEQ ID NO 64
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 64
taagcagtgg ctgccccagc                                           20

<210> SEQ ID NO 65
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 65
cctccctctt cagtgtaagc                                           20

<210> SEQ ID NO 66
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 66
agaagccttc catgccctaa                                           20

<210> SEQ ID NO 67
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 67
tatgttcctg cctatccgtc                                           20

<210> SEQ ID NO 68
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 68
caactaaggt gccagctata                                           20
```

-continued

```
<210> SEQ ID NO 69
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 69
tggtcatgca actaaggtgc                                                   20

<210> SEQ ID NO 70
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 70
atttgtgttg tcacgtaggc                                                   20

<210> SEQ ID NO 71
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 71
tctcaccctc ccaaatttgt                                                   20

<210> SEQ ID NO 72
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 72
agcacacttg ctgctgtctt                                                   20

<210> SEQ ID NO 73
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 73
gccaggcctg gacccagact                                                   20

<210> SEQ ID NO 74
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 74
gggcaacaga aaagatgcag                                                   20

<210> SEQ ID NO 75
<211> LENGTH: 20
<212> TYPE: DNA
<213> ORGANISM: Artificial Sequence
<220> FEATURE:
<223> OTHER INFORMATION: Antisense Oligonucleotide
```

<400> SEQUENCE: 75
aatgtcagct tttaatctgt                                            20

<210> SEQ ID NO 76
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 76
gagtcaatgc ctgagatggg                                            20

<210> SEQ ID NO 77
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 77
caggaagcaa ctgggagtga                                            20

<210> SEQ ID NO 78
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 78
ccatctcaga gaaggcattg                                            20

<210> SEQ ID NO 79
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 79
tgcacatgtc cctgtgggat                                            20

<210> SEQ ID NO 80
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 80
gggactcacc ggtcagacca                                            20

<210> SEQ ID NO 81
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 81
agtggttggt ccctggagga                                            20

<210> SEQ ID NO 82
<211> LENGTH: 20

```
<212> TYPE: DNA
<213> ORGANISM: Artificial Sequence
<220> FEATURE:
<223> OTHER INFORMATION: Antisense Oligonucleotide

<400> SEQUENCE: 82
agctccttac accatatctg                                               20

<210> SEQ ID NO 83
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 83
caaagtgtgg aagtgaaagg                                               20

<210> SEQ ID NO 84
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 84
ctctggtggc cacggtggga                                               20

<210> SEQ ID NO 85
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 85
ggtgtatggc tgctcagact                                               20

<210> SEQ ID NO 86
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 86
aggaggtaca tgtgactgac                                               20

<210> SEQ ID NO 87
<211> LENGTH: 20
<212> TYPE: DNA
<213> ORGANISM: Homo sapiens

<400> SEQUENCE: 87
gacctgtcca ttcgctcact                                               20

<210> SEQ ID NO 88
<211> LENGTH: 20
<212> TYPE: DNA
<213> ORGANISM: Homo sapiens

<400> SEQUENCE: 88
tgagccagcc agtgacagcg                                               20

<210> SEQ ID NO 89
<211> LENGTH: 20
```

```
<212> TYPE: DNA
<213> ORGANISM: Homo sapiens

<400> SEQUENCE: 89
agcactggag aaatcatcaa                                              20

<210> SEQ ID NO 90
<211> LENGTH: 20
<212> TYPE: DNA
<213> ORGANISM: Homo sapiens

<400> SEQUENCE: 90
ttgggcttga ggttcctggg                                              20

<210> SEQ ID NO 91
<211> LENGTH: 20
<212> TYPE: DNA
<213> ORGANISM: Homo sapiens

<400> SEQUENCE: 91
gatccagatt tggaaacggc                                              20

<210> SEQ ID NO 92
<211> LENGTH: 20
<212> TYPE: DNA
<213> ORGANISM: Homo sapiens

<400> SEQUENCE: 92
agagctagag gcagccaaag                                              20

<210> SEQ ID NO 93
<211> LENGTH: 20
<212> TYPE: DNA
<213> ORGANISM: Homo sapiens

<400> SEQUENCE: 93
tgtcctggac ctcaccaaac                                              20

<210> SEQ ID NO 94
<211> LENGTH: 20
<212> TYPE: DNA
<213> ORGANISM: Homo sapiens

<400> SEQUENCE: 94
aggagcctca cctgcagatg                                              20

<210> SEQ ID NO 95
<211> LENGTH: 20
<212> TYPE: DNA
<213> ORGANISM: Homo sapiens

<400> SEQUENCE: 95
ccacatggac ctaagggcca                                              20

<210> SEQ ID NO 96
<211> LENGTH: 20
<212> TYPE: DNA
<213> ORGANISM: Homo sapiens

<400> SEQUENCE: 96
ggatggctct ccacagatag                                              20

<210> SEQ ID NO 97
<211> LENGTH: 20
```

-continued

```
<212> TYPE: DNA
<213> ORGANISM: Homo sapiens

<400> SEQUENCE: 97
ttactagcct tcttctcaat                                              20

<210> SEQ ID NO 98
<211> LENGTH: 20
<212> TYPE: DNA
<213> ORGANISM: Homo sapiens

<400> SEQUENCE: 98
ccatcttgca acacatcagc                                              20

<210> SEQ ID NO 99
<211> LENGTH: 20
<212> TYPE: DNA
<213> ORGANISM: Homo sapiens

<400> SEQUENCE: 99
ctctctgagg gtgatggggc                                              20

<210> SEQ ID NO 100
<211> LENGTH: 20
<212> TYPE: DNA
<213> ORGANISM: Homo sapiens

<400> SEQUENCE: 100
tgagagcata tatcagaggg                                              20

<210> SEQ ID NO 101
<211> LENGTH: 20
<212> TYPE: DNA
<213> ORGANISM: Homo sapiens

<400> SEQUENCE: 101
acagtacgtt actagccttc                                              20

<210> SEQ ID NO 102
<211> LENGTH: 20
<212> TYPE: DNA
<213> ORGANISM: Homo sapiens

<400> SEQUENCE: 102
ctcaatgagc ccgacggaac                                              20

<210> SEQ ID NO 103
<211> LENGTH: 20
<212> TYPE: DNA
<213> ORGANISM: Homo sapiens

<400> SEQUENCE: 103
tgcctgagcc agccagtgac                                              20

<210> SEQ ID NO 104
<211> LENGTH: 20
<212> TYPE: DNA
<213> ORGANISM: Homo sapiens

<400> SEQUENCE: 104
aagatgtgtg aaactctgaa                                              20

<210> SEQ ID NO 105
<211> LENGTH: 20
```

```
<212> TYPE: DNA
<213> ORGANISM: Homo sapiens

<400> SEQUENCE: 105
ctacagacct atggggcctg                                               20

<210> SEQ ID NO 106
<211> LENGTH: 20
<212> TYPE: DNA
<213> ORGANISM: Homo sapiens

<400> SEQUENCE: 106
tgtctctgca cagcttgata                                               20

<210> SEQ ID NO 107
<211> LENGTH: 20
<212> TYPE: DNA
<213> ORGANISM: Homo sapiens

<400> SEQUENCE: 107
gccagccctg ggagttcctg                                               20

<210> SEQ ID NO 108
<211> LENGTH: 20
<212> TYPE: DNA
<213> ORGANISM: Homo sapiens

<400> SEQUENCE: 108
cgcacacaca catacagagc                                               20

<210> SEQ ID NO 109
<211> LENGTH: 20
<212> TYPE: DNA
<213> ORGANISM: Homo sapiens

<400> SEQUENCE: 109
ggggaccgaa tccgggatct                                               20

<210> SEQ ID NO 110
<211> LENGTH: 20
<212> TYPE: DNA
<213> ORGANISM: Homo sapiens

<400> SEQUENCE: 110
tggcagggaa tggcgcaccg                                               20

<210> SEQ ID NO 111
<211> LENGTH: 20
<212> TYPE: DNA
<213> ORGANISM: Homo sapiens

<400> SEQUENCE: 111
caacctccaa gtcccagatc                                               20

<210> SEQ ID NO 112
<211> LENGTH: 20
<212> TYPE: DNA
<213> ORGANISM: Homo sapiens

<400> SEQUENCE: 112
tgccttctta tgaccttgga                                               20

<210> SEQ ID NO 113
<211> LENGTH: 20
```

```
<212> TYPE: DNA
<213> ORGANISM: Homo sapiens

<400> SEQUENCE: 113
tggtctgacc ggctgatcat                                          20

<210> SEQ ID NO 114
<211> LENGTH: 20
<212> TYPE: DNA
<213> ORGANISM: Homo sapiens

<400> SEQUENCE: 114
tggagaacag cattcctggg                                          20

<210> SEQ ID NO 115
<211> LENGTH: 20
<212> TYPE: DNA
<213> ORGANISM: Homo sapiens

<400> SEQUENCE: 115
caacaaggag atcctgctgg                                          20

<210> SEQ ID NO 116
<211> LENGTH: 20
<212> TYPE: DNA
<213> ORGANISM: Homo sapiens

<400> SEQUENCE: 116
ctggagcaga aagcactgga                                          20

<210> SEQ ID NO 117
<211> LENGTH: 20
<212> TYPE: DNA
<213> ORGANISM: Homo sapiens

<400> SEQUENCE: 117
gaggtgctag cagggccagc                                          20

<210> SEQ ID NO 118
<211> LENGTH: 20
<212> TYPE: DNA
<213> ORGANISM: Homo sapiens

<400> SEQUENCE: 118
cccagatcat gtctctgtgg                                          20

<210> SEQ ID NO 119
<211> LENGTH: 20
<212> TYPE: DNA
<213> ORGANISM: Homo sapiens

<400> SEQUENCE: 119
gagaccactg gagagctaga                                          20

<210> SEQ ID NO 120
<211> LENGTH: 20
<212> TYPE: DNA
<213> ORGANISM: Homo sapiens

<400> SEQUENCE: 120
agcctccgct ggtcagggcc                                          20

<210> SEQ ID NO 121
<211> LENGTH: 20
```

<212> TYPE: DNA
<213> ORGANISM: Homo sapiens

<400> SEQUENCE: 121
cactgagtct gtcacagagg                                        20

<210> SEQ ID NO 122
<211> LENGTH: 20
<212> TYPE: DNA
<213> ORGANISM: Homo sapiens

<400> SEQUENCE: 122
cctcagggca cttggattgg                                        20

<210> SEQ ID NO 123
<211> LENGTH: 20
<212> TYPE: DNA
<213> ORGANISM: Homo sapiens

<400> SEQUENCE: 123
aagttcaggc tctgagacac                                        20

<210> SEQ ID NO 124
<211> LENGTH: 20
<212> TYPE: DNA
<213> ORGANISM: Homo sapiens

<400> SEQUENCE: 124
gcttacactg aagagggagg                                        20

<210> SEQ ID NO 125
<211> LENGTH: 20
<212> TYPE: DNA
<213> ORGANISM: Homo sapiens

<400> SEQUENCE: 125
ttagggcatg gaaggcttct                                        20

<210> SEQ ID NO 126
<211> LENGTH: 20
<212> TYPE: DNA
<213> ORGANISM: Homo sapiens

<400> SEQUENCE: 126
gacggatagg caggaacata                                        20

<210> SEQ ID NO 127
<211> LENGTH: 20
<212> TYPE: DNA
<213> ORGANISM: Homo sapiens

<400> SEQUENCE: 127
tatagctggc accttagttg                                        20

<210> SEQ ID NO 128
<211> LENGTH: 20
<212> TYPE: DNA
<213> ORGANISM: Homo sapiens

<400> SEQUENCE: 128
gcaccttagt tgcatgacca                                        20

<210> SEQ ID NO 129
<211> LENGTH: 20

```
<212> TYPE: DNA
<213> ORGANISM: Homo sapiens

<400> SEQUENCE: 129
gcctacgtga caacacaaat                                               20

<210> SEQ ID NO 130
<211> LENGTH: 20
<212> TYPE: DNA
<213> ORGANISM: Homo sapiens

<400> SEQUENCE: 130
aagacagcag caagtgtgct                                               20

<210> SEQ ID NO 131
<211> LENGTH: 20
<212> TYPE: DNA
<213> ORGANISM: Homo sapiens

<400> SEQUENCE: 131
agtctgggtc caggcctggc                                               20

<210> SEQ ID NO 132
<211> LENGTH: 20
<212> TYPE: DNA
<213> ORGANISM: Homo sapiens

<400> SEQUENCE: 132
acagattaaa agctgacatt                                               20

<210> SEQ ID NO 133
<211> LENGTH: 20
<212> TYPE: DNA
<213> ORGANISM: Homo sapiens

<400> SEQUENCE: 133
caatgccttc tctgagatgg                                               20

<210> SEQ ID NO 134
<211> LENGTH: 20
<212> TYPE: DNA
<213> ORGANISM: Homo sapiens

<400> SEQUENCE: 134
atcccacagg gacatgtgca                                               20

<210> SEQ ID NO 135
<211> LENGTH: 20
<212> TYPE: DNA
<213> ORGANISM: Homo sapiens

<400> SEQUENCE: 135
tcctccaggg accaaccact                                               20

<210> SEQ ID NO 136
<211> LENGTH: 20
<212> TYPE: DNA
<213> ORGANISM: Homo sapiens

<400> SEQUENCE: 136
agtctgagca gccatacacc                                               20

<210> SEQ ID NO 137
<211> LENGTH: 3790
```

```
<212> TYPE: DNA
<213> ORGANISM: Homo sapiens

<400> SEQUENCE: 137
gctgagaaag ggagaagaca gcagaggggt tgccgagaga aaggcctatt ggaggaacct      60
gagcaggagg ggtaaggatt ctgccttgag gagaaaagag ctggggcaac ctccaagtcc     120
cagatcatgt ctctgtgggg tctggtctcc aagatgcccc cagaaaaagt gcagcggctc     180
tatgtcgact ttccccaaca cctgcggcat cttctgggtg actggctgga gagccagccc     240
tgggagttcc tggtcggctc cgacgccttc tgctgcaact tggctagtgc cctactttca     300
gacactgtcc agcaccttca ggcctcggtg ggagagcagg ggagggggag caccatcttg     360
caacacatca gcacccttga gagcatatat cagagggacc ccctgaagct ggtggccact     420
ttcagacaaa tacttcaagg agagaaaaaa gctgttatgg aacagttccg ccacttgcca     480
atgcctttcc actggaagca ggaagaactc aagtttaaga caggcttgcg gaggctgcag     540
caccgagtag gggagatcca ccttctccga aagccctgc agaaggggc tgaggctggc      600 caagtgtctc tgcacagctt gatagaaact cctgctaatg ggactgggcc aagtgaggcc     660
ctggccatgc tactgcagga gaccactgga gagctagagg cagccaaagc cctagtgctg     720
aagaggatcc agatttggaa acggcagcag cagctggcag ggaatggcgc accgtttgag     780
gagagcctgg ccccactcca ggagaggtgt gaaagcctgg tggacattta ttcccagcta     840
cagcaggagg taggggcggc tggtggggag cttgagccca agacccgggc atcgctgact     900
ggccggctga tgaagtcct gagaaccctc gtcaccagtt gcttcctggt ggagaagcag     960 ccccccccagg tactgaagac tcagaccaag ttccaggctg gagttcgatt cctgttgggc    1020
ttgaggttcc tggggggcccc agccaagcct ccgctggtca gggccgacat ggtgacagag    1080
aagcaggcgc gggagctgag tgtgcctcag ggtcctgggg ctggagcaga aagcactgga    1140
gaaatcatca acaacactgt gcccttggag aacagcattc ctgggaactg ctgctctgcc    1200
ctgttcaaga acctgcttct caagaagatc aagcggtgtg agcggaaggg cactgagtct    1260
gtcacagaga agaagtgcgc tgtgctcttc tctgccagct tcacacttgg ccccggcaaa    1320
ctccccatcc agctccaggc cctgtctctg ccccctggtgg tcatcgtcca tggcaaccaa    1380
gacaacaatg ccaaagccac tatcctgtgg acaatgcct tctctgagat ggaccgcgtg    1440 cccctttgtgg tggctgagcg ggtgccctgg gagaagatgt gtgaaactct gaacctgaag    1500
ttcatggctg aggtggggac caaccggggg ctgctcccag agcacttcct cttcctggcc    1560
cagaagatct tcaatgacaa cagcctcagt atggaggcct tccagcaccg ttctgtgtcc    1620
tggtcgcagt tcaacaagga gatcctgctg ggccgtggct tcacctttg gcagtggttt    1680 gatggtgtcc tggacctcac caaacgctgt ctccggagct actggtctga ccgcgactca    1740
gagattgggg gcatcaccat tgcccatgtc atccggggcc aggatggctc tccacagata    1800
gagaacatcc agccattctc tgccaaagac ctgtccattc gctcactggg ggaccgaatc    1860
cgggatcttg ctcagctcaa aaatctctat cccaagaagc ccaaggatga ggctttccgg    1920
agccactaca agcctgaaca gatgggtaag gatggcaggg gttatgtccc agctaccatc    1980
aagatgaccg tggaaaggga ccaaccactt cctaccccag agctccagat gcctaccatg    2040
gtgccttctt atgaccttgg aatggcccct gattcctcca tgagcatgca gcttggccca    2100
gatatggtgc cccaggtgta cccaccacac tctcactcca tccccccgta tcaaggcctc    2160
tccccagaag aatcagtcaa cgtgttgtca gccttccagg agcctcacct gcagatgccc    2220
cccagcctgg gccagatgag cctgccctt gaccagcctc acccccaggg cctgctgccg    2280
```

```
tgccagcctc aggagcatgc tgtgtccagc cctgaccccc tgctctgctc agatgtgacc    2340
atggtggaag acagctgcct gagccagcca gtgacagcgt ttcctcaggg cacttggatt    2400
ggtgaagaca tattccctcc tctgctgcct cccactgaac aggacctcac taagcttctc    2460 ctggagggc aaggggagtc ggggggaggg tccttggggg cacagcccct cctgcagccc     2520
tcccactatg ggcaatctgg gatctcaatg tcccacatgg acctaagggc caaccccagt    2580
tggtgatccc agctggaggg agaacccaaa gagacagctc ttctactacc cccacagacc    2640
tgctctggac acttgctcat gccctgccaa gcagcagatg gggagggtgc cctcctatcc    2700
ccacctactc ctgggtcagg aggaaaagac taacaggaga atgcacagtg ggtggagcca    2760
atccactcct tcctttctat cattcccctg cccacctcct tccagcactg actggaaggg    2820
aagttcaggc tctgagacac gccccaacat gcctgcacct gcagcgcgca cacgcacgca    2880
cacacacata cagagctctc tgagggtgat ggggctgagc aggaggggg ctgggtaaga    2940 gcacaggtta gggcatggaa ggcttctccg cccattctga cccagggcct aggacggata    3000
ggcaggaaca tacagacaca tttacactag aggccaggga tagaggatat tgggtctcag    3060
ccctagggga atgggaagca gctcaaggga ccctgggtgg gagcatagga ggagtctgga    3120
catgtggtta ctagtacagg ttttgccctg attaaaaaat ctcccaaagc cccaaattcc    3180
tgttagccag gtggaggctt ctgatacgtg tatgagacta tgcaaagta caagggctga    3240 gattcttcgt gtatagctgt gtgaacgtgt atgtacctag gatatgttaa atatatagct    3300
ggcaccttag ttgcatgacc acatagaaca tgtgtctatc tgcttttgcc tacgtgacaa    3360
cacaaatttg ggagggtgag acactgcaca gaagacagca gcaagtgtgc tggcctctct    3420
gacatatgct aaccccccaaa tactctgaat ttggagtctg actgtgccca gtgggtcca    3480 agtggctgtg acatctacgt atggctccac acctccaatg ctgcctggga gccagggtga    3540
gagtctgggt ccaggcctgg ccatgtggcc ctccagtgta tgagagggcc ctgcctgctg    3600
catcttttct gttgccccat ccaccgccag cttcccttca ctcccctatc ccattctccc    3660
tctcaaggca ggggtcatag atcctaagcc ataaaataaa ttttattcca aaataacaaa    3720
ataaataatc tactgtacac aatctgaaaa aaaaaaaaa aaaaaaaaaa aaaaaaaaa     3780 aaaaaaaaaa                                                          3790
```

<210> SEQ ID NO 138
<211> LENGTH: 3667
<212> TYPE: DNA
<213> ORGANISM: Homo sapiens

<400> SEQUENCE: 138

```
gacagagcta cagacctatg gggcctggaa gtgcccgctg agaaagggag aagacagcag      60
aggggttgcc gaggcaacct ccaagtccca gatcatgtct ctgtggggtc tggtctccaa     120
gatgccccca gaaaaagtgc agcggctcta tgtcgacttt cccccaacacc tgcggcatct    180 tctgggtgac tggctggaga gccagccctg agcatatatc agaggaccc cctgaagctg     240 gtggccactt tcagacaaat acttcaagga gagaaaaaag ctgttatgga acagttccgc    300
cacttgccaa tgccttttcca ctggaagcag gaagaactca gtttaagac aggcttgcgg    360 aggctgcagc accgagtagg ggagatccac cttctccgag aagccctgca gaagggggct    420
gaggctggcc aagtgtctct gcacagcttg atagaaactc ctgctaatgg gactgggcca    480
agtgaggccc tggccatgct actgcaggag accactggag agctagaggc agccaaagcc    540
ctagtgctga agaggatcca gatttggaaa cggcagcagc agctggcagg gaatggcgca    600
```

```
ccgtttgagg agagcctggc cccactccag gagaggtgtg aaagcctggt ggacatttat    660
tcccagctac agcaggaggt aggggcggct ggtggggagc ttgagcccaa gacccgggca    720
tcgctgactg gccggctgga tgaagtcctg agaaccctcg tcaccagttg cttcctggtg    780
gagaagcagc cccccaggt actgaagact cagaccaagt tccaggctgg agttcgattc     840
ctgtttgggct tgaggttcct gggggcccca gccaagcctc cgctggtcag ggccgacatg   900
gtgacagaga agcaggcgcg ggagctgagt gtgcctcagg gtcctggggc tggagcagaa    960
agcactggag aaatcatcaa caacactgtg cccttggaga acagcattcc tgggaactgc   1020
tgctctgccc tgttcaagaa cctgcttctc aagaagatca gcggtgtga gcggaagggc    1080
actgagtctg tcacagagga gaagtgcgct gtgctcttct ctgccagctt cacacttggc   1140
cccggcaaac tccccatcca gctccaggcc ctgtctctgc ccctggtggt catcgtccat   1200
ggcaaccaag acaacaatgc caaagccact atcctgtggg acaatgcctt ctctgagatg   1260
gaccgcgtgc cctttgtggt ggctgagcgg gtgccctggg agaagatgtg tgaaactctg   1320
aacctgaagt tcatggctga ggtggggacc aaccgggggc tgctcccaga gcacttcctc   1380
ttcctggccc agaagatctt caatgacaac agcctcagta tggaggcctt ccagcaccgt   1440
tctgtgtcct ggtcgcagtt caacaaggag atcctgctgg gccgtggctt cacctttggg   1500
cagtggtttg atggtgtcct ggacctcacc aaacgctgtc tccggagcta ctggtctgac   1560
cggctgatca ttggcttcat cagcaaacag tacgttacta gccttcttct caatgagccc   1620
gacgaacct ttctcctccg cttcagcgac tcagagattg ggggcatcac cattgcccat   1680
gtcatccggg gccaggatgg ctctccacag atagagaaca tccagccatt ctctgccaaa   1740
gacctgtcca ttcgctcact gggggaccga atccgggatc ttgctcagct caaaaatctc   1800
tatcccaaga agcccaagga tgaggctttc cggagccact acaagcctga acagatgggt   1860
aaggatggca ggggttatgt cccagctacc atcaagatga ccgtggaaag ggaccaacca   1920
cttcctaccc cagagctcca gatgcctacc atggtgcctt cttatgacct tggaatggcc   1980
cctgattcct ccatgagcat gcagcttggc ccagatatgg tgccccaggt gtacccacca   2040
cactctcact ccatcccccc gtatcaaggc ctctcccag aagaatcagt caacgtgttg    2100
tcagccttcc aggagcctca cctgcagatg ccccccagcc tgggccagat gagcctgccc   2160
tttgaccagc ctcacccca gggcctgctg ccgtgccagc ctcaggagca tgctgtgtcc    2220
agccctgacc ccctgctctg ctcagatgtg accatggtgg aagacagctg cctgagccag   2280
ccagtgacag cgtttcctca gggcacttgg attggtgaag acatattccc tcctctgctg   2340
cctcccactg aacaggacct cactaagctt ctcctggagg ggcaagggga gtcggggga    2400
gggtccttgg gggcacagcc cctcctgcag ccctcccact atgggcaatc tgggatctca   2460
atgtcccaca tggacctaag ggccaacccc agttggtgat cccagctgga gggagaaccc   2520
aaagagacag ctcttctact accccacag acctgctctg acacttgct catgccctgc    2580
caagcagcag atggggaggg tgccctccta tccccaccta ctcctgggtc aggaggaaaa   2640
gactaacagg agaatgcaca gtgggtggag ccaatccact ccttcctttc tatcattccc   2700
ctgcccacct ccttccagca ctgactggaa gggaagttca ggctctgaga cacgccccaa   2760
catgcctgca cctgcagcgc gcacacgcac gcacacacac atacagagct ctctgagggt   2820
gatgggctg agcaggaggg gggctgggta agagcacagg ttagggcatg aaggcttct    2880
ccgcccattc tgacccaggg cctaggacgg ataggcagga acatacagac acatttacac   2940
tagaggccag ggatagagga tattgggtct cagccctagg ggaatgggaa gcagctcaag   3000
```

-continued

```
ggaccctggg tgggagcata ggaggagtct ggacatgtgg ttactagtac aggttttgcc    3060
ctgattaaaa aatctcccaa agccccaaat tcctgttagc caggtggagg cttctgatac    3120
gtgtatgaga ctatgcaaaa gtacaagggc tgagattctt cgtgtatagc tgtgtgaacg    3180
tgtatgtacc taggatatgt taaatatata gctggcacct tagttgcatg accacataga    3240
acatgtgtct atctgctttt gcctacgtga caacacaaat tgggagggt gagacactgc     3300 acagaagaca gcagcaagtg tgctggcctc tctgacatat gctaaccccc aaatactctg    3360
aatttggagt ctgactgtgc ccaagtgggt ccaagtggct gtgacatcta cgtatggctc    3420
cacacctcca atgctgcctg ggagccaggg tgagagtctg ggtccaggcc tggccatgtg    3480
gccctccagt gtatgagagg gccctgcctg ctgcatcttt tctgttgccc catccaccgc    3540
cagcttccct tcactcccct atcccattct ccctctcaag gcagggtca tagatcctaa      3600 gccataaaat aaattttatt ccaaaataaa aaaaaaaaa aaaaaaaaa aaaaaaaaa       3660 aaaaaaa                                                                3667
```

```
<210> SEQ ID NO 139
<211> LENGTH: 19
<212> TYPE: RNA
<213> ORGANISM: Artificial Sequence
<220> FEATURE:
<223> OTHER INFORMATION: Antisense Oligonucleotide

<400> SEQUENCE: 139
cgagaggcgg acgggaccg                                                    19

<210> SEQ ID NO 140
<211> LENGTH: 21
<212> TYPE: DNA
<213> ORGANISM: Artificial Sequence
<220> FEATURE:
<223> OTHER INFORMATION: Antisense Oligonucleotide
<220> FEATURE:
<221> NAME/KEY: misc_feature
<222> LOCATION: 1-19
<223> OTHER INFORMATION: bases at these positions are RNA

<400> SEQUENCE: 140
cgagaggcgg acgggaccgt t                                                 21

<210> SEQ ID NO 141
<211> LENGTH: 21
<212> TYPE: DNA
<213> ORGANISM: Artificial Sequence
<220> FEATURE:
<223> OTHER INFORMATION: Antisense Oligonucleotide
<220> FEATURE:
<221> NAME/KEY: misc_feature
<222> LOCATION: 1-19
<223> OTHER INFORMATION: bases at these positions are RNA

<400> SEQUENCE: 141
cggtcccgtc cgcctctcgt t                                                 21
```

MODULATION OF STAT 6 EXPRESSION

RELATED APPLICATIONS

This application is a continuation of U.S. application Ser. No. 12/510,132, filed Jul. 27, 2009, now abandoned, which is a continuation of U.S. application Ser. No. 11/152,530, filed Jun. 14, 2005, now abandoned, which is a divisional of U.S. application Ser. No. 10/317,391, filed Dec. 11, 2002, now abandoned, each of which is incorporated herein by reference in its entirety.

SEQUENCE LISTING

The present application is being filed along with a Sequence Listing in electronic format. The Sequence Listing is provided as a file entitled PTS0010USC2SEQ.txt, created on Jan. 11, 2012 which is 76 Kb in size. The information in the electronic format of the sequence listing is incorporated herein by reference in its entirety.

FIELD OF THE INVENTION

The present invention provides compositions and methods for modulating the expression of STAT 6. In particular, this invention relates to compounds, particularly oligonucleotide compounds, which, in preferred embodiments, hybridize with nucleic acid molecules encoding STAT 6. Such compounds are shown herein to modulate the expression of STAT 6.

BACKGROUND OF THE INVENTION

Cytokines function as protein mediators that play a critical role in host defense and serve as a communication link between cells of native and acquired immunity. Cells respond to cytokines with specific biological changes that are dependent on the activation of new gene expression.

Studies of the mechanism by which signals are signals are mediated from the receptor to the nucleus by the interferon cytokines have revealed the activation of latent cytoplasmic transcription factors that subsequently translocate to the nucleus (Bromberg, *BioEssays*, 2001, 23, 161-169).

The proteins of the STAT family (signal transducers and activators of transcription) are latent transcription factors that are abundantly expressed in many cell types. STATs are activated by phosphorylation on a single tyrosine in response to extracellular ligands. An active STAT dimer is formed through reciprocal interactions between the SH2 domain of one monomer and the phosphorylated tyrosine of the other monomer. The dimers accumulate in the nucleus, recognize specific DNA elements in the promoters of genes and activate transcription so that growth control and survival of normal cells in a developing or adult mammal are carefully balanced. Many of the signals that influence this balance are delivered by circulating polypeptides, whose binding to cell surface receptors governs gene-specific transcription. It has been shown that human cancer cells have lost control of these signaling mechanisms. In addition to persistent unregulated mitogenic signaling, the lack of suppressive signals is also critical in the development of cancers (Bromberg, *BioEssays*, 2001, 23, 161-169).

STAT 6 (also known as interleukin 4-STAT) was cloned and mapped to chromosome 12q13 (Leek et al., *Cytogenet. Cell Genet.*, 1997, 79, 208-209; Quelle et al., *Mol. Cell. Biol.*, 1995, 15, 3336-3343). Nucleic acid sequences encoding STAT 6 are disclosed and claimed in U.S. Pat. No. 5,710,266 (McKnight and Hou, 1998).

STAT 6 is primarily expressed as a 4 kb transcript in hematopoietic cells and expressed variably in other tissues (Quelle et al., *Mol. Cell. Biol.*, 1995, 15, 3336-3343). A unique truncated isoform of STAT 6 is expressed in mast cells (Sherman, *Immunol. Rev.*, 2001, 179, 48-56). Disclosed and claimed in PCT publication WO 99/10493 are nucleic acid sequences encoding variants of STAT 6 known as STAT 6b and STAT 6c as well as vectors comprising said nucleic acid sequences (Patel et al., 1999).

STAT 6 is an integral transcription factor involved in interleukin 4 and interleukin 13 signaling. Following activation of their respective receptors, interleukin 4 and interleukin 13 cause their common interleukin 4 receptor alpha chain to become phosphorylated by JAK3 and to subsequently bind to STAT 6. STAT 6 is then phosphorylated by JAK1, homodimerizes and translocates to the nucleus where it binds interleukin 4 response elements and initiates the transcription of a number of genes including IgE (Danahay et al., *Inflamm. Res.*, 2000, 49, 692-699).

STAT 6 is involved in key pathological mechanisms in rheumatoid arthritis which operate in early and late stages of the disease (Muller-Ladner et al., *J. Immunol.*, 2000, 164, 3894-3901).

Ghilardi et al. have found that STAT 6 interacts with an isoform of the leptin receptor (OB-R) and is thus, a potential mediator of the anti-obesity effects of leptin (Ghilardi et al., *Proc. Natl. Acad. Sci. U.S.A.*, 1996, 93, 6231-6235).

STAT 6 knockout mice are viable and develop normally with the exception that interleukin 4 functions are eliminated (Ihle, *Curr. Opin. Cell Biol.*, 2001, 13, 211-217). Additionally, STAT 6 knockout mice fail to develop antigen-induced airway hyper-reactivity in a model of airway inflammation (Kuperman et al., *J. Exp. Med.*, 1998, 187, 939-948). Inhibition of STAT 6 is expected to attenuate the allergic response and thus, represents an attractive target for drug discovery strategies (Hill et al., *Am. J. Respir. Cell Mol. Biol.*, 1999, 21, 728-737).

Small molecule inhibitors of STAT 6 are disclosed and claimed in PCT publication WO 00/27802 and Japanese Patent JP 2000229959 (Eyermann et al., 2000; Inoue et al., *PCT*, 2000, Abstract only). Disclosed and claimed in U.S. Pat. No. 6,207,391 are methods for screening modulators of STAT 6 binding to a STAT 6 receptor (Wu and McKinney, 2001).

Wang et al. have demonstrated targeted disruption of STAT 6 DNA-binding activity by a phosphorothioate cis-element decoy oligonucleotide (Wang et al., *Blood*, 2000, 95, 1249-1257).

Hill et al. have used a series of homologous human and murine antisense oligonucleotides targeting STAT 6 to interrupt interleukin 4 and interleukin 13 signaling and attenuate germline C-epsilon transcription in vitro (Hill et al., *Am. J. Respir. Cell Mol. Biol.*, 1999, 21, 728-737). Subsequently, the in vitro and in vivo pharmacology of three of the antisense oligonucleotides used in the latter study was investigated. Although the oligonucleotides downregulated STAT 6 mRNA, their action was not sufficient to influence alterations in mRNA levels (Danahay et al., *Inflamm. Res.*, 2000, 49, 692-699).

Currently, there are no known therapeutic agents that effectively inhibit the synthesis of STAT 6. Consequently, there remains a long felt need for additional agents capable of effectively inhibiting STAT 6 function.

Antisense technology is emerging as an effective means for reducing the expression of specific gene products and may therefore prove to be uniquely useful in a number of therapeutic, diagnostic, and research applications for the modulation of STAT 6 expression.

The present invention provides compositions and methods for modulating STAT 6 expression.

SUMMARY OF THE INVENTION

The present invention is directed to compounds, especially nucleic acid and nucleic acid-like oligomers, which are targeted to a nucleic acid encoding STAT 6, and which modulate the expression of STAT 6. Pharmaceutical and other compositions comprising the compounds of the invention are also provided. Further provided are methods of screening for modulators of STAT 6 and methods of modulating the expression of STAT 6 in cells, tissues or animals comprising contacting said cells, tissues or animals with one or more of the compounds or compositions of the invention. Methods of treating an animal, particularly a human, suspected of having or being prone to a disease or condition associated with expression of STAT 6 are also set forth herein. Such methods comprise administering a therapeutically or prophylactically effective amount of one or more of the compounds or compositions of the invention to the person in need of treatment.

DETAILED DESCRIPTION OF THE INVENTION

A. Overview of the Invention

The present invention employs compounds, preferably oligonucleotides and similar species for use in modulating the function or effect of nucleic acid molecules encoding STAT 6. This is accomplished by providing oligonucleotides which specifically hybridize with one or more nucleic acid molecules encoding STAT 6. As used herein, the terms "target nucleic acid" and "nucleic acid molecule encoding STAT 6" have been used for convenience to encompass DNA encoding STAT 6, RNA (including pre-mRNA and mRNA or portions thereof) transcribed from such DNA, and also cDNA derived from such RNA. The hybridization of a compound of this invention with its target nucleic acid is generally referred to as "antisense". Consequently, the preferred mechanism believed to be included in the practice of some preferred embodiments of the invention is referred to herein as "antisense inhibition." Such antisense inhibition is typically based upon hydrogen bonding-based hybridization of oligonucleotide strands or segments such that at least one strand or segment is cleaved, degraded, or otherwise rendered inoperable. In this regard, it is presently preferred to target specific nucleic acid molecules and their functions for such antisense inhibition.

The functions of DNA to be interfered with can include replication and transcription. Replication and transcription, for example, can be from an endogenous cellular template, a vector, a plasmid construct or otherwise. The functions of RNA to be interfered with can include functions such as translocation of the RNA to a site of protein translation, translocation of the RNA to sites within the cell which are distant from the site of RNA synthesis, translation of protein from the RNA, splicing of the RNA to yield one or more RNA species, and catalytic activity or complex formation involving the RNA which may be engaged in or facilitated by the RNA. One preferred result of such interference with target nucleic acid function is modulation of the expression of STAT 6. In the context of the present invention, "modulation" and "modulation of expression" mean either an increase (stimulation) or a decrease (inhibition) in the amount or levels of a nucleic acid molecule encoding the gene, e.g., DNA or RNA. Inhibition is often the preferred form of modulation of expression and mRNA is often a preferred target nucleic acid.

In the context of this invention, "hybridization" means the pairing of complementary strands of oligomeric compounds. In the present invention, the preferred mechanism of pairing involves hydrogen bonding, which may be Watson-Crick, Hoogsteen or reversed Hoogsteen hydrogen bonding, between complementary nucleoside or nucleotide bases (nucleobases) of the strands of oligomeric compounds. For example, adenine and thymine are complementary nucleobases which pair through the formation of hydrogen bonds. Hybridization can occur under varying circumstances.

An antisense compound is specifically hybridizable when binding of the compound to the target nucleic acid interferes with the normal function of the target nucleic acid to cause a loss of activity, and there is a sufficient degree of complementarity to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays.

In the present invention the phrase "stringent hybridization conditions" or "stringent conditions" refers to conditions under which a compound of the invention will hybridize to its target sequence, but to a minimal number of other sequences. Stringent conditions are sequence-dependent and will be different in different circumstances and in the context of this invention, "stringent conditions" under which oligomeric compounds hybridize to a target sequence are determined by the nature and composition of the oligomeric compounds and the assays in which they are being investigated.

"Complementary," as used herein, refers to the capacity for precise pairing between two nucleobases of an oligomeric compound. For example, if a nucleobase at a certain position of an oligonucleotide (an oligomeric compound), is capable of hydrogen bonding with a nucleobase at a certain position of a target nucleic acid, said target nucleic acid being a DNA, RNA, or oligonucleotide molecule, then the position of hydrogen bonding between the oligonucleotide and the target nucleic acid is considered to be a complementary position. The oligonucleotide and the further DNA, RNA, or oligonucleotide molecule are complementary to each other when a sufficient number of complementary positions in each molecule are occupied by nucleobases which can hydrogen bond with each other. Thus, "specifically hybridizable" and "complementary" are terms which are used to indicate a sufficient degree of precise pairing or complementarity over a sufficient number of nucleobases such that stable and specific binding occurs between the oligonucleotide and a target nucleic acid.

It is understood in the art that the sequence of an antisense compound need not be 100% complementary to that of its target nucleic acid to be specifically hybridizable. Moreover, an oligonucleotide may hybridize over one or more segments such that intervening or adjacent segments are not involved in the hybridization event (e.g., a loop structure or hairpin structure). It is preferred that the antisense compounds of the present invention comprise at least 70% sequence complementarity to a target region within the target nucleic acid, more preferably that they comprise 90% sequence complementarity and even more preferably comprise 95% sequence complementarity to the target region within the target nucleic acid sequence to which they are targeted. For example, an antisense compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., *J. Mol. Biol.*, 1990, 215, 403-410; Zhang and Madden, Genome Res., 1997, 7, 649-656).

B. Compounds of the Invention

According to the present invention, compounds include antisense oligomeric compounds, antisense oligonucleotides, ribozymes, external guide sequence (EGS) oligonucleotides, alternate splicers, primers, probes, and other oligomeric compounds which hybridize to at least a portion of the target nucleic acid. As such, these compounds may be introduced in the form of single-stranded, double-stranded, circular or hairpin oligomeric compounds and may contain structural elements such as internal or terminal bulges or loops. Once introduced to a system, the compounds of the invention may elicit the action of one or more enzymes or structural proteins to effect modification of the target nucleic acid.

One non-limiting example of such an enzyme is RNAse H, a cellular endonuclease which cleaves the RNA strand of an RNA:DNA duplex. It is known in the art that single-stranded antisense compounds which are "DNA-like" elicit RNAse H. Activation of RNase H, therefore, results in cleavage of the RNA target, thereby greatly enhancing the efficiency of oligonucleotide-mediated inhibition of gene expression. Similar roles have been postulated for other ribonucleases such as those in the RNase III and ribonuclease L family of enzymes.

While the preferred form of antisense compound is a single-stranded antisense oligonucleotide, in many species the introduction of double-stranded structures, such as double-stranded RNA (dsRNA) molecules, has been shown to induce potent and specific antisense-mediated reduction of the function of a gene or its associated gene products. This phenomenon occurs in both plants and animals and is believed to have an evolutionary connection to viral defense and transposon silencing.

The first evidence that dsRNA could lead to gene silencing in animals came in 1995 from work in the nematode, *Caenorhabditis elegans* (Guo and Kempheus, *Cell*, 1995, 81, 611-620).

Montgomery et al. have shown that the primary interference effects of dsRNA are posttranscriptional (Montgomery et al., *Proc. Natl. Acad. Sci. USA*, 1998, 95, 15502-15507). The posttranscriptional antisense mechanism defined in *Caenorhabditis elegans* resulting from exposure to double-stranded RNA (dsRNA) has since been designated RNA interference (RNAi). This term has been generalized to mean antisense-mediated gene silencing involving the introduction of dsRNA leading to the sequence-specific reduction of endogenous targeted mRNA levels (Fire et al., *Nature*, 1998, 391, 806-811). Recently, it has been shown that it is, in fact, the single-stranded RNA oligomers of antisense polarity of the dsRNAs which are the potent inducers of RNAi (Tijsterman et al., *Science*, 2002, 295, 694-697).

In the context of this invention, the term "oligomeric compound" refers to a polymer or oligomer comprising a plurality of monomeric units. In the context of this invention, the term "oligonucleotide" refers to an oligomer or polymer of ribonucleic acid (RNA) or deoxyribonucleic acid (DNA) or mimetics, chimeras, analogs and homologs thereof. This term includes oligonucleotides composed of naturally occurring nucleobases, sugars and covalent internucleoside (backbone) linkages as well as oligonucleotides having non-naturally occurring portions which function similarly. Such modified or substituted oligonucleotides are often preferred over native forms because of desirable properties such as, for example, enhanced cellular uptake, enhanced affinity for a target nucleic acid and increased stability in the presence of nucleases.

While oligonucleotides are a preferred form of the compounds of this invention, the present invention comprehends other families of compounds as well, including but not limited to oligonucleotide analogs and mimetics such as those described herein.

The compounds in accordance with this invention preferably comprise from about 8 to about 80 nucleobases (i.e. from about 8 to about 80 linked nucleosides). One of ordinary skill in the art will appreciate that the invention embodies compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleobases in length.

In one preferred embodiment, the compounds of the invention are 12 to 50 nucleobases in length. One having ordinary skill in the art will appreciate that this embodies compounds of 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleobases in length.

In another preferred embodiment, the compounds of the invention are 15 to 30 nucleobases in length. One having ordinary skill in the art will appreciate that this embodies compounds of 15, 16, 17, 18, 19, 20, 21, 22, 23, 24, 25, 26, 27, 28, 29, or 30 nucleobases in length.

Particularly preferred compounds are oligonucleotides from about 12 to about 50 nucleobases, even more preferably those comprising from about 15 to about 30 nucleobases.

Antisense compounds 8-80 nucleobases in length comprising a stretch of at least eight (8) consecutive nucleobases selected from within the illustrative antisense compounds are considered to be suitable antisense compounds as well.

Exemplary preferred antisense compounds include oligonucleotide sequences that comprise at least the 8 consecutive nucleobases from the 5'-terminus of one of the illustrative preferred antisense compounds (the remaining nucleobases being a consecutive stretch of the same oligonucleotide beginning immediately upstream of the 5'-terminus of the antisense compound which is specifically hybridizable to the target nucleic acid and continuing until the oligonucleotide contains about 8 to about 80 nucleobases). Similarly preferred antisense compounds are represented by oligonucleotide sequences that comprise at least the 8 consecutive nucleobases from the 3'-terminus of one of the illustrative preferred antisense compounds (the remaining nucleobases being a consecutive stretch of the same oligonucleotide beginning immediately downstream of the 3'-terminus of the antisense compound which is specifically hybridizable to the target nucleic acid and continuing until the oligonucleotide contains about 8 to about 80 nucleobases). One having skill in the art armed with the preferred antisense compounds illustrated herein will be able, without undue experimentation, to identify further preferred antisense compounds.

C. Targets of the Invention

"Targeting" an antisense compound to a particular nucleic acid molecule, in the context of this invention, can be a multistep process. The process usually begins with the identification of a target nucleic acid whose function is to be modulated. This target nucleic acid may be, for example, a cellular gene (or mRNA transcribed from the gene) whose expression is associated with a particular disorder or disease state, or a nucleic acid molecule from an infectious agent. In the present invention, the target nucleic acid encodes STAT 6.

The targeting process usually also includes determination of at least one target region, segment, or site within the target nucleic acid for the antisense interaction to occur such that the desired effect, e.g., modulation of expression, will result. Within the context of the present invention, the term "region" is defined as a portion of the target nucleic acid having at least one identifiable structure, function, or characteristic. Within regions of target nucleic acids are segments.

"Segments" are defined as smaller or sub-portions of regions within a target nucleic acid. "Sites," as used in the present invention, are defined as positions within a target nucleic acid.

Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA transcribed from a gene encoding STAT 6, regardless of the sequence(s) of such codons. It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively).

The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. Consequently, the "start codon region" (or "translation initiation codon region") and the "stop codon region" (or "translation termination codon region") are all regions which may be targeted effectively with the antisense compounds of the present invention.

The open reading frame (ORF) or "coding region," which is known in the art to refer to the region between the translation initiation codon and the translation termination codon, is also a region which may be targeted effectively. Within the context of the present invention, a preferred region is the intragenic region encompassing the translation initiation or termination codon of the open reading frame (ORF) of a gene.

Other target regions include the 5' untranslated region (5'UTR), known in the art to refer to the portion of an mRNA in the 5' direction from the translation initiation codon, and thus including nucleotides between the 5' cap site and the translation initiation codon of an mRNA (or corresponding nucleotides on the gene), and the 3' untranslated region (3'UTR), known in the art to refer to the portion of an mRNA in the 3' direction from the translation termination codon, and thus including nucleotides between the translation termination codon and 3' end of an mRNA (or corresponding nucleotides on the gene). The 5' cap site of an mRNA comprises an N7-methylated guanosine residue joined to the 5'-most residue of the mRNA via a 5'-5' triphosphate linkage. The 5'cap region of an mRNA is considered to include the 5' cap structure itself as well as the first 50 nucleotides adjacent to the cap site. It is also preferred to target the 5' cap region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. Targeting splice sites, i.e., intron-exon junctions or exon-intron junctions, may also be particularly useful in situations where aberrant splicing is implicated in disease, or where an overproduction of a particular splice product is implicated in disease. Aberrant fusion junctions due to rearrangements or deletions are also preferred target sites. mRNA transcripts produced via the process of splicing of two (or more) mRNAs from different gene sources are known as "fusion transcripts". It is also known that introns can be effectively targeted using antisense compounds targeted to, for example, DNA or pre-mRNA.

It is also known in the art that alternative RNA transcripts can be produced from the same genomic region of DNA. These alternative transcripts are generally known as "variants". More specifically, "pre-mRNA variants" are transcripts produced from the same genomic DNA that differ from other transcripts produced from the same genomic DNA in either their start or stop position and contain both intronic and exonic sequence.

Upon excision of one or more exon or intron regions, or portions thereof during splicing, pre-mRNA variants produce smaller "mRNA variants". Consequently, mRNA variants are processed pre-mRNA variants and each unique pre-mRNA variant must always produce a unique mRNA variant as a result of splicing. These mRNA variants are also known as "alternative splice variants". If no splicing of the pre-mRNA variant occurs then the pre-mRNA variant is identical to the mRNA variant.

It is also known in the art that variants can be produced through the use of alternative signals to start or stop transcription and that pre-mRNAs and mRNAs can possess more that one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites. Within the context of the invention, the types of variants described herein are also preferred target nucleic acids.

The locations on the target nucleic acid to which the preferred antisense compounds hybridize are hereinbelow referred to as "preferred target segments." As used herein the term "preferred target segment" is defined as at least an 8-nucleobase portion of a target region to which an active antisense compound is targeted. While not wishing to be bound by theory, it is presently believed that these target segments represent portions of the target nucleic acid which are accessible for hybridization.

While the specific sequences of certain preferred target segments are set forth herein, one of skill in the art will recognize that these serve to illustrate and describe particular embodiments within the scope of the present invention. Additional preferred target segments may be identified by one having ordinary skill.

Target segments 8-80 nucleobases in length comprising a stretch of at least eight (8) consecutive nucleobases selected from within the illustrative preferred target segments are considered to be suitable for targeting as well.

Target segments can include DNA or RNA sequences that comprise at least the 8 consecutive nucleobases from the 5'-terminus of one of the illustrative preferred target segments (the remaining nucleobases being a consecutive stretch of the same DNA or RNA beginning immediately upstream of the 5'-terminus of the target segment and continuing until the DNA or RNA contains about 8 to about 80 nucleobases). Similarly preferred target segments are represented by DNA or RNA sequences that comprise at least the 8 consecutive nucleobases from the 3'-terminus of one of the illustrative preferred target segments (the remaining nucleobases being a consecutive stretch of the same DNA or RNA beginning immediately downstream of the 3'-terminus of the target segment and continuing until the DNA or RNA contains about 8 to about 80 nucleobases). One having skill in the art armed with the preferred target segments illustrated herein will be able, without undue experimentation, to identify further preferred target segments.

Once one or more target regions, segments or sites have been identified, antisense compounds are chosen which are sufficiently complementary to the target, i.e., hybridize sufficiently well and with sufficient specificity, to give the desired effect.

D. Screening and Target Validation

In a further embodiment, the "preferred target segments" identified herein may be employed in a screen for additional compounds that modulate the expression of STAT 6. "Modulators" are those compounds that decrease or increase the expression of a nucleic acid molecule encoding STAT 6 and which comprise at least an 8-nucleobase portion which is complementary to a preferred target segment. The screening method comprises the steps of contacting a preferred target segment of a nucleic acid molecule encoding STAT 6 with one or more candidate modulators, and selecting for one or more candidate modulators which decrease or increase the expression of a nucleic acid molecule encoding STAT 6. Once it is shown that the candidate modulator or modulators are capable of modulating (e.g. either decreasing or increasing) the expression of a nucleic acid molecule encoding STAT 6, the modulator may then be employed in further investigative studies of the function of STAT 6, or for use as a research, diagnostic, or therapeutic agent in accordance with the present invention.

The preferred target segments of the present invention may be also be combined with their respective complementary antisense compounds of the present invention to form stabilized double-stranded (duplexed) oligonucleotides.

Such double stranded oligonucleotide moieties have been shown in the art to modulate target expression and regulate translation as well as RNA processing via an antisense mechanism. Moreover, the double-stranded moieties may be subject to chemical modifications (Fire et al., *Nature*, 1998, 391, 806-811; Timmons and Fire, Nature 1998, 395, 854; Timmons et al., *Gene*, 2001, 263, 103-112; Tabara et al., *Science*, 1998, 282, 430-431; Montgomery et al., *Proc. Natl. Acad. Sci. USA*, 1998, 95, 15502-15507; Tuschl et al., *Genes Dev.*, 1999, 13, 3191-3197; Elbashir et al., *Nature*, 2001, 411, 494-498; Elbashir et al., *Genes Dev.* 2001, 15, 188-200). For example, such double-stranded moieties have been shown to inhibit the target by the classical hybridization of antisense strand of the duplex to the target, thereby triggering enzymatic degradation of the target (Tijsterman et al., *Science*, 2002, 295, 694-697).

The compounds of the present invention can also be applied in the areas of drug discovery and target validation. The present invention comprehends the use of the compounds and preferred target segments identified herein in drug discovery efforts to elucidate relationships that exist between STAT 6 and a disease state, phenotype, or condition. These methods include detecting or modulating STAT 6 comprising contacting a sample, tissue, cell, or organism with the compounds of the present invention, measuring the nucleic acid or protein level of STAT 6 and/or a related phenotypic or chemical endpoint at some time after treatment, and optionally comparing the measured value to a non-treated sample or sample treated with a further compound of the invention. These methods can also be performed in parallel or in combination with other experiments to determine the function of unknown genes for the process of target validation or to determine the validity of a particular gene product as a target for treatment or prevention of a particular disease, condition, or phenotype.

E. Kits, Research Reagents, Diagnostics, and Therapeutics

The compounds of the present invention can be utilized for diagnostics, therapeutics, prophylaxis and as research reagents and kits. Furthermore, antisense oligonucleotides, which are able to inhibit gene expression with exquisite specificity, are often used by those of ordinary skill to elucidate the function of particular genes or to distinguish between functions of various members of a biological pathway.

For use in kits and diagnostics, the compounds of the present invention, either alone or in combination with other compounds or therapeutics, can be used as tools in differential and/or combinatorial analyses to elucidate expression patterns of a portion or the entire complement of genes expressed within cells and tissues.

As one nonlimiting example, expression patterns within cells or tissues treated with one or more antisense compounds are compared to control cells or tissues not treated with antisense compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds which affect expression patterns.

Examples of methods of gene expression analysis known in the art include DNA arrays or microarrays (Brazma and Vilo, *FEBS Lett.,* 2000, 480, 17-24; Celis, et al., *FEBS Lett.,* 2000, 480, 2-16), SAGE (serial analysis of gene expression) (Madden, et al., *Drug Discov. Today,* 2000, 5, 415-425), READS (restriction enzyme amplification of digested cDNAs) (Prashar and Weissman, *Methods Enzymol.,* 1999, 303, 258-72), TOGA (total gene expression analysis) (Sutcliffe, et al., *Proc. Natl. Acad. Sci. U.S.A.,* 2000, 97, 1976-81), protein arrays and proteomics (Celis, et al., *FEBS Lett.,* 2000, 480, 2-16; Jungblut, et al., *Electrophoresis,* 1999, 20, 2100-10), expressed sequence tag (EST) sequencing (Celis, et al., *FEBS Lett.,* 2000, 480, 2-16; Larsson, et al., *J. Biotechnol.,* 2000, 80, 143-57), subtractive RNA fingerprinting (SuRF) (Fuchs, et al., *Anal. Biochem.,* 2000, 286, 91-98; Larson, et al., *Cytometry,* 2000, 41, 203-208), subtractive cloning, differential display (DD) (Jurecic and Belmont, *Curr. Opin. Microbiol.,* 2000, 3, 316-21), comparative genomic hybridization (Carulli, et al., *J. Cell Biochem. Suppl.,* 1998, 31, 286-96), FISH (fluorescent in situ hybridization) techniques (Going and Gusterson, *Eur. J. Cancer,* 1999, 35, 1895-904) and mass spectrometry methods (To, *Comb. Chem. High Throughput Screen,* 2000, 3, 235-41).

The compounds of the invention are useful for research and diagnostics, because these compounds hybridize to nucleic acids encoding STAT 6. For example, oligonucleotides that are shown to hybridize with such efficiency and under such conditions as disclosed herein as to be effective STAT 6 inhibitors will also be effective primers or probes under conditions favoring gene amplification or detection, respectively. These primers and probes are useful in methods requiring the specific detection of nucleic acid molecules encoding STAT 6 and in the amplification of said nucleic acid molecules for detection or for use in further studies of STAT 6. Hybridization of the antisense oligonucleotides, particularly the primers and probes, of the invention with a nucleic acid encoding STAT 6 can be detected by means known in the art. Such means may include conjugation of an enzyme to the oligonucleotide, radiolabelling of the oligonucleotide or any other suitable detection means. Kits using such detection means for detecting the level of STAT 6 in a sample may also be prepared.

The specificity and sensitivity of antisense is also harnessed by those of skill in the art for therapeutic uses. Antisense compounds have been employed as therapeutic moieties in the treatment of disease states in animals, including humans. Antisense oligonucleotide drugs, including ribozymes, have been safely and effectively administered to humans and numerous clinical trials are presently underway. It is thus established that antisense compounds can be useful therapeutic modalities that can be configured to be useful in treatment regimes for the treatment of cells, tissues and animals, especially humans.

For therapeutics, an animal, preferably a human, suspected of having a disease or disorder which can be treated by modulating the expression of STAT 6 is treated by administering antisense compounds in accordance with this invention. For example, in one non-limiting embodiment, the methods comprise the step of administering to the animal in need of treatment, a therapeutically effective amount of a STAT 6 inhibitor. The STAT 6 inhibitors of the present invention effectively inhibit the activity of the STAT 6 protein or inhibit the expression of the STAT 6 protein. In one embodiment, the activity or expression of STAT 6 in an animal is inhibited by about 10%. Preferably, the activity or expression of STAT 6 in an animal is inhibited by about 30%. More preferably, the activity or expression of STAT 6 in an animal is inhibited by 50% or more.

For example, the reduction of the expression of STAT 6 may be measured in serum, adipose tissue, liver or any other body fluid, tissue or organ of the animal. Preferably, the cells contained within said fluids, tissues or organs being analyzed contain a nucleic acid molecule encoding STAT 6 protein and/or the STAT 6 protein itself.

The compounds of the invention can be utilized in pharmaceutical compositions by adding an effective amount of a compound to a suitable pharmaceutically acceptable diluent or carrier. Use of the compounds and methods of the invention may also be useful prophylactically.

F. Modifications

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound, however, linear compounds are generally preferred. In addition, linear compounds may have internal nucleobase complementarity and may therefore fold in a manner as to produce a fully or partially double-stranded compound. Within oligonucleotides, the phosphate groups are commonly referred to as forming the internucleoside backbone of the oligonucleotide. The normal linkage or backbone of RNA and DNA is a 3' to 5' phosphodiester linkage.

Modified Internucleoside Linkages (Backbones)

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, certain of which are commonly owned with this application, and each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

Modified Sugar and Internucleoside Linkages-Mimetics

In other preferred oligonucleotide mimetics, both the sugar and the internucleoside linkage (i.e. the backbone), of the nucleotide units are replaced with novel groups. The nucleobase units are maintained for hybridization with an appropriate target nucleic acid. One such compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., *Science*, 1991, 254, 1497-1500.

Preferred embodiments of the invention are oligonucleotides with phosphorothioate backbones and oligonucleosides with heteroatom backbones, and in particular —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified Sugars

Modified oligonucleotides may also contain one or more substituted sugar moieties. Preferred oligonucleotides comprise one of the following at the 2' position: OH; F; O—, S—, or N-alkyl; O—, S—, or N-alkenyl; O—, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are O[($CH_2$)$_n$O]$_m$$CH_3$, O($CH_2$)$_n$O$CH_3$, O($CH_2$)$_n$$NH_2$, O($CH_2$)$_n$$CH_3$, O($CH_2$)$_n$$ONH_2$, and O($CH_2$)$_n$ON[($CH_2$)$_n$$CH_3$]$_2$, where n and m are from 1 to about 10. Other preferred oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—$CH_2CH_2OCH_3$, also known as 2'-O-(2-methoxyethyl) or 2'-MOE) (Martin et al., *Helv. Chim. Acta*, 1995, 78, 486-504) i.e., an alkoxyalkoxy group. A further preferred modification includes 2'-dimethylaminooxyethoxy, i.e., a O($CH_2$)$_2$ON($CH_3$)$_2$ group, also known as 2'-DMAOE, as described in examples hereinbelow, and 2'-dimethylaminoethoxyethoxy (also known in the art as 2'-O-dimethyl-amino-ethoxy-ethyl or 2'-DMAEOE), i.e., 2'-O—$CH_2$—O—$CH_2$—N($CH_3$)$_2$, also described in examples hereinbelow.

Other preferred modifications include 2'-methoxy (2'-O—$CH_3$), 2'-aminopropoxy (2'-O$CH_2CH_2CH_2NH_2$), 2'-allyl (2'-$CH_2$—CH=$CH_2$), 2'-O-allyl (2'-O—$CH_2$—CH=$CH_2$) and 2'-fluoro (2'-F). The 2'-modification may be in the arabino (up) position or ribo (down) position. A preferred 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, certain of which are commonly owned with the instant application, and each of which is herein incorporated by reference in its entirety.

A further preferred modification of the sugar includes Locked Nucleic Acids (LNAs) in which the 2'-hydroxyl group is linked to the 3' or 4' carbon atom of the sugar ring, thereby forming a bicyclic sugar moiety. The linkage is preferably a methylene (—$CH_2$—)$_n$ group bridging the 2' oxygen atom and the 4' carbon atom wherein n is 1 or 2. LNAs and preparation thereof are described in WO 98/39352 and WO 99/14226.

Natural and Modified Nucleobases

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido [5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858-859, Kroschwitz, J. I., ed. John Wiley & Sons, 1990, those disclosed by Englisch et al., *Angewandte Chemie, International Edition*, 1991, 30, 613, and those disclosed by Sanghvi, Y. S., Chapter 15, *Antisense Research and Applications*, pages 289-302, Crooke, S. T. and Lebleu, B., ed., CRC Press, 1993. Certain of these nucleobases are particularly useful for increasing the binding affinity of the compounds of the invention. These include 5-substituted pyrimidines, 6-azapyrimidines and N2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,830,653; 5,763,588; 6,005,096; and 5,681,941, certain of which are commonly owned with the instant application, and each of which is herein incorporated by reference, and U.S. Pat. No. 5,750,692, which is commonly owned with the instant application and also herein incorporated by reference.

Conjugates

Another modification of the oligonucleotides of the invention involves chemically linking to the oligonucleotide one or more moieties or conjugates which enhance the activity, cellular distribution or cellular uptake of the oligonucleotide. These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenan-thridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application PCT/US92/09196, filed Oct. 23, 1992, and U.S. Pat. No. 6,287,860, the entire disclosure of which are incorporated herein by reference. Conjugate moieties include but are not limited to lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxycholesterol moiety. Oligonucleotides of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999) which is incorporated herein by reference in its entirety.

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, certain of which are commonly owned with the instant application, and each of which is herein incorporated by reference.

Chimeric Compounds

It is not necessary for all positions in a given compound to be uniformly modified, and in fact more than one of the aforementioned modifications may be incorporated in a single compound or even at a single nucleoside within an oligonucleotide.

The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, increased stability and/or increased binding affinity for the target nucleic acid. An additional region of the oligonucleotide may serve as a substrate for enzymes capable of cleaving RNA:DNA or RNA:RNA hybrids. By way of example, RNAse H is a cellular endonuclease which cleaves the RNA strand of an RNA:DNA duplex. Activation of RNase H, therefore, results in cleavage of the RNA target, thereby greatly enhancing the efficiency of oligonucleotide-mediated inhibition of gene expression. The cleavage of RNA:RNA hybrids can, in like fashion, be accomplished through the actions of endoribonucleases, such as RNAseL which cleaves both cellular and viral RNA. Cleavage of the RNA target can be routinely detected by gel electrophoresis and, if necessary, associated nucleic acid hybridization techniques known in the art.

Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety.

G. Formulations

The compounds of the invention may also be admixed, encapsulated, conjugated or otherwise associated with other molecules, molecule structures or mixtures of compounds, as for example, liposomes, receptor-targeted molecules, oral, rectal, topical or other formulations, for assisting in uptake, distribution and/or absorption. Representative United States patents that teach the preparation of such uptake, distribution and/or absorption-assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

The antisense compounds of the invention encompass any pharmaceutically acceptable salts, esters, or salts of such esters, or any other compound which, upon administration to an animal, including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents. The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl)phosphate] derivatives according to the methods disclosed in WO 93/24510 to Gosselin et al., published Dec. 9, 1993 or in WO 94/26764 and U.S. Pat. No. 5,770,713 to Imbach et al.

The term "pharmaceutically acceptable salts" refers to physiologically and pharmaceutically acceptable salts of the compounds of the invention: i.e., salts that retain the desired biological activity of the parent compound and do not impart undesired toxicological effects thereto. For oligonucleotides, preferred examples of pharmaceutically acceptable salts and their uses are further described in U.S. Pat. No. 6,287,860, which is incorporated herein in its entirety.

The present invention also includes pharmaceutical compositions and formulations which include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

Pharmaceutical compositions of the present invention include, but are not limited to, solutions, emulsions, foams and liposome-containing formulations. The pharmaceutical compositions and formulations of the present invention may comprise one or more penetration enhancers, carriers, excipients or other active or inactive ingredients.

Emulsions are typically heterogenous systems of one liquid dispersed in another in the form of droplets usually exceeding 0.1 μm in diameter. Emulsions may contain additional components in addition to the dispersed phases, and the active drug which may be present as a solution in either the aqueous phase, oily phase or itself as a separate phase. Microemulsions are included as an embodiment of the present invention. Emulsions and their uses are well known in the art and are further described in U.S. Pat. No. 6,287,860, which is incorporated herein in its entirety.

Formulations of the present invention include liposomal formulations. As used in the present invention, the term "liposome" means a vesicle composed of amphiphilic lipids arranged in a spherical bilayer or bilayers. Liposomes are unilamellar or multilamellar vesicles which have a membrane formed from a lipophilic material and an aqueous interior that contains the composition to be delivered. Cationic liposomes are positively charged liposomes which are believed to interact with negatively charged DNA molecules to form a stable complex. Liposomes that are pH-sensitive or negatively-charged are believed to entrap DNA rather than complex with it. Both cationic and noncationic liposomes have been used to deliver DNA to cells.

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860, which is incorporated herein in its entirety.

The pharmaceutical formulations and compositions of the present invention may also include surfactants. The use of surfactants in drug products, formulations and in emulsions is well known in the art. Surfactants and their uses are further described in U.S. Pat. No. 6,287,860, which is incorporated herein in its entirety.

In one embodiment, the present invention employs various penetration enhancers to effect the efficient delivery of nucleic acids, particularly oligonucleotides. In addition to aiding the diffusion of non-lipophilic drugs across cell membranes, penetration enhancers also enhance the permeability of lipophilic drugs. Penetration enhancers may be classified as belonging to one of five broad categories, i.e., surfactants, fatty acids, bile salts, chelating agents, and non-chelating non-surfactants. Penetration enhancers and their uses are further described in U.S. Pat. No. 6,287,860, which is incorporated herein in its entirety.

One of skill in the art will recognize that formulations are routinely designed according to their intended use, i.e. route of administration.

Preferred formulations for topical administration include those in which the oligonucleotides of the invention are in admixture with a topical delivery agent such as lipids, liposomes, fatty acids, fatty acid esters, steroids, chelating agents and surfactants. Preferred lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA).

For topical or other administration, oligonucleotides of the invention may be encapsulated within liposomes or may form complexes thereto, in particular to cationic liposomes. Alternatively, oligonucleotides may be complexed to lipids, in particular to cationic lipids. Preferred fatty acids and esters, pharmaceutically acceptable salts thereof, and their uses are further described in U.S. Pat. No. 6,287,860, which is incorporated herein in its entirety. Topical formulations are described in detail in U.S. patent application Ser. No. 09/315,298 filed on May 20, 1999, which is incorporated herein by reference in its entirety.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Preferred oral formulations are those in which oligonucleotides of the invention are administered in conjunction with one or more penetration enhancers surfactants and chelators. Preferred surfactants include fatty acids and/or esters or salts thereof, bile acids and/or salts thereof. Preferred bile acids/salts and fatty acids and their uses are further described in U.S. Pat. No. 6,287,860, which is incorporated herein in its entirety. Also preferred are combinations of penetration enhancers, for example, fatty acids/salts in combination with bile acids/salts. A particularly preferred combination is the sodium salt of lauric acid, capric acid and UDCA. Further penetration enhancers include polyoxyethylene-9-lauryl ether, polyoxyethylene-20-cetyl ether. Oligonucleotides of the invention may be delivered orally, in granular form including sprayed dried particles, or complexed to form micro or nanoparticles. Oligonucleotide complexing agents and their uses are further described in U.S. Pat. No. 6,287,860, which is incorporated herein in its entirety. Oral formulations for oligonucleotides and their preparation are described in detail in U.S. application Ser. Nos. 09/108,673 (filed Jul. 1, 1998), 09/315,298 (filed May 20, 1999) and 10/071,822, filed Feb. 8, 2002, each of which is incorporated herein by reference in their entirety.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Certain embodiments of the invention provide pharmaceutical compositions containing one or more oligomeric compounds and one or more other chemotherapeutic agents which function by a non-antisense mechanism. Examples of such chemotherapeutic agents include but are not limited to cancer chemotherapeutic drugs such as daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). When used with the compounds of the invention, such chemo-therapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. Combinations of antisense compounds and other non-antisense drugs are also within the scope of this invention. Two or more combined compounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. Alternatively, compositions of the invention may contain two or more antisense compounds targeted to different regions of the same nucleic acid target. Numerous examples of antisense compounds are known in the art. Two or more combined compounds may be used together or sequentially.

H. Dosing

The formulation of therapeutic compositions and their subsequent administration (dosing) is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.01 ug to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 ug to 100 g per kg of body weight, once or more daily, to once every 20 years.

While the present invention has been described with specificity in accordance with certain of its preferred embodiments, the following examples serve only to illustrate the invention and are not intended to limit the same.

EXAMPLES

Example 1

Synthesis of Nucleoside Phosphoramidites

The following compounds, including amidites and their intermediates were prepared as described in U.S. Pat. No. 6,426,220 and published PCT WO 02/36743; 5'-O-Dimethoxytrityl-thymidine intermediate for 5-methyl dC amidite, 5'-O-Dimethoxytrityl-2'-deoxy-5-methylcytidine intermediate for 5-methyl-dC amidite, 5'-O-Dimethoxytrityl-2'-deoxy-N4-benzoyl-5-methylcytidine penultimate intermediate for 5-methyl dC amidite, [5'-O-(4,4'-Dimethoxytriphenylmethyl)-2'-deoxy-$N^4$-benzoyl-5-methylcytidin-3'-O-yl]-2-cyanoethyl-N,N-diisopropylphosphoramidite (5-methyl dC amidite), 2'-Fluorodeoxyadenosine, 2'-Fluorodeoxyguanosine, 2'-Fluorouridine, 2'-Fluorodeoxycytidine, 2'-O-(2-Methoxyethyl) modified amidites, 2'-O-(2-methoxyethyl)-5-methyluridine intermediate, 5'-O-DMT-2'-O-(2-methoxyethyl)-5-methyluridine penultimate intermediate, [5'-O-(4,4'-Dimethoxytriphenylmethyl)-2'-O-(2-methoxyethyl)-5-methyluridin-3'-O-yl]-2-cyanoethyl-N,N-diisopropylphosphoramidite (MOE T amidite), 5'-O-Dimethoxytrityl-2'-O-(2-methoxyethyl)-5-methyleytidine intermediate, 5'-O-dimethoxytrityl-2'-O-(2-methoxyethyl)-$N^4$-benzoyl-5-methyl-cytidine penultimate intermediate, [5'-O-(4,4'-Dimethoxytriphenylmethyl)-2'-O-(2-methoxyethyl)-$N^4$-benzoyl-5-methylcytidin-3'-O-yl]-2-cyanoethyl-N,N-diisopropylphosphoramidite (MOE 5-Me-C amidite), [5'-O-(4,4'-Dimethoxytriphenylmethyl)-2'-O-(2-methoxyethyl)-$N^6$-benzoyladenosin-3'-O-yl]-2-cyanoethyl-N,N-diisopropylphosphoramidite (MOE A amdite), [5'-O-(4,4'-Dimethoxytriphenylmethyl)-2'-O-(2-methoxyethyl)-$N^4$-isobutyrylguanosin-3'-O-yl]-2-cyanoethyl-N,N-diisopropylphosphoramidite (MOE G amidite), 2'-O-(Aminooxyethyl)nucleoside amidites and 2'-O-(dimethylaminooxyethyl)nucleoside amidites, 2'-(Dimethylaminooxyethoxy)nucleoside amidites, 5'-O-tert-Butyldiphenylsilyl-$O^2$-2'-anhydro-5-methyluridine, 5'-O-tert-Butyldiphenylsilyl-2'-O-(2-hydroxyethyl)-5-methyluridine, 2'-O-([2-phthalimidoxy)ethyl]-5'-t-butyldiphenylsilyl-5-methyluridine, 5'-O-tert-butyldiphenylsilyl-2'-O-[(2-formadoximinooxy)ethyl]-5-methyluridine, 5'-O-tert-Butyldiphenylsilyl-2'-O-[N,N dimethylaminooxyethyl]-5-methyluridine, 2'-O-(dimethylaminooxyethyl)-5-methyluridine, 5'-O-DMT-2'-O-(dimethylaminooxyethyl)-5-methyluridine, 5'-O-DMT-2'-O-(2-N,N-dimethylaminooxyethyl)-5-methyluridine-3'-[(2-cyanoethyl)-N,N-diisopropylphosphoramidite], 2'-(Aminooxyethoxy) nucleoside amidites, N2-isobutyryl-6-O-diphenylcarbamoyl-2'-O-(2-ethylacetyl)-5'-O-(4,4'-dimethoxytrityl)guanosine-3'-[(2-cyanoethyl)-N,N-diisopropylphosphoramidite], 2'-dimethylaminoethoxyethoxy (2'-DMAEOE) nucleoside amidites, 2'-O-[2(2-N,N-dimethylaminoethoxy)ethyl]-5-methyl uridine, 5'-O-dimethoxytrityl-2'-O-[2(2-N,N-dimethylaminoethoxy)-ethyl)]-5-methyl uridine and 5'-O-Dimethoxytrityl-2'-O-[2(2-N,N-dimethylaminoethoxy)-ethyl)]-5-methyl uridine-3'-O-(cyanoethyl-N,N-diisopropyl) phosphoramidite.

Example 2

Oligonucleotide and Oligonucleoside Synthesis

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

Oligonucleotides: Unsubstituted and substituted phosphodiester (P=O) oligonucleotides are synthesized on an automated DNA synthesizer (Applied Biosystems model 394) using standard phosphoramidite chemistry with oxidation by iodine.

Phosphorothioates (P=S) are synthesized similar to phosphodiester oligonucleotides with the following exceptions: thiation was effected by utilizing a 10% w/v solution of 3,H-1,2-benzodithiole-3-one 1,1-dioxide in acetonitrile for the oxidation of the phosphite linkages. The thiation reaction step time was increased to 180 sec and preceded by the normal capping step. After cleavage from the CPG column and deblocking in concentrated ammonium hydroxide at 55° C. (12-16 hr), the oligonucleotides were recovered by precipitating with >3 volumes of ethanol from a 1 M $NH_4OAc$ solution. Phosphinate oligonucleotides are prepared as described in U.S. Pat. No. 5,508,270, herein incorporated by reference.

Alkyl phosphonate oligonucleotides are prepared as described in U.S. Pat. No. 4,469,863, herein incorporated by reference.

3'-Deoxy-3'-methylene phosphonate oligonucleotides are prepared as described in U.S. Pat. No. 5,610,289 or 5,625,050, herein incorporated by reference.

Phosphoramidite oligonucleotides are prepared as described in U.S. Pat. No. 5,256,775 or U.S. Pat. No. 5,366,878, herein incorporated by reference.

Alkylphosphonothioate oligonucleotides are prepared as described in published PCT applications PCT/US94/00902 and PCT/US93/06976 (published as WO 94/17093 and WO 94/02499, respectively), herein incorporated by reference.

3'-Deoxy-3'-amino phosphoramidate oligonucleotides are prepared as described in U.S. Pat. No. 5,476,925, herein incorporated by reference.

Phosphotriester oligonucleotides are prepared as described in U.S. Pat. No. 5,023,243, herein incorporated by reference.

Borano phosphate oligonucleotides are prepared as described in U.S. Pat. Nos. 5,130,302 and 5,177,198, both herein incorporated by reference.

Oligonucleosides: Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone compounds having, for instance, alternating MMI and P=O or P=S linkages are prepared as described in U.S. Pat. Nos. 5,378,825, 5,386,023, 5,489,677, 5,602,240 and 5,610,289, all of which are herein incorporated by reference.

Formacetal and thioformacetal linked oligonucleosides are prepared as described in U.S. Pat. Nos. 5,264,562 and 5,264,564, herein incorporated by reference.

Ethylene oxide linked oligonucleosides are prepared as described in U.S. Pat. No. 5,223,618, herein incorporated by reference.

Example 3

RNA Synthesis

In general, RNA synthesis chemistry is based on the selective incorporation of various protecting groups at strategic intermediary reactions. Although one of ordinary skill in the art will understand the use of protecting groups in organic synthesis, a useful class of protecting groups includes silyl ethers. In particular bulky silyl ethers are used to protect the 5'-hydroxyl in combination with an acid-labile orthoester protecting group on the 2'-hydroxyl. This set of protecting groups is then used with standard solid-phase synthesis technology. It is important to lastly remove the acid labile orthoester protecting group after all other synthetic steps. Moreover, the early use of the silyl protecting groups during synthesis ensures facile removal when desired, without undesired deprotection of 2' hydroxyl.

Following this procedure for the sequential protection of the 5'-hydroxyl in combination with protection of the 2'-hydroxyl by protecting groups that are differentially removed and are differentially chemically labile, RNA oligonucleotides were synthesized.

RNA oligonucleotides are synthesized in a stepwise fashion. Each nucleotide is added sequentially (3'- to 5'-direction) to a solid support-bound oligonucleotide. The first nucleoside at the 3'-end of the chain is covalently attached to a solid support. The nucleotide precursor, a ribonucleoside phosphoramidite, and activator are added, coupling the second base onto the 5'-end of the first nucleoside. The support is washed and any unreacted 5'-hydroxyl groups are capped with acetic anhydride to yield 5'-acetyl moieties. The linkage is then oxidized to the more stable and ultimately desired P(V) linkage. At the end of the nucleotide addition cycle, the 5'-silyl group is cleaved with fluoride. The cycle is repeated for each subsequent nucleotide.

Following synthesis, the methyl protecting groups on the phosphates are cleaved in 30 minutes utilizing 1 M disodium-2-carbamoyl-2-cyanoethylene-1,1-dithiolate trihydrate ($S_2Na_2$) in DMF. The deprotection solution is washed from the solid support-bound oligonucleotide using water. The support is then treated with 40% methylamine in water for 10 minutes at 55° C. This releases the RNA oligonucleotides into solution, deprotects the exocyclic amines, and modifies the 2'-groups. The oligonucleotides can be analyzed by anion exchange HPLC at this stage.

The 2'-orthoester groups are the last protecting groups to be removed. The ethylene glycol monoacetate orthoester protecting group developed by Dharmacon Research, Inc. (Lafayette, Colo.), is one example of a useful orthoester protecting group which, has the following important properties. It is stable to the conditions of nucleoside phosphoramidite synthesis and oligonucleotide synthesis. However, after oligonucleotide synthesis the oligonucleotide is treated with methylamine which not only cleaves the oligonucleotide from the solid support but also removes the acetyl groups from the orthoesters. The resulting 2-ethyl-hydroxyl substituents on the orthoester are less electron withdrawing than the acetylated precursor. As a result, the modified orthoester becomes more labile to acid-catalyzed hydrolysis. Specifically, the rate of cleavage is approximately 10 times faster after the acetyl groups are removed. Therefore, this orthoester possesses sufficient stability in order to be compatible with oligonucleotide synthesis and yet, when subsequently modified, permits deprotection to be carried out under relatively mild aqueous conditions compatible with the final RNA oligonucleotide product.

Additionally, methods of RNA synthesis are well known in the art (Scaringe, S. A. Ph.D. Thesis, University of Colorado, 1996; Scaringe, S. A., et al., *J. Am. Chem. Soc.,* 1998, 120, 11820-11821; Matteucci, M. D. and Caruthers, M. H. *J. Am. Chem. Soc.,* 1981, 103, 3185-3191; Beaucage, S. L. and Caruthers, M. H. *Tetrahedron Lett.,* 1981, 22, 1859-1862; Dahl, B. J., et al., *Acta Chem. Scand.* 1990, 44, 639-641; Reddy, M. P., et al., *Tetrahedrom Lett.,* 1994, 25, 4311-4314; Wincott, F. et al., *Nucleic Acids Res.,* 1995, 23, 2677-2684; Griffin, B. E., et al., *Tetrahedron,* 1967, 23, 2301-2313; Griffin, B. E., et al., *Tetrahedron,* 1967, 23, 2315-2331).

RNA antisense compounds (RNA oligonucleotides) of the present invention can be synthesized by the methods herein or purchased from Dharmacon Research, Inc (Lafayette, Colo.). Once synthesized, complementary RNA antisense compounds can then be annealed by methods known in the art to form double stranded (duplexed) antisense compounds. For example, duplexes can be formed by combining 30 µl of each of the complementary strands of RNA oligonucleotides (50 uM RNA oligonucleotide solution) and 15 µl of 5× annealing buffer (100 mM potassium acetate, 30 mM HEPES-KOH pH 7.4, 2 mM magnesium acetate) followed by heating for 1 minute at 90° C., then 1 hour at 37° C. The resulting duplexed antisense compounds can be used in kits, assays, screens, or other methods to investigate the role of a target nucleic acid.

Example 4

Synthesis of Chimeric Oligonucleotides

Chimeric oligonucleotides, oligonucleosides or mixed oligonucleotides/oligonucleosides of the invention can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. Oligonucleotides of the second type are also known in the art as "hemimers" or "wingmers".

[2'-O-Me]-[2'-deoxy]-[2'-O-Me] Chimeric Phosphorothioate Oligonucleotides

Chimeric oligonucleotides having 2'-O-alkyl phosphorothioate and 2'-deoxy phosphorothioate oligonucleotide segments are synthesized using an Applied Biosystems automated DNA synthesizer Model 394, as above. Oligonucleotides are synthesized using the automated synthesizer and 2'-deoxy-5'-dimethoxytrityl-3'-O-phosphoramidite for the DNA portion and 5'-dimethoxytrityl-2'-O-methyl-3'-O-phosphoramidite for 5' and 3' wings. The standard synthesis cycle is modified by incorporating coupling steps with increased reaction times for the 5'-dimethoxytrityl-2'-O-methyl-3'-O-phosphoramidite. The fully protected oligonucleotide is cleaved from the support and deprotected in concentrated ammonia (NH₄OH) for 12-16 hr at 55° C. The deprotected oligo is then recovered by an appropriate method (precipitation, column chromatography, volume reduced in vacuo and analyzed spetrophotometrically for yield and for purity by capillary electrophoresis and by mass spectrometry.

[2'-O-(2-Methoxyethyl)]-[2'-deoxy]-[2'-O-(Methoxyethyl)] Chimeric Phosphorothioate Oligonucleotides

[2'-O-(2-methoxyethyl)]-[2'-deoxy]-[-2'-O-(methoxyethyl)] chimeric phosphorothioate oligonucleotides were prepared as per the procedure above for the 2'-O-methyl chimeric oligonucleotide, with the substitution of 2'-O-(methoxyethyl)amidites for the 2'-O-methyl amidites.

[2'-O-(2-Methoxyethyl)Phosphodiester]-[2'-deoxy Phosphorothioate]-[2'-O-(2-Methoxyethyl)Phosphodiester] Chimeric Oligonucleotides

[2'-O-(2-methoxyethyl phosphodiester]-[2'-deoxy phosphorothioate]-[2'-O-(methoxyethyl)phosphodiester] chimeric oligonucleotides are prepared as per the above procedure for the 2'-O-methyl chimeric oligonucleotide with the substitution of 2'-O-(methoxyethyl)amidites for the 2'-O-methyl amidites, oxidation with iodine to generate the phosphodiester internucleotide linkages within the wing portions of the chimeric structures and sulfurization utilizing 3,H-1,2 benzodithiole-3-one 1,1 dioxide (Beaucage Reagent) to generate the phosphorothioate internucleotide linkages for the center gap.

Other chimeric oligonucleotides, chimeric oligonucleosides and mixed chimeric oligonucleotides/oligonucleosides are synthesized according to U.S. Pat. No. 5,623,065, herein incorporated by reference.

Example 5

Design and Screening of Duplexed Antisense Compounds Targeting STAT 6

In accordance with the present invention, a series of nucleic acid duplexes comprising the antisense compounds of the present invention and their complements can be designed to target STAT 6. The nucleobase sequence of the antisense strand of the duplex comprises at least a portion of an oligonucleotide in Table 1. The ends of the strands may be modified by the addition of one or more natural or modified nucleobases to form an overhang. The sense strand of the dsRNA is then designed and synthesized as the complement of the antisense strand and may also contain modifications or additions to either terminus. For example, in one embodiment, both strands of the dsRNA duplex would be complementary over the central nucleobases, each having overhangs at one or both termini.

For example, a duplex comprising an antisense strand having the sequence CGAGAGGCGGACGGGACCG (SEQ ID NO: 139) and having a two-nucleobase overhang of deoxythymidine(dT) would have the following structure:

```
cgagaggcggacgggaccgTT  Antisense Strand  (Seq ID NO: 140)
|||||||||||||||||||
TTgctctccgcctgccctggc  Complement        (SEQ ID NO: 141)
```

RNA strands of the duplex can be synthesized by methods disclosed herein or purchased from Dharmacon Research Inc., (Lafayette, Colo.). Once synthesized, the complementary strands are annealed. The single strands are aliquoted and diluted to a concentration of 50 uM. Once diluted, 30 uL of each strand is combined with 15 uL of a 5× solution of annealing buffer. The final concentration of said buffer is 100 mM potassium acetate, 30 mM HEPES-KOH pH 7.4, and 2 mM magnesium acetate. The final volume is 75 uL. This solution is incubated for 1 minute at 90° C. and then centrifuged for 15 seconds. The tube is allowed to sit for 1 hour at 37° C. at which time the dsRNA duplexes are used in experimentation. The final concentration of the dsRNA duplex is 20 uM. This solution can be stored frozen (−20° C.) and freeze-thawed up to 5 times.

Once prepared, the duplexed antisense compounds are evaluated for their ability to modulate STAT 6 expression.

When cells reached 80% confluency, they are treated with duplexed antisense compounds of the invention. For cells grown in 96-well plates, wells are washed once with 200 μL OPTI-MEM-1 reduced-serum medium (Gibco BRL) and then treated with 130 μL of OPTI-MEM-1 containing 12 μg/mL LIPOFECTIN (Gibco BRL) and the desired duplex antisense compound at a final concentration of 200 nM. After 5 hours of treatment, the medium is replaced with fresh medium. Cells are harvested 16 hours after treatment, at which time RNA is isolated and target reduction measured by RT-PCR.

Example 6

Oligonucleotide Isolation

After cleavage from the controlled pore glass solid support and deblocking in concentrated ammonium hydroxide at 55° C. for 12-16 hours, the oligonucleotides or oligonucleosides are recovered by precipitation out of 1 M $NH_4OAc$ with >3 volumes of ethanol. Synthesized oligonucleotides were analyzed by electrospray mass spectroscopy (molecular weight determination) and by capillary gel electrophoresis and judged to be at least 70% full length material. The relative amounts of phosphorothioate and phosphodiester linkages obtained in the synthesis was determined by the ratio of correct molecular weight relative to the −16 amu product (+/−32+/−48). For some studies oligonucleotides were purified by HPLC, as described by Chiang et al., *J. Biol. Chem.* 1991, 266, 18162-18171. Results obtained with HPLC-purified material were similar to those obtained with non-HPLC purified material.

Example 7

Oligonucleotide Synthesis

96 Well Plate Format

Oligonucleotides were synthesized via solid phase P(III) phosphoramidite chemistry on an automated synthesizer capable of assembling 96 sequences simultaneously in a 96-well format. Phosphodiester internucleotide linkages were afforded by oxidation with aqueous iodine. Phosphorothioate internucleotide linkages were generated by sulfurization utilizing 3,H-1,2 benzodithiole-3-one 1,1 dioxide (Beaucage Reagent) in anhydrous acetonitrile. Standard base-protected beta-cyanoethyl-diiso-propyl phosphoramidites were purchased from commercial vendors (e.g. PE-Applied Biosystems, Foster City, Calif., or Pharmacia, Piscataway, N.J.). Non-standard nucleosides are synthesized as per standard or patented methods. They are utilized as base protected beta-cyanoethyldiisopropyl phosphoramidites.

Oligonucleotides were cleaved from support and deprotected with concentrated $NH_4OH$ at elevated temperature (55-60° C.) for 12-16 hours and the released product then dried in vacuo. The dried product was then re-suspended in sterile water to afford a master plate from which all analytical and test plate samples are then diluted utilizing robotic pipettors.

Example 8

Oligonucleotide Analysis

96-Well Plate Format

The concentration of oligonucleotide in each well was assessed by dilution of samples and UV absorption spectroscopy. The full-length integrity of the individual products was evaluated by capillary electrophoresis (CE) in either the 96-well format (Beckman P/ACE™ MDQ) or, for individually prepared samples, on a commercial CE apparatus (e.g., Beckman P/ACE™ 5000, ABI 270). Base and backbone composition was confirmed by mass analysis of the compounds utilizing electrospray-mass spectroscopy. All assay test plates were diluted from the master plate using single and multi-channel robotic pipettors. Plates were judged to be acceptable if at least 85% of the compounds on the plate were at least 85% full length.

Example 9

Cell Culture and Oligonucleotide Treatment

The effect of antisense compounds on target nucleic acid expression can be tested in any of a variety of cell types provided that the target nucleic acid is present at measurable levels. This can be routinely determined using, for example, PCR or Northern blot analysis. The following cell types are provided for illustrative purposes, but other cell types can be routinely used, provided that the target is expressed in the cell type chosen. This can be readily determined by methods routine in the art, for example Northern blot analysis, ribonuclease protection assays, or RT-PCR.

T-24 Cells:

The human transitional cell bladder carcinoma cell line T-24 was obtained from the American Type Culture Collection (ATCC) (Manassas, Va.). T-24 cells were routinely cultured in complete McCoy's 5A basal media (Invitrogen Corporation, Carlsbad, Calif.) supplemented with 10% fetal calf serum (Invitrogen Corporation, Carlsbad, Calif.), penicillin 100 units per mL, and streptomycin 100 micrograms per mL (Invitrogen Corporation, Carlsbad, Calif.). Cells were routinely passaged by trypsinization and dilution when they reached 90% confluence. Cells were seeded into 96-well plates (Falcon-Primaria #353872) at a density of 7000 cells/well for use in RT-PCR analysis.

For Northern blotting or other analysis, cells may be seeded onto 100 mm or other standard tissue culture plates and treated similarly, using appropriate volumes of medium and oligonucleotide.

A549 Cells:

The human lung carcinoma cell line A549 was obtained from the American Type Culture Collection (ATCC) (Manassas, Va.). A549 cells were routinely cultured in DMEM basal media (Invitrogen Corporation, Carlsbad, Calif.) supplemented with 10% fetal calf serum (Invitrogen Corporation, Carlsbad, Calif.), penicillin 100 units per mL, and streptomycin 100 micrograms per mL (Invitrogen Corporation, Carlsbad, Calif.). Cells were routinely passaged by trypsinization and dilution when they reached 90% confluence.

NHDF cells:

Human neonatal dermal fibroblast (NHDF) were obtained from the Clonetics Corporation (Walkersville, Md.). NHDFs were routinely maintained in Fibroblast Growth Medium (Clonetics Corporation, Walkersville, Md.) supplemented as recommended by the supplier. Cells were maintained for up to 10 passages as recommended by the supplier.

HEK Cells:

Human embryonic keratinocytes (HEK) were obtained from the Clonetics Corporation (Walkersville, Md.). HEKs were routinely maintained in Keratinocyte Growth Medium (Clonetics Corporation, Walkersville, Md.) formulated as recommended by the supplier. Cells were routinely maintained for up to 10 passages as recommended by the supplier.

Treatment with Antisense Compounds:

When cells reached 65-75% confluency, they were treated with oligonucleotide. For cells grown in 96-well plates, wells were washed once with 100 μL OPTI-MEM™-1 reduced-serum medium (Invitrogen Corporation, Carlsbad, Calif.) and then treated with 130 μL of OPTI-MEM™-1 containing 3.75

µg/mL LIPOFECTIN™ (Invitrogen Corporation, Carlsbad, Calif.) and the desired concentration of oligonucleotide. Cells are treated and data are obtained in triplicate. After 4-7 hours of treatment at 37° C., the medium was replaced with fresh medium. Cells were harvested 16-24 hours after oligonucleotide treatment.

The concentration of oligonucleotide used varies from cell line to cell line. To determine the optimal oligonucleotide concentration for a particular cell line, the cells are treated with a positive control oligonucleotide at a range of concentrations. For human cells the positive control oligonucleotide is selected from either ISIS 13920 (TCCGTCATCGCTCCT-CAGGG, SEQ ID NO: 1) which is targeted to human H-ras, or ISIS 18078, (GTGCGCGCGAGCCCGAAATC, SEQ ID NO: 2) which is targeted to human Jun-N-terminal kinase-2 (JNK2). Both controls are 2'-O-methoxyethyl gapmers (2'-O-methoxyethyls shown in bold) with a phosphorothioate backbone. For mouse or rat cells the positive control oligonucleotide is ISIS 15770, ATGCATTCTGCCCCCAAGGA, SEQ ID NO: 3, a 2'-O-methoxyethyl gapmer (2'-O-methoxyethyls shown in bold) with a phosphorothioate backbone which is targeted to both mouse and rat c-raf. The concentration of positive control oligonucleotide that results in 80% inhibition of c-H-ras (for ISIS 13920), JNK2 (for ISIS 18078) or c-raf (for ISIS 15770) mRNA is then utilized as the screening concentration for new oligonucleotides in subsequent experiments for that cell line. If 80% inhibition is not achieved, the lowest concentration of positive control oligonucleotide that results in 60% inhibition of c-H-ras, JNK2 or c-raf mRNA is then utilized as the oligonucleotide screening concentration in subsequent experiments for that cell line. If 60% inhibition is not achieved, that particular cell line is deemed as unsuitable for oligonucleotide transfection experiments. The concentrations of antisense oligonucleotides used herein are from 50 nM to 300 nM.

Example 10

Analysis of Oligonucleotide Inhibition of STAT 6 Expression

Antisense modulation of STAT 6 expression can be assayed in a variety of ways known in the art. For example, STAT 6 mRNA levels can be quantitated by, e.g., Northern blot analysis, competitive polymerase chain reaction (PCR), or real-time PCR (RT-PCR). Real-time quantitative PCR is presently preferred. RNA analysis can be performed on total cellular RNA or poly(A)+ mRNA. The preferred method of RNA analysis of the present invention is the use of total cellular RNA as described in other examples herein. Methods of RNA isolation are well known in the art. Northern blot analysis is also routine in the art. Real-time quantitative (PCR) can be conveniently accomplished using the commercially available ABI PRISM™ 7600, 7700, or 7900 Sequence Detection System, available from PE-Applied Biosystems, Foster City, Calif. and used according to manufacturer's instructions.

Protein levels of STAT 6 can be quantitated in a variety of ways well known in the art, such as immunoprecipitation, Western blot analysis (immunoblotting), enzyme-linked immunosorbent assay (ELISA) or fluorescence-activated cell sorting (FACS). Antibodies directed to STAT 6 can be identified and obtained from a variety of sources, such as the MSRS catalog of antibodies (Aerie Corporation, Birmingham, Mich.), or can be prepared via conventional monoclonal or polyclonal antibody generation methods well known in the art.

Example 11

Design of Phenotypic Assays and In Vivo Studies for the Use of STAT 6 Inhibitors Phenotypic Assays Once STAT 6 inhibitors have been identified by the methods disclosed herein, the compounds are further investigated in one or more phenotypic assays, each having measurable endpoints predictive of efficacy in the treatment of a particular disease state or condition. Phenotypic assays, kits and reagents for their use are well known to those skilled in the art and are herein used to investigate the role and/or association of STAT 6 in health and disease. Representative phenotypic assays, which can be purchased from any one of several commercial vendors, include those for determining cell viability, cytotoxicity, proliferation or cell survival (Molecular Probes, Eugene, Oreg.; PerkinElmer, Boston, Mass.), protein-based assays including enzymatic assays (Panvera, LLC, Madison, Wis.; BD Biosciences, Franklin Lakes, N.J.; Oncogene Research Products, San Diego, Calif.), cell regulation, signal transduction, inflammation, oxidative processes and apoptosis (Assay Designs Inc., Ann Arbor, Mich.), triglyceride accumulation (Sigma-Aldrich, St. Louis, Mo.), angiogenesis assays, tube formation assays, cytokine and hormone assays and metabolic assays (Chemicon International Inc., Temecula, Calif.; Amersham Biosciences, Piscataway, N.J.).

In one non-limiting example, cells determined to be appropriate for a particular phenotypic assay (i.e., MCF-7 cells selected for breast cancer studies; adipocytes for obesity studies) are treated with STAT 6 inhibitors identified from the in vitro studies as well as control compounds at optimal concentrations which are determined by the methods described above. At the end of the treatment period, treated and untreated cells are analyzed by one or more methods specific for the assay to determine phenotypic outcomes and endpoints.

Phenotypic endpoints include changes in cell morphology over time or treatment dose as well as changes in levels of cellular components such as proteins, lipids, nucleic acids, hormones, saccharides or metals. Measurements of cellular status which include pH, stage of the cell cycle, intake or excretion of biological indicators by the cell, are also endpoints of interest.

Analysis of the genotype of the cell (measurement of the expression of one or more of the genes of the cell) after treatment is also used as an indicator of the efficacy or potency of the STAT 6 inhibitors. Hallmark genes, or those genes suspected to be associated with a specific disease state, condition, or phenotype, are measured in both treated and untreated cells.

In Vivo Studies

The individual subjects of the in vivo studies described herein are warm-blooded vertebrate animals, which includes humans.

The clinical trial is subjected to rigorous controls to ensure that individuals are not unnecessarily put at risk and that they are fully informed about their role in the study. To account for the psychological effects of receiving treatments, volunteers are randomly given placebo or STAT 6 inhibitor. Furthermore, to prevent the doctors from being biased in treatments, they are not informed as to whether the medication they are administering is a STAT 6 inhibitor or a placebo. Using this randomization approach, each volunteer has the same chance of being given either the new treatment or the placebo.

Volunteers receive either the STAT 6 inhibitor or placebo for eight week period with biological parameters associated with the indicated disease state or condition being measured at the beginning (baseline measurements before any treatment), end (after the final treatment), and at regular intervals during the study period. Such measurements include the levels of nucleic acid molecules encoding STAT 6 or STAT 6 protein levels in body fluids, tissues or organs compared to pre-treatment levels. Other measurements include, but are not limited to, indices of the disease state or condition being treated, body weight, blood pressure, serum titers of pharmacologic indicators of disease or toxicity as well as ADME (absorption, distribution, metabolism and excretion) measurements.

Information recorded for each patient includes age (years), gender, height (cm), family history of disease state or condition (yes/no), motivation rating (some/moderate/great) and number and type of previous treatment regimens for the indicated disease or condition.

Volunteers taking part in this study are healthy adults (age 18 to 65 years) and roughly an equal number of males and females participate in the study. Volunteers with certain characteristics are equally distributed for placebo and STAT 6 inhibitor treatment. In general, the volunteers treated with placebo have little or no response to treatment, whereas the volunteers treated with the STAT 6 inhibitor show positive trends in their disease state or condition index at the conclusion of the study.

Example 12

RNA Isolation

Poly(A)+ mRNA Isolation

Poly(A)+ mRNA was isolated according to Miura et al., (*Clin. Chem.*, 1996, 42, 1758-1764). Other methods for poly (A)+ mRNA isolation are routine in the art. Briefly, for cells grown on 96-well plates, growth medium was removed from the cells and each well was washed with 200 μL cold PBS. 60 μL lysis buffer (10 mM Tris-HCl, pH 7.6, 1 mM EDTA, 0.5 M NaCl, 0.5% NP-40, 20 mM vanadyl-ribonucleoside complex) was added to each well, the plate was gently agitated and then incubated at room temperature for five minutes. 55 μL of lysate was transferred to Oligo d(T) coated 96-well plates (AGCT Inc., Irvine Calif.). Plates were incubated for 60 minutes at room temperature, washed 3 times with 200 μL of wash buffer (10 mM Tris-HCl pH 7.6, 1 mM EDTA, 0.3 M NaCl). After the final wash, the plate was blotted on paper towels to remove excess wash buffer and then air-dried for 5 minutes. 60 μL of elution buffer (5 mM Tris-HCl pH 7.6), preheated to 70° C., was added to each well, the plate was incubated on a 90° C. hot plate for 5 minutes, and the eluate was then transferred to a fresh 96-well plate.

Cells grown on 100 mm or other standard plates may be treated similarly, using appropriate volumes of all solutions.
Total RNA Isolation Total RNA was isolated using an RNEASY 96™ kit and buffers purchased from Qiagen Inc. (Valencia, Calif.) following the manufacturer's recommended procedures. Briefly, for cells grown on 96-well plates, growth medium was removed from the cells and each well was washed with 200 μL cold PBS. 150 μL Buffer RLT was added to each well and the plate vigorously agitated for 20 seconds. 150 μL of 70% ethanol was then added to each well and the contents mixed by pipetting three times up and down. The samples were then transferred to the RNEASY 96™ well plate attached to a QIAVAC™ manifold fitted with a waste collection tray and attached to a vacuum source. Vacuum was applied for 1 minute. 500 μL of Buffer RW1 was added to each well of the RNEASY 96™ plate and incubated for 15 minutes and the vacuum was again applied for 1 minute. An additional 500 μL of Buffer RW1 was added to each well of the RNEASY 96™ plate and the vacuum was applied for 2 minutes. 1 mL of Buffer RPE was then added to each well of the RNEASY 96™ plate and the vacuum applied for a period of 90 seconds. The Buffer RPE wash was then repeated and the vacuum was applied for an additional 3 minutes. The plate was then removed from the QIAVAC™ manifold and blotted dry on paper towels. The plate was then re-attached to the QIAVAC™ manifold fitted with a collection tube rack containing 1.2 mL collection tubes. RNA was then eluted by pipetting 140 μL of RNAse free water into each well, incubating 1 minute, and then applying the vacuum for 3 minutes.

The repetitive pipetting and elution steps may be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

Example 13

Real-time Quantitative PCR Analysis of STAT 6 mRNA Levels

Quantitation of STAT 6 mRNA levels was accomplished by real-time quantitative PCR using the ABI PRISM™ 7600, 7700, or 7900 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., FAM or JOE, obtained from either PE-Applied Biosystems, Foster City, Calif., Operon Technologies Inc., Alameda, Calif. or Integrated DNA Technologies Inc., Coralville, Iowa) is attached to the 5' end of the probe and a quencher dye (e.g., TAMRA, obtained from either PE-Applied Biosystems, Foster City, Calif., Operon Technologies Inc., Alameda, Calif. or Integrated DNA Technologies Inc., Coralville, Iowa) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art. PCR reagents were obtained from Invitrogen Corporation, (Carlsbad, Calif.). RT-PCR reactions were carried out by adding 20 µL PCR cocktail (2.5×PCR buffer minus MgCl$_2$, 6.6 mM MgCl$_2$, 375 µM each of dATP, dCTP, dCTP and dGTP, 375 nM each of forward primer and reverse primer, 125 nM of probe, 4 Units RNAse inhibitor, 1.25 Units PLATINUM® Taq, 5 Units MuLV reverse transcriptase, and 2.5×ROX dye) to 96-well plates containing 30 µL total RNA solution (20-200 ng). The RT reaction was carried out by incubation for 30 minutes at 48° C. Following a 10 minute incubation at 95° C. to activate the PLATINUM® Taq, 40 cycles of a two-step PCR protocol were carried out: 95° C. for 15 seconds (denaturation) followed by 60° C. for 1.5 minutes (annealing/extension).

Gene target quantities obtained by real time RT-PCR are normalized using either the expression level of GAPDH, a gene whose expression is constant, or by quantifying total RNA using RiboGreen™ (Molecular Probes, Inc. Eugene, Oreg.). GAPDH expression is quantified by real time RT-PCR, by being run simultaneously with the target, multiplexing, or separately. Total RNA is quantified using RiboGreen™ RNA quantification reagent (Molecular Probes, Inc. Eugene, Oreg.). Methods of RNA quantification by RiboGreen™ are taught in Jones, L. J., et al, (*Analytical Biochemistry*, 1998, 265, 368-374).

In this assay, 170 µL of RiboGreen™ working reagent (RiboGreen™ reagent diluted 1:350 in 10 mM Tris-HCl, 1 mM EDTA, pH 7.5) is pipetted into a 96-well plate containing 30 µL purified, cellular RNA. The plate is read in a CytoFluor 4000 (PE Applied Biosystems) with excitation at 485 nm and emission at 530 nm.

Probes and primers to human STAT 6 were designed to hybridize to a human STAT 6 sequence, using published sequence information (GenBank accession number NM_003153.1, incorporated herein as SEQ ID NO:4). For human STAT 6 the PCR primers were: forward primer: CCAAACGCTGTCTCCGGA (SEQ ID NO: 5) reverse primer: GCTAGTAACGTACTGTTTGCTGATGAA (SEQ ID NO: 6) and the PCR probe was: FAM-CTACTGGTCT-GACCGGCTGATCATTGG-TAMRA (SEQ ID NO: 7) where FAM is the fluorescent dye and TAMRA is the quencher dye. For human GAPDH the PCR primers were: forward primer: GAAGGTGAAGGTCGGAGTC(SEQ ID NO:8) reverse primer: GAAGATGGTGATGGGATTTC (SEQ ID NO:9) and the PCR probe was: 5' JOE-CAAGCT-TCCCGTTCTCAGCC-TAMRA 3' (SEQ ID NO: 10) where JOE is the fluorescent reporter dye and TAMRA is the quencher dye.

Example 14

Northern Blot Analysis of STAT 6 mRNA Levels

Eighteen hours after antisense treatment, cell monolayers were washed twice with cold PBS and lysed in 1 mL RNA-ZOL™ (TEL-TEST "B" Inc., Friendswood, Tex.). Total RNA was prepared following manufacturer's recommended protocols. Twenty micrograms of total RNA was fractionated by electrophoresis through 1.2% agarose gels containing 1.1% formaldehyde using a MOPS buffer system (AMRESCO, Inc. Solon, Ohio). RNA was transferred from the gel to HYBONDT™-N+ nylon membranes (Amersham Pharmacia Biotech, Piscataway, N.J.) by overnight capillary transfer using a Northern/Southern Transfer buffer system (TEL-TEST "B" Inc., Friendswood, Tex.). RNA transfer was confirmed by UV visualization. Membranes were fixed by UV cross-linking using a STRATALINKER™ UV Crosslinker 2400 (Stratagene, Inc, La Jolla, Calif.) and then probed using QUICKHYB™ hybridization solution (Stratagene, La Jolla, Calif.) using manufacturer's recommendations for stringent conditions.

To detect human STAT 6, a human STAT 6 specific probe was prepared by PCR using the forward primer CCAAACGCTGTCTCCGGA (SEQ ID NO: 5) and the reverse primer GCTAGTAACGTACTGTTTGCTGATGAA (SEQ ID NO: 6). To normalize for variations in loading and transfer efficiency membranes were stripped and probed for human glyceraldehyde-3-phosphate dehydrogenase (GAPDH) RNA (Clontech, Palo Alto, Calif.).

Hybridized membranes were visualized and quantitated using a PHOSPHORIMAGER™ and IMAGEQUANT™ Software V3.3 (Molecular Dynamics, Sunnyvale, Calif.). Data was normalized to GAPDH levels in untreated controls.

Example 15

Antisense Inhibition of Human STAT 6 Expression by Chimeric Phosphorothioate Oligonucleotides Having 2'-MOE Wings and a Deoxy Gap In accordance with the present invention, a series of antisense compounds were designed to target different regions of the human STAT 6 RNA, using published sequences (GenBank accession number NM_003153.1, incorporated herein as SEQ ID NO: 4; GenBank accession number BC005823.1, incorporated herein as SEQ ID NO: 11; a genomic sequence of human STAT 6 represented by the complement of residues 157501-174000 of GenBank accession number AC018673.4, incorporated herein as SEQ ID NO: 12; GenBank accession number BE972840.1, the complement of which is incorporated herein as SEQ ID NO: 13; and GenBank accession number BF902909.1, the complement of which is incorporated herein as SEQ ID NO: 14). The compounds are shown in Table 1. "Target site" indicates the first (5'-most) nucleotide number on the particular target sequence to which the compound binds. All compounds in Table 1 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE)nucleotides. The internucleoside (backbone) linkages are phosphorothioate (P=S) throughout the oligonucleotide. All cytidine residues are 5-methylcytidines. The compounds were analyzed for their effect on human STAT 6 mRNA levels by quantitative real-time PCR as described in other examples herein. Data are averages from three experiments in which T-24 cells were treated with the oligonucleotides of the present invention. The positive control for each datapoint is identified in the table by sequence ID number. If present, "N.D." indicates "no data".

TABLE 1

Inhibition of human STAT 6 mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO | CONTROL SEQ ID NO |
|---|---|---|---|---|---|---|---|
| 153765 | Coding | 4 | 1951 | agtgagcgaatggacaggtc | 96 | 15 | 2 |
| 153766 | Coding | 4 | 2483 | cgctgtcactggctggctca | 83 | 16 | 2 |
| 153767 | Coding | 4 | 1171 | ttgatgatttctccagtgct | 92 | 17 | 2 |
| 153768 | Coding | 4 | 940 | aggacttcatccagccggcc | 50 | 18 | 2 |
| 153769 | Coding | 4 | 1054 | cccaggaacctcaagcccaa | 68 | 19 | 2 |
| 153770 | Coding | 4 | 242 | gtcacccagaagatgccgca | 53 | 20 | 2 |
| 153771 | Coding | 4 | 2100 | tttccacggtcatcttgatg | 59 | 21 | 2 |
| 153772 | Coding | 4 | 379 | aagatggtgctcccctcccc | 34 | 22 | 2 |
| 153773 | Coding | 4 | 765 | gccgtttccaaatctggatc | 76 | 23 | 2 |
| 153774 | Coding | 4 | 729 | ctttggctgcctctagctct | 89 | 24 | 2 |
| 153775 | Coding | 4 | 1725 | gtttggtgaggtccaggaca | 89 | 25 | 2 |
| 153776 | Coding | 4 | 2321 | catctgcaggtgaggctcct | 85 | 26 | 2 |
| 153777 | Coding | 4 | 2676 | tggcccttaggtccatgtgg | 76 | 27 | 2 |
| 153778 | Coding | 4 | 1905 | ctatctgtggagagccatcc | 72 | 28 | 2 |
| 153779 | Coding | 4 | 1805 | attgagaagaaggctagtaa | 83 | 29 | 2 |
| 153780 | Coding | 4 | 392 | gctgatgtgttgcaagatgg | 78 | 30 | 2 |
| 153781 | 3'UTR | 4 | 3019 | gccccatcaccctcagagag | 80 | 31 | 2 |
| 153782 | Coding | 4 | 417 | ccctctgatatatgctctca | 73 | 32 | 2 |
| 153783 | Coding | 4 | 1797 | gaaggctagtaacgtactgt | 84 | 33 | 2 |
| 153784 | Coding | 4 | 1819 | gttccgtcgggctcattgag | 92 | 34 | 2 |
| 153785 | Coding | 4 | 2479 | gtcactggctggctcaggca | 87 | 35 | 2 |
| 153786 | Coding | 4 | 1513 | ttcagagtttcacacatctt | 83 | 36 | 2 |
| 153787 | 5'UTR | 4 | 79 | caggccccataggtctgtag | 88 | 37 | 2 |
| 153788 | Coding | 4 | 644 | tatcaagctgtgcagagaca | 80 | 38 | 2 |
| 153789 | Coding | 4 | 272 | caggaactcccagggctggc | 74 | 39 | 2 |
| 153790 | 3'UTR | 4 | 3000 | gctctgtatgtgtgtgtgcg | 90 | 40 | 2 |
| 153791 | Coding | 4 | 1972 | agatcccggattcggtcccc | 88 | 41 | 2 |
| 153792 | Coding | 4 | 794 | cggtgcgccattccctgcca | 94 | 42 | 2 |
| 153793 | Coding | 4 | 1997 | gggatagagattttgagct | 53 | 43 | 2 |
| 153794 | Start Codon | 4 | 146 | gatctgggacttggaggttg | 71 | 44 | 2 |
| 153795 | Coding | 4 | 2165 | tccaaggtcataagaaggca | 88 | 45 | 2 |
| 153796 | Coding | 4 | 1762 | atgatcagccggtcagacca | 84 | 46 | 2 |
| 153797 | Coding | 4 | 1205 | cccaggaatgctgttctcca | 88 | 47 | 2 |
| 153798 | Coding | 4 | 944 | tctcaggacttcatccagcc | 6 | 48 | 2 |
| 153799 | Coding | 4 | 1671 | ccagcaggatctccttgttg | 82 | 49 | 2 |
| 153800 | Coding | 4 | 1160 | tccagtgctttctgctccag | 87 | 50 | 2 |

TABLE 1-continued

Inhibition of human STAT 6 mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO | CONTROL SEQ ID NO |
|---|---|---|---|---|---|---|---|
| 153801 | Coding | 4 | 328 | acagtgtctgaaagtagggc | 50 | 51 | 2 |
| 195427 | 5'UTR | 4 | 39 | gctggccctgctagcacctc | 68 | 52 | 2 |
| 195428 | Start Codon | 4 | 158 | ccacagagacatgatctggg | 79 | 53 | 2 |
| 195429 | Coding | 4 | 541 | gtcttaaacttgagttcttc | 53 | 54 | 2 |
| 195430 | Coding | 4 | 718 | tctagctctccagtggtctc | 78 | 55 | 2 |
| 195431 | Coding | 4 | 1085 | ggccctgaccagcggaggct | 72 | 56 | 2 |
| 195432 | Coding | 4 | 1290 | cctctgtgacagactcagtg | 72 | 57 | 2 |
| 195433 | Coding | 4 | 1615 | tccatactgaggctgttgtc | 20 | 58 | 2 |
| 195434 | Coding | 4 | 1887 | cctggccccggatgacatgg | 53 | 59 | 2 |
| 195435 | Coding | 4 | 2152 | gaaggcaccatggtaggcat | 55 | 60 | 2 |
| 195436 | Coding | 4 | 2506 | ccaatccaagtgccctgagg | 70 | 61 | 2 |
| 195437 | Stop Codon | 4 | 2699 | cagctgggatcaccaactgg | 49 | 62 | 2 |
| 195438 | 3'UTR | 4 | 2944 | gtgtctcagagcctgaactt | 77 | 63 | 2 |
| 195439 | 5'UTR | 11 | 23 | taagcagtggctgccccagc | 51 | 64 | 2 |
| 195440 | 5'UTR | 11 | 38 | cctccctcttcagtgtaagc | 65 | 65 | 2 |
| 195441 | 3'UTR | 11 | 3185 | agaagccttccatgccctaa | 83 | 66 | 2 |
| 195442 | 3'UTR | 11 | 3230 | tatgttcctgcctatccgtc | 76 | 67 | 2 |
| 195443 | 3'UTR | 11 | 3531 | caactaaggtgccagctata | 86 | 68 | 2 |
| 195444 | 3'UTR | 11 | 3539 | tggtcatgcaactaaggtgc | 84 | 69 | 2 |
| 195445 | 3'UTR | 11 | 3585 | atttgtgttgtcacgtaggc | 84 | 70 | 2 |
| 195446 | 3'UTR | 11 | 3599 | tctcaccctcccaaatttgt | 48 | 71 | 2 |
| 195447 | 3'UTR | 11 | 3629 | agcacacttgctgctgtctt | 74 | 72 | 2 |
| 195448 | 3'UTR | 11 | 3779 | gccaggcctggacccagact | 60 | 73 | 2 |
| 195449 | 3'UTR | 11 | 3835 | gggcaacagaaaagatgcag | 50 | 74 | 2 |
| 195450 | Intron | 12 | 2812 | aatgtcagcttttaatctgt | 67 | 75 | 2 |
| 195451 | Intron | 12 | 3082 | gagtcaatgcctgagatggg | 50 | 76 | 2 |
| 195452 | Intron: Exon Junction | 12 | 6200 | caggaagcaactgggagtga | 7 | 77 | 2 |
| 195453 | Exon: Intron Junction | 12 | 8677 | ccatctcagagaaggcattg | 81 | 78 | 2 |
| 195454 | Intron | 12 | 10476 | tgcacatgtccctgtgggat | 64 | 79 | 2 |
| 195455 | Exon: Intron Junction | 12 | 11486 | gggactcaccggtcagacca | 26 | 80 | 2 |
| 195456 | Intron: Exon Junction | 12 | 12582 | agtggttggtccctggagga | 71 | 81 | 2 |

TABLE 1-continued

Inhibition of human STAT 6 mRNA levels by chimeric phosphorothioate oligonucleotides having 2'-MOE wings and a deoxy gap

| ISIS # | TARGET REGION | TARGET SEQ ID NO | TARGET SITE | SEQUENCE | % INHIB | SEQ ID NO | CONTROL SEQ ID NO |
|---|---|---|---|---|---|---|---|
| 195457 | Exon: Intron Junction | 12 | 12691 | agctccttacaccatatctg | 0 | 82 | 2 |
| 195458 | Genomic | 13 | 9 | caaagtgtggaagtgaaagg | 0 | 83 | 2 |
| 195459 | Genomic | 13 | 148 | ctctggtggccacggtggga | 0 | 84 | 2 |
| 195460 | Genomic | 13 | 654 | ggtgtatggctgctcagact | 67 | 85 | 2 |
| 195461 | Genomic | 14 | 66 | aggaggtacatgtgactgac | 23 | 86 | 2 |

As shown in Table 1, SEQ ID NOs: 15, 16, 17, 19, 23, 24, 25, 26, 27, 28, 29, 30, 31, 32, 33, 34, 35, 36, 37, 38, 39, 40, 41, 42, 44, 45, 46, 47, 49, 50, 52, 53, 55, 56, 57, 61, 63, 65, 66, 67, 68, 69, 70, 72, 73, 75, 78, 79, 81 and 85 demonstrated at least 60% inhibition of human STAT 6 expression in this assay and are therefore preferred. More preferred are SEQ ID NOs: 15, 34 and 42. The target regions to which these preferred sequences are complementary are herein referred to as "preferred target segments" and are therefore preferred for targeting by compounds of the present invention. These preferred target segments are shown in Table 2. The sequences represent the reverse complement of the preferred antisense compounds shown in Table 1. "Target site" indicates the first (5'-most) nucleotide number on the particular target nucleic acid to which the oligonucleotide binds. Also shown in Table 2 is the species in which each of the preferred target segments was found.

TABLE 2

Sequence and position of preferred target segments identified in STAT 6

| SITE ID | TARGET SEQ ID NO | TARGET SITE | SEQUENCE | REV COMP OF SEQ ID | ACTIVE IN | SEQ ID NO |
|---|---|---|---|---|---|---|
| 69306 | 4 | 1951 | gacctgtccattcgctcact | 15 | H. sapiens | 87 |
| 69307 | 4 | 2483 | tgagccagccagtgacagcg | 16 | H. sapiens | 88 |
| 69308 | 4 | 1171 | agcactggagaaatcatcaa | 17 | H. sapiens | 89 |
| 69310 | 4 | 1054 | ttgggcttgaggttcctggg | 19 | H. sapiens | 90 |
| 69314 | 4 | 765 | gatccagatttggaaacggc | 23 | H. sapiens | 91 |
| 69315 | 4 | 729 | agagctagaggcagccaaag | 24 | H. sapiens | 92 |
| 69316 | 4 | 1725 | tgtcctggacctcaccaaac | 25 | H. sapiens | 93 |
| 69317 | 4 | 2321 | aggagcctcacctgcagatg | 26 | H. sapiens | 94 |
| 69318 | 4 | 2676 | ccacatggacctaagggcca | 27 | H. sapiens | 95 |
| 69319 | 4 | 1905 | ggatggctctccacagatag | 28 | H. sapiens | 96 |
| 69320 | 4 | 1805 | ttactagccttcttctcaat | 29 | H. sapiens | 97 |
| 69321 | 4 | 392 | ccatcttgcaacacatcagc | 30 | H. sapiens | 98 |
| 69322 | 4 | 3019 | ctctctgagggtgatgggc | 31 | H. sapiens | 99 |
| 69323 | 4 | 417 | tgagagcatatatcagaggg | 32 | H. sapiens | 100 |
| 69324 | 4 | 1797 | acagtacgttactagccttc | 33 | H. sapiens | 101 |
| 69325 | 4 | 1819 | ctcaatgagcccgacggaac | 34 | H. sapiens | 102 |
| 69326 | 4 | 2479 | tgcctgagccagccagtgac | 35 | H. sapiens | 103 |
| 69327 | 4 | 1513 | aagatgtgtgaaactctgaa | 36 | H. sapiens | 104 |

TABLE 2-continued

Sequence and position of preferred target segments identified in STAT 6

| SITE ID | TARGET SEQ ID NO | TARGET SITE | SEQUENCE | REV COMP OF SEQ ID | ACTIVE IN | SEQ ID NO |
|---|---|---|---|---|---|---|
| 69328 | 4 | 79 | ctacagacctatggggcctg | 37 | H. sapiens | 105 |
| 69329 | 4 | 644 | tgtctctgcacagcttgata | 38 | H. sapiens | 106 |
| 69330 | 4 | 272 | gccagccctgggagttcctg | 39 | H. sapiens | 107 |
| 69331 | 4 | 3000 | cgcacacacacatacagagc | 40 | H. sapiens | 108 |
| 69332 | 4 | 1972 | ggggaccgaatccgggatct | 41 | H. sapiens | 109 |
| 69333 | 4 | 794 | tggcagggaatggcgcaccg | 42 | H. sapiens | 110 |
| 69335 | 4 | 146 | caacctccaagtcccagatc | 44 | H. sapiens | 111 |
| 69336 | 4 | 2165 | tgccttcttatgaccttgga | 45 | H. sapiens | 112 |
| 69337 | 4 | 1762 | tggtctgaccggctgatcat | 46 | H. sapiens | 113 |
| 69338 | 4 | 1205 | tggagaacagcattcctggg | 47 | H. sapiens | 114 |
| 69340 | 4 | 1671 | caacaaggagatcctgctgg | 49 | H. sapiens | 115 |
| 69341 | 4 | 1160 | ctggagcagaaagcactgga | 50 | H. sapiens | 116 |
| 113659 | 4 | 39 | gaggtgctagcagggccagc | 52 | H. sapiens | 117 |
| 113660 | 4 | 158 | cccagatcatgtctctgtgg | 53 | H. sapiens | 118 |
| 113662 | 4 | 718 | gagaccactggagagctaga | 55 | H. sapiens | 119 |
| 113663 | 4 | 1085 | agcctccgctggtcagggcc | 56 | H. sapiens | 120 |
| 113664 | 4 | 1290 | cactgagtctgtcacagagg | 57 | H. sapiens | 121 |
| 113668 | 4 | 2506 | cctcagggcacttggattgg | 61 | H. sapiens | 122 |
| 113670 | 4 | 2944 | aagttcaggctctgagacac | 63 | H. sapiens | 123 |
| 113672 | 11 | 38 | gcttacactgaagagggagg | 65 | H. sapiens | 124 |
| 113673 | 11 | 3185 | ttagggcatggaaggcttct | 66 | H. sapiens | 125 |
| 113674 | 11 | 3230 | gacggataggcaggaacata | 67 | H. sapiens | 126 |
| 113675 | 11 | 3531 | tatagctggcaccttagttg | 68 | H. sapiens | 127 |
| 113676 | 11 | 3539 | gcaccttagttgcatgacca | 69 | H. sapiens | 128 |
| 113677 | 11 | 3585 | gcctacgtgacaacacaaat | 70 | H. sapiens | 129 |
| 113679 | 11 | 3629 | aagacagcagcaagtgtgct | 72 | H. sapiens | 130 |
| 113680 | 11 | 3779 | agtctgggtccaggcctggc | 73 | H. sapiens | 131 |
| 113682 | 12 | 2812 | acagattaaaagctgacatt | 75 | H. sapiens | 132 |
| 113685 | 12 | 8677 | caatgccttctctgagatgg | 78 | H. sapiens | 133 |
| 113686 | 12 | 10476 | atcccacagggacatgtgca | 79 | H. sapiens | 134 |
| 113688 | 12 | 12582 | tcctccagggaccaaccact | 81 | H. sapiens | 135 |
| 113692 | 13 | 654 | agtctgagcagccatacacc | 85 | H. sapiens | 136 |

As these "preferred target segments" have been found by experimentation to be open to, and accessible for, hybridization with the antisense compounds of the present invention, one of skill in the art will recognize or be able to ascertain, using no more than routine experimentation, further embodiments of the invention that encompass other compounds that specifically hybridize to these preferred target segments and consequently inhibit the expression of STAT 6.

According to the present invention, antisense compounds include antisense oligomeric compounds, antisense oligonucleotides, ribozymes, external guide sequence (EGS) oligonucleotides, alternate splicers, primers, probes, and other short oligomeric compounds which hybridize to at least a portion of the target nucleic acid.

Example 16

Western Blot Analysis of STAT 6 Protein Levels

Western blot analysis (immunoblot analysis) is carried out using standard methods. Cells are harvested 16-20 h after oligonucleotide treatment, washed once with PBS, suspended in Laemmli buffer (100 ul/well), boiled for 5 minutes and loaded on a 16% SDS-PAGE gel. Gels are run for 1.5 hours at 150 V, and transferred to membrane for western blotting. Appropriate primary antibody directed to STAT 6 is used, with a radiolabeled or fluorescently labeled secondary antibody directed against the primary antibody species. Bands are visualized using a PHOSPHORIMAGER™ (Molecular Dynamics, Sunnyvale Calif.).

Example 17

Targeting of Individual Oligonucleotides to Specific Variants of STAT 6

It is advantageous to selectively inhibit the expression of one or more variants of STAT 6. Consequently, in one embodiment of the present invention are oligonucleotides that selectively target, hybridize to, and specifically inhibit one or more, but fewer than all of the variants of STAT 6. A summary of the target sites of the variants is shown in Table 3 and includes GenBank accession number BC005823.1, representing STAT 6 main mRNA (represented in Table 3 as STAT 6), incorporated herein as SEQ ID NO: 11; GenBank accession number BE972840.1, representing STAT 6d, incorporated herein as SEQ ID NO: 13; GenBank accession number BF902909.1, representing STAT 6e, incorporated herein as SEQ ID NO: 14; GenBank accession number AR204914.1, representing STAT 6b, incorporated herein as SEQ ID NO: 137; and GenBank accession number AR204915.1, representing STAT 6c, incorporated herein as SEQ ID NO: 138.

TABLE 3

Targeting of individual oligonucleotides to specific variants of STAT 6

| ISIS # | OLIGO SEQ ID NO. | TARGET SITE | VARIANT | VARIANT SEQ ID NO. |
|---|---|---|---|---|
| 153765 | 15 | 2066 | STAT 6 | 11 |
| 153765 | 15 | 1932 | STAT 6c | 137 |
| 153765 | 15 | 1741 | STAT 6b | 138 |
| 153766 | 16 | 2597 | STAT 6 | 11 |
| 153766 | 16 | 2464 | STAT 6c | 137 |
| 153766 | 16 | 2273 | STAT 6b | 138 |
| 153767 | 17 | 1286 | STAT 6 | 11 |
| 153767 | 17 | 1236 | STAT 6c | 137 |
| 153767 | 17 | 961 | STAT 6b | 138 |
| 153768 | 18 | 1055 | STAT 6 | 11 |
| 153768 | 18 | 1005 | STAT 6c | 137 |
| 153768 | 18 | 730 | STAT 6b | 138 |
| 153769 | 19 | 1169 | STAT 6 | 11 |
| 153769 | 19 | 1119 | STAT 6c | 137 |
| 153769 | 19 | 844 | STAT 6b | 138 |
| 153770 | 20 | 357 | STAT 6 | 11 |
| 153770 | 20 | 307 | STAT 6c | 137 |
| 153770 | 20 | 171 | STAT 6b | 138 |
| 153771 | 21 | 2215 | STAT 6 | 11 |
| 153771 | 21 | 2081 | STAT 6c | 137 |
| 153771 | 21 | 1890 | STAT 6b | 138 |
| 153772 | 22 | 494 | STAT 6 | 11 |
| 153772 | 22 | 444 | STAT 6c | 137 |
| 153773 | 23 | 880 | STAT 6 | 11 |

TABLE 3-continued

Targeting of individual oligonucleotides to specific variants of STAT 6

| ISIS # | OLIGO SEQ ID NO. | TARGET SITE | VARIANT | VARIANT SEQ ID NO. |
|---|---|---|---|---|
| 153773 | 23 | 830 | STAT 6c | 137 |
| 153773 | 23 | 555 | STAT 6b | 138 |
| 153774 | 24 | 844 | STAT 6 | 11 |
| 153774 | 24 | 794 | STAT 6c | 137 |
| 153774 | 24 | 519 | STAT 6b | 138 |
| 153775 | 25 | 1840 | STAT 6 | 11 |
| 153775 | 25 | 1790 | STAT 6c | 137 |
| 153775 | 25 | 1515 | STAT 6b | 138 |
| 153776 | 26 | 2435 | STAT 6 | 11 |
| 153776 | 26 | 298 | STAT 6e | 14 |
| 153776 | 26 | 2302 | STAT 6c | 137 |
| 153776 | 26 | 2111 | STAT 6b | 138 |
| 153777 | 27 | 2790 | STAT 6 | 11 |
| 153777 | 27 | 2657 | STAT 6c | 137 |
| 153777 | 27 | 2466 | STAT 6b | 138 |
| 153778 | 28 | 2020 | STAT 6 | 11 |
| 153778 | 28 | 1886 | STAT 6c | 137 |
| 153778 | 28 | 1695 | STAT 6b | 138 |
| 153779 | 29 | 1920 | STAT 6 | 11 |
| 153779 | 29 | 1595 | STAT 6b | 138 |
| 153780 | 30 | 507 | STAT 6 | 11 |
| 153780 | 30 | 457 | STAT 6c | 137 |
| 153781 | 31 | 3133 | STAT 6 | 11 |
| 153781 | 31 | 3000 | STAT 6c | 137 |
| 153781 | 31 | 2809 | STAT 6b | 138 |
| 153782 | 32 | 532 | STAT 6 | 11 |
| 153782 | 32 | 482 | STAT 6c | 137 |
| 153783 | 33 | 1912 | STAT 6 | 11 |
| 153783 | 33 | 1587 | STAT 6b | 138 |
| 153784 | 34 | 1934 | STAT 6 | 11 |
| 153784 | 34 | 1609 | STAT 6b | 138 |
| 153785 | 35 | 2593 | STAT 6 | 11 |
| 153785 | 35 | 2460 | STAT 6c | 137 |
| 153785 | 35 | 2269 | STAT 6b | 138 |
| 153786 | 36 | 1628 | STAT 6 | 11 |
| 153786 | 36 | 377 | STAT 6d | 13 |
| 153786 | 36 | 1578 | STAT 6c | 137 |
| 153786 | 36 | 1303 | STAT 6b | 138 |
| 153787 | 37 | 194 | STAT 6 | 11 |
| 153787 | 37 | 76 | STAT 6c | 137 |
| 153787 | 37 | 8 | STAT 6b | 138 |
| 153788 | 38 | 759 | STAT 6 | 11 |
| 153788 | 38 | 709 | STAT 6c | 137 |
| 153788 | 38 | 434 | STAT 6b | 138 |
| 153789 | 39 | 387 | STAT 6 | 11 |
| 153789 | 39 | 337 | STAT 6c | 137 |
| 153790 | 40 | 3114 | STAT 6 | 11 |
| 153790 | 40 | 2981 | STAT 6c | 137 |
| 153790 | 40 | 2790 | STAT 6b | 138 |
| 153791 | 41 | 2087 | STAT 6 | 11 |
| 153791 | 41 | 1953 | STAT 6c | 137 |
| 153791 | 41 | 1762 | STAT 6b | 138 |
| 153792 | 42 | 909 | STAT 6 | 11 |
| 153792 | 42 | 859 | STAT 6c | 137 |
| 153792 | 42 | 584 | STAT 6b | 138 |
| 153793 | 43 | 2112 | STAT 6 | 11 |
| 153793 | 43 | 1978 | STAT 6c | 137 |
| 153793 | 43 | 1787 | STAT 6b | 138 |
| 153794 | 44 | 261 | STAT 6 | 11 |
| 153794 | 44 | 211 | STAT 6c | 137 |
| 153794 | 44 | 75 | STAT 6b | 138 |
| 153795 | 45 | 2280 | STAT 6 | 11 |
| 153795 | 45 | 142 | STAT 6e | 14 |
| 153795 | 45 | 2146 | STAT 6c | 137 |
| 153795 | 45 | 1955 | STAT 6b | 138 |
| 153796 | 46 | 1877 | STAT 6 | 11 |
| 153796 | 46 | 1552 | STAT 6b | 138 |
| 153797 | 47 | 1320 | STAT 6 | 11 |
| 153797 | 47 | 1270 | STAT 6c | 137 |
| 153797 | 47 | 995 | STAT 6b | 138 |
| 153798 | 48 | 1059 | STAT 6 | 11 |
| 153798 | 48 | 1009 | STAT 6c | 137 |
| 153798 | 48 | 734 | STAT 6b | 138 |
| 153799 | 49 | 1786 | STAT 6 | 11 |
| 153799 | 49 | 535 | STAT 6d | 13 |

TABLE 3-continued

Targeting of individual oligonucleotides to specific variants of STAT 6

| ISIS # | OLIGO SEQ ID NO. | TARGET SITE | VARIANT | VARIANT SEQ ID NO. |
|---|---|---|---|---|
| 153799 | 49 | 1736 | STAT 6c | 137 |
| 153799 | 49 | 1461 | STAT 6b | 138 |
| 153800 | 50 | 1275 | STAT 6 | 11 |
| 153800 | 50 | 1225 | STAT 6c | 137 |
| 153800 | 50 | 950 | STAT 6b | 138 |
| 153801 | 51 | 443 | STAT 6 | 11 |
| 153801 | 51 | 393 | STAT 6c | 137 |
| 195427 | 52 | 154 | STAT 6 | 11 |
| 195427 | 52 | 36 | STAT 6c | 137 |
| 195428 | 53 | 273 | STAT 6 | 11 |
| 195428 | 53 | 223 | STAT 6c | 137 |
| 195428 | 53 | 87 | STAT 6b | 138 |
| 195429 | 54 | 656 | STAT 6 | 11 |
| 195429 | 54 | 606 | STAT 6c | 137 |
| 195429 | 54 | 331 | STAT 6b | 138 |
| 195430 | 55 | 833 | STAT 6 | 11 |
| 195430 | 55 | 783 | STAT 6c | 137 |
| 195430 | 55 | 508 | STAT 6b | 138 |
| 195431 | 56 | 1200 | STAT 6 | 11 |
| 195431 | 56 | 1150 | STAT 6c | 137 |
| 195431 | 56 | 875 | STAT 6b | 138 |
| 195432 | 57 | 1405 | STAT 6 | 11 |
| 195432 | 57 | 1355 | STAT 6c | 137 |
| 195432 | 57 | 1080 | STAT 6b | 138 |
| 195433 | 58 | 1730 | STAT 6 | 11 |
| 195433 | 58 | 479 | STAT 6d | 13 |
| 195433 | 58 | 1680 | STAT 6c | 137 |
| 195433 | 58 | 1405 | STAT 6b | 138 |
| 195434 | 59 | 2002 | STAT 6 | 11 |
| 195434 | 59 | 1868 | STAT 6c | 137 |
| 195434 | 59 | 1677 | STAT 6b | 138 |
| 195435 | 60 | 2267 | STAT 6 | 11 |
| 195435 | 60 | 129 | STAT 6e | 14 |
| 195435 | 60 | 2133 | STAT 6c | 137 |
| 195435 | 60 | 1942 | STAT 6b | 138 |
| 195436 | 61 | 2620 | STAT 6 | 11 |
| 195436 | 61 | 2487 | STAT 6c | 137 |
| 195436 | 61 | 2296 | STAT 6b | 138 |
| 195437 | 62 | 2813 | STAT 6 | 11 |
| 195437 | 62 | 2680 | STAT 6c | 137 |
| 195437 | 62 | 2489 | STAT 6b | 138 |
| 195438 | 63 | 3058 | STAT 6 | 11 |
| 195438 | 63 | 2925 | STAT 6c | 137 |
| 195438 | 63 | 2734 | STAT 6b | 138 |
| 195439 | 64 | 23 | STAT 6 | 11 |
| 195440 | 65 | 38 | STAT 6 | 11 |
| 195441 | 66 | 3185 | STAT 6 | 11 |
| 195441 | 66 | 3052 | STAT 6c | 137 |
| 195441 | 66 | 2861 | STAT 6b | 138 |
| 195442 | 67 | 3230 | STAT 6 | 11 |
| 195442 | 67 | 3097 | STAT 6c | 137 |
| 195442 | 67 | 2906 | STAT 6b | 138 |
| 195443 | 68 | 3531 | STAT 6 | 11 |
| 195443 | 68 | 3398 | STAT 6c | 137 |
| 195443 | 68 | 3207 | STAT 6b | 138 |
| 195444 | 69 | 3539 | STAT 6 | 11 |
| 195444 | 69 | 3406 | STAT 6c | 137 |
| 195444 | 69 | 3215 | STAT 6b | 138 |
| 195445 | 70 | 3585 | STAT 6 | 11 |
| 195445 | 70 | 3452 | STAT 6c | 137 |
| 195445 | 70 | 3261 | STAT 6b | 138 |
| 195446 | 71 | 3599 | STAT 6 | 11 |
| 195446 | 71 | 3466 | STAT 6c | 137 |
| 195446 | 71 | 3275 | STAT 6b | 138 |
| 195447 | 72 | 3629 | STAT 6 | 11 |
| 195447 | 72 | 3496 | STAT 6c | 137 |
| 195447 | 72 | 3305 | STAT 6b | 138 |
| 195448 | 73 | 3779 | STAT 6 | 11 |
| 195448 | 73 | 3646 | STAT 6c | 137 |
| 195448 | 73 | 3455 | STAT 6b | 138 |
| 195449 | 74 | 3835 | STAT 6 | 11 |
| 195449 | 74 | 3702 | STAT 6c | 137 |
| 195449 | 74 | 3511 | STAT 6b | 138 |
| 195453 | 78 | 1567 | STAT 6 | 11 |
| 195453 | 78 | 1517 | STAT 6c | 137 |
| 195453 | 78 | 1242 | STAT 6b | 138 |
| 195455 | 80 | 624 | STAT 6d | 13 |
| 195456 | 81 | 90 | STAT 6e | 14 |
| 195458 | 83 | 9 | STAT 6d | 13 |
| 195459 | 84 | 148 | STAT 6d | 13 |
| 195460 | 85 | 654 | STAT 6d | 13 |
| 195461 | 86 | 66 | STAT 6e | 14 |

What is claimed is:

1. A compound 12 to 50 nucleobases in length and having a nucleobase sequence that comprises at least an 8 nucleobase portion of a sequence selected from any one of SEQ ID NOs: 16-27, 29-35, 37-52, 54-77, and 79-86, and wherein the nucleobase sequence is at least 90% complementary to a nucleic acid molecule encoding STAT 6 as measured over the entirety of the nucleobase sequence.

2. A compound 12 to 50 nucleobases in length targeted to a nucleic acid molecule encoding STAT 6, wherein said compound comprises at least an 8 nucleobase portion of a sequence selected from any one of SEQ ID NOs: 16-27, 29-35, 37-52, 54-77, and 79-86.

3. The compound of claim 2, comprising 15 to 30 nucleobases in length.

4. The compound of claim 1, comprising an oligonucleotide.

5. The compound of claim 4, comprising an antisense oligonucleotide.

6. The compound of claim 4, comprising a chimeric oligonucleotide.

7. The compound of claim 1, wherein the nucleic acid molecule encoding STAT 6 is selected from any one of SEQ ID NOs: 4, 11, 12, 13, 14, 137 and 138.

8. The compound of claim 1, having at least 95% complementarity with a nucleic acid molecule encoding STAT.

9. The compound of claim 1, having at least one modified internucleoside linkage, sugar moiety, and/or nucleobase.

10. The compound of claim 1, wherein the modified sugar moiety is a 2'-O-(2-methoxyethyl) (2'-MOE) sugar moiety.

11. The compound of claim 1, wherein the modified sugar moiety is a bicyclic sugar moiety.

12. The compound of claim 1, wherein the modified internucleoside linkage is a phosphorothioate internucleoside linkage.

13. The compound of claim 1, wherein the modified nucleobase is a 5-methylcyto sine.

14. A compound 12 to 50 nucleobases in length and having a nucleobase sequence that comprises at least an 8 nucleobase portion of a sequence selected from any one of SEQ ID NOs: 16-27, 29-35, 37-52, 54-77, and 79-86, wherein the nucleobase sequence is at least 90% complementary to a nucleic acid molecule encoding STAT 6 as measured over the entirety of the nucleobase sequence, and wherein the compound comprises at least one modified internucleoside linkage, sugar moiety, or nucleobase.

15. A kit or assay device comprising the compound of claim 1.

16. A method of inhibiting the expression of STAT 6 in cells or tissues comprising contacting said cells or tissues with the compound of claim 1 so that expression of STAT 6 is inhibited.

17. A method of treating an animal having a disease or condition associated with STAT 6 comprising administering to said animal a therapeutically or prophylactically effective amount of the compound of claim 1 so that expression of STAT 6 is inhibited and the animal is treated.

18. The method of claim 17, wherein the disease or condition is an autoimmune disorder.

19. The compound of claim 1, comprising 15 to 30 nucleobases in length.

20. The compound of claim 14, comprising 15 to 30 nucleobases in length.

* * * * *